United States Patent
Congy et al.

(10) Patent No.: US 7,915,258 B2
(45) Date of Patent: Mar. 29, 2011

(54) SUBSTITUTED 2,5- DIHYDRO- 3H-PYRAZOLO[4,3-C]PYRIDAZIN- 3-ONE DERIVATIVES, PREPARATION THEREOF AND THERAPEUTIC USE OF THE SAME

(75) Inventors: Christian Congy, Paris (FR); Victor Dos Santos, Paris (FR); Murielle Rinaldi-Carmona, Paris (FR); Arnaud Rouquette, Paris (FR); Didier Van Broeck, Paris (FR)

(73) Assignee: Sanofi-Aventis, Paris (FR)

( * ) Notice: Subject to any disclaimer, the term of this patent is extended or adjusted under 35 U.S.C. 154(b) by 43 days.

(21) Appl. No.: 12/468,294

(22) Filed: May 19, 2009

(65) Prior Publication Data

US 2009/0281107 A1 Nov. 12, 2009

Related U.S. Application Data

(63) Continuation of application No. PCT/FR2007/001889, filed on Nov. 19, 2007.

(30) Foreign Application Priority Data

Nov. 23, 2006 (FR) ..................................... 06 10371

(51) Int. Cl.
| | |
|---|---|
| A61K 31/4985 | (2006.01) |
| C07D 487/04 | (2006.01) |
| A61P 25/22 | (2006.01) |
| A61P 25/24 | (2006.01) |
| A61P 25/18 | (2006.01) |
| A61P 25/06 | (2006.01) |
| A61P 25/16 | (2006.01) |
| A61P 25/28 | (2006.01) |
| A61P 1/06 | (2006.01) |
| A61P 23/00 | (2006.01) |

(52) U.S. Cl. ........................................ 514/248; 544/236
(58) Field of Classification Search .................. 544/236; 514/248

See application file for complete search history.

(56) References Cited

U.S. PATENT DOCUMENTS

| 4,345,934 A | 8/1982 | Fujimoto et al. |
|---|---|---|
| 5,624,941 A | 4/1997 | Barth et al. |
| 5,808,062 A | 9/1998 | Domagala et al. |
| 2009/0325968 A1* | 12/2009 | Green et al. ................... 514/248 |
| 2010/0210687 A1* | 8/2010 | Cooper et al. .................. 514/321 |

FOREIGN PATENT DOCUMENTS

| EP | 0576357 | 12/1993 |
|---|---|---|
| EP | 0656354 | 6/1995 |
| WO | WO 00/46209 | 8/2000 |
| WO | WO 2004/108728 | 12/2004 |
| WO | WO 2005/061504 | 7/2005 |

OTHER PUBLICATIONS

Bouaboula, M., et. al., A Selective Inverse Agonist for Central Cannabinoid Receptor Inhibits Mitogen-Activated Protein Kinase Activation Stimulated by Insulin or Insulin-Like Growth Factor 1, The Journal of Biological Chemistry, vol. 272, No. 35, (1997), pp. 22330-22339.

Bouaboula, M., et. al., Stimulation of Cannabinoid Receptor CB1 Induces Krox-24 Expression in Human Astrocytoma Cells, The Journal of Biological Chemistry, vol. 270, No. 23, (1995), pp. 13973-13980.

Keshavamurthy, K. S., et. al., Preparation of Acid Anhydrides, Amides, and Esters Using Chlorosulfonyl Isocyanate as a Dehydrating Agent, Synthesis, (1982), pp. 506-508.

Mispelaere-Canivet, C., et. al., Pd2(dba)3/Xantphos-Catalyzed Cross-Coupling of Thiols and Aryl Bromides/Triflates, Tetrahedron, vol. 61, (2005), pp. 5253-5259.

Rinaldi-Carmona, M., et. al., Biochemical and Pharmacological Characterisation of SR141716A, The First Potent and Selective Brain Cannabinoid Receptor Antagonist, Life Sciences, vol. 56, No. 23/24, pp. 1941-1947, (1995).

Rinaldi-Carmona, M., et. al., Characterization of Two Cloned Human CB1 Cannabinoid Receptor Isoforms, The Journal of Pharmacology and Experimental Therapeutics, vol. 278, No. 2, pp. 871-878, (1996).

Rinaldi-Carmona, M., et. al., SR141716A, A Potent and Selective Antogonist of the Brain Cannabinoid Receptor, Febs Letters, vol. 350, (1994) pp. 240-244.

Rinaldi-Carmona, M., et. al., R147778 [5-(4-Bromophenyl)-1-(2,4-Dichlorophenyl)-4-ethyl-N-(1-Piperidinyl)-1H-Pyrazole-3-Carboxamide], A New Potent and Selective Antagonist of the CB1 Cannabinold Receptor: Biochemical and Pharmacological Characterization, The Journal of Pharmacology and Experimental Therapeutics, vol. 310, No. 3, (2004), pp. 905-914.

Qi, C.-M., et. al., Synthesis and Hybridizing Activity of Novel Chemical Hybridizing Agent Pyridazinone Derivatives, Youji Huaxue, (2004), vol. 24 No. 6, pp. 645-649 (Chinese Journal of Organic Chemistry, vol. 24, No. 6, (2004), pp. 645-649).

* cited by examiner

*Primary Examiner* — James O Wilson
*Assistant Examiner* — Cecilia M Jaisle
(74) *Attorney, Agent, or Firm* — Serena Farquharson, Esq.; Scully, Scott, Murphy & Presser, P.C.

(57) ABSTRACT

The invention relates to compounds having the formula (I):

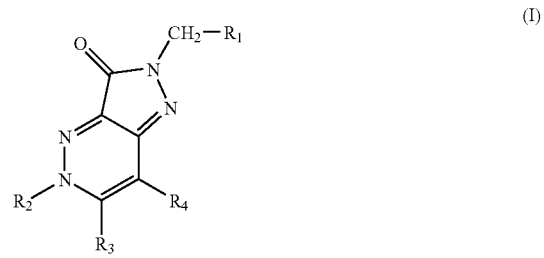

(I)

Wherein $R_1$, $R_2$, $R_3$ and $R_4$ are as described herein. Also disclosed are the method of preparation and their use in therapy.

20 Claims, No Drawings

SUBSTITUTED 2,5-DIHYDRO-3H-PYRAZOLO[4,3-C]PYRIDAZIN-3-ONE DERIVATIVES, PREPARATION THEREOF AND THERAPEUTIC USE OF THE SAME

CROSS REFERENCE TO RELATED APPLICATIONS

This application is a continuation of International application No. PCT/FR2007/001,889, Nov. 19, 2007, which is incorporated herein by reference in its entirety; which claims the benefit of priority of French Patent Application No. 06/10, 371, filed Nov. 23, 2006.

BACKGROUND OF THE INVENTION

1. Field of the Invention

The present invention relates to substituted 2,5-dihydro-3H-pyrazolo-[4,3-c]pyridazin-3-one derivatives, to the preparation thereof and to the therapeutic use thereof.

2. Description of the Art

Diphenylpyrazole derivatives having an affinity for cannabinoid $CB_1$ receptors have been described in particular in U.S. Pat. No. 5,624,941, EP 0 576 357, EP 0 656 354 and EP 1 150 961.

2,5-Dihydro-3H-pyrazolo[4,3-c]pyridazin-3-one derivatives having an activity as hybridizing chemical agents are described in Youji Huaxue, 2004, 24(6), 645-649.

Novel substituted 2,5-dihydro-3H-pyrazolo[4,3-c]pyridazin-3-one derivatives which have cannabinoid CB1 receptor antagonist properties, located centrally and/or peripherally, have now been found.

SUMMARY OF THE INVENTION

A subject of the present invention is compounds corresponding to the formula:

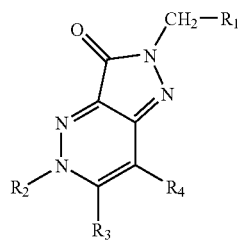

(I)

in which:

$R_1$ is:
- a $(C_1-C_{12})$alkyl which is unsubstituted or substituted one or more times with a fluorine atom;
- a non-aromatic $(C_3-C_{12})$ carbocyclic radical which is unsubstituted or substituted one or more times with substituents selected independently from a $(C_1-C_4)$ alkyl, a $(C_1-C_4)$alkoxy, a fluorine atom, a hydroxyl, trifluoromethyl radical, a trifluoromethoxy radical and a $(C_1-C_4)$alkylthio;
- a phenyl which is unsubstituted or substituted one or more times with substituents selected independently from a halogen atom, a hydroxyl, an Alk group, an OAlk group, a methylenedioxy, a $CH_2$—NHAlk group, a —$CH_2N(Alk)_2$ group, a cyano, a nitro, an $S(O)_n$Alk group, an $OS(O)_n$Alk group, a $(C_1-C_4)$alkylcarbonyl group and a $(C_1-C_4)$alkoxycarbonyl group;
- or from a phenyl, phenoxy, pyrrolyl, imidazolyl, pyridyl, pyrazolyl, oxazolyl, thiazolyl, triazolyl or thiadiazolyl radical, said radical being unsubstituted or substituted one or more times with a $(C_1-C_4)$alkyl;
- a benzyl which is unsubstituted or substituted one or more times on the phenyl with substituents selected independently from a halogen atom, an Alk group, a hydroxyl, an OAlk group, a methylenedioxy, an $S(O)_n$Alk group and an $OS(O)_n$Alk group;
- a phenethyl which is unsubstituted or substituted one or more times on the phenyl with substituents selected independently from a halogen atom, a $(C_1-C_4)$alkyl, a $(C_1-C_4)$alkoxy, a trifluoromethyl radical and a trifluoromethoxy radical;
- a benzhydryl; a benzhydrylmethyl;
- an aromatic heterocyclic radical selected from a pyrrolyl, an imidazolyl, a furyl, a thienyl, a pyrazolyl, an oxazolyl, a pyridyl, an indolyl, a benzothienyl and a thieno[3,2-b]thienyl, said radical being unsubstituted or substituted one or more times with substituents selected independently from a halogen atom, an Alk group, an OAlk group, a cyano, a nitro and an $S(O)_n$Alk group;

$R_2$ is a phenyl which is unsubstituted or substituted one or more times with substituents selected independently from a halogen atom, a hydroxyl, an Alk group, an OAlk group, an $S(O)_n$Alk group, an $OS(O)_n$Alk group, an —$O(CH_2)_mR_5$ group or an —$S(CH_2)_mR_6$ group;

$R_3$ is a phenyl which is unsubstituted or substituted one or more times with substituents selected independently from a halogen atom, a hydroxyl, an Alk group, an OAlk group, an $S(O)_n$Alk group, an $OS(O)_n$Alk group, an —$O(CH_2)_mR_5$ group or an —$S(CH_2)_mR_6$ group;

$R_4$ is a hydrogen atom, a $(C_1-C_4)$alkyl, a $(C_1-C_4)$alkoxy or a hydroxyl;

$R_5$ is an —$NR_7R_8$ group or an —SAlk group;

$R_6$ is a hydroxyl, an —$NR_7R_8$ group, an $NR_7COR_8$ group or an —$NR_7SO_2R_9$ group;

$R_7$ is a hydrogen atom or a $(C_1-C_4)$alkyl;

$R_8$ is a hydrogen atom, an Alk group or a $(C_3-C_7)$cycloalkyl;

$R_9$ is a $(C_1-C_4)$alkyl;

m is 2 or 3;

n is 0, 1 or 2;

Alk is a $(C_1-C_4)$alkyl which is unsubstituted or substituted one or more times with a fluorine atom.

The compounds of formula (I) can contain one or more asymmetrical carbon atoms. They can therefore exist in the form of enantiomers or of diastereoisomers. These enantiomers and diastereoisomers and mixtures thereof, including racemic mixtures, are part of the invention.

The compounds of formula (I) can exist in the form of bases or of addition salts with acids. Such addition salts are part of the invention.

These salts are advantageously prepared with pharmaceutically acceptable acids, but the salts of other acids that can be used for purifying or isolating the compounds of formula (I) are also part of the invention.

The compounds of formula (I) can exist in the form of hydrates or of solvates, i.e. in the form of associations or combinations with one or more molecules of water or with a solvent. Such hydrates and solvates are also part of the invention.

DETAILED DESCRIPTION OF THE INVENTION

The term "halogen atom" is intended to mean a bromine, chlorine, fluorine or iodine atom.

The term "$(C_1$-$C_4)$alkyl" or, respectively, "$(C_1$-$C_{12})$alkyl" is intended to mean a linear or branched alkyl radical containing from one to four carbon atoms or, respectively, from one to twelve carbon atoms, such as the methyl, ethyl, propyl, isopropyl, butyl, isobutyl, sec-butyl, tert-butyl, pentyl, isopentyl, hexyl, isohexyl, heptyl, octyl, nonyl, decyl, undecyl or dodecyl radical.

The term "$(C_1$-$C_4)$alkoxy" is intended to mean a linear or branched alkoxy radical containing from one to four carbon atoms, such as the methoxy, ethoxy, propoxy, isopropoxy, butoxy, sec-butoxy or tert-butoxy radical.

The term "$(C_3$-$C_7)$cycloalkyl" is intended to mean a cyclic alkyl group containing from 3 to 7 carbon atoms, such as the cyclopropyl, cyclobutyl, cyclopentyl, cyclohexyl or cycloheptyl group.

The non-aromatic $C_3$-$C_{12}$ carbocyclic radicals comprise monocyclic or condensed bridged or spiro polycyclic radicals. The monocyclic radicals include $(C_3$-$C_7)$cycloalkyls. The condensed, bridged or spiro di- or tricyclic radicals include, for example, norbornyl, bornyl, isobornyl, noradamantyl, adamantyl, spiro[5.5]undecyl, bicyclo[2.2.1]heptyl, bicyclo[3.2.1]octyl and bicyclo[3.1.1]heptyl radicals.

Among the compounds of formula (I), which are subjects of the invention, the following are singled out:

the compounds of formula (IA) in which $R_1$ is:
 a $(C_1$-$C_{12})$alkyl which is unsubstituted or substituted one or more times with a fluorine atom;
the substituents $R_2$, $R_3$ and $R_4$ are as defined for the compounds of formula (I).

The compounds of formula (IB) in which $R_1$ is:
 a non-aromatic $(C_3$-$C_{12})$carbocyclic radical which is unsubstituted or substituted one or more times with substituents selected independently from a $(C_1$-$C_4)$alkyl, a $(C_1$-$C_4)$alkoxy, a fluorine atom, a hydroxyl, a trifluoromethyl radical, a trifluoromethoxy radical and a $(C_1$-$C_4)$alkylthio;
the substituents $R_2$, $R_3$ and $R_4$ are as defined for the compounds of formula (I).

The compounds of formula (IC) in which $R_1$ is:
 a phenyl which is unsubstituted or substituted one or more times with substituents selected independently from a halogen atom, a hydroxyl, an Alk group, an OAlk group, a methylenedioxy, a $CH_2$—NHAlk group, a —$CH_2N$(Alk)$_2$ group, a cyano, a nitro, an S(O)$_n$Alk group, an OS(O)$_n$Alk group, a $(C_1$-$C_4)$alkylcarbonyl group and a $(C_1$-$C_4)$alkoxycarbonyl group; or from a phenyl, phenoxy, pyrrolyl, imidazolyl, pyridyl, pyrazolyl, oxazolyl, thiazolyl, triazolyl or thiadiazolyl radical, said radical being unsubstituted or substituted one or more times with a $(C_1$-$C_4)$alkyl;
the substituents $R_2$, $R_3$ and $R_4$ are as defined for the compounds of formula (I).

The compounds of formula (ID) in which $R_1$ is:
 a benzyl which is unsubstituted or substituted one or more times on the phenyl with substituents selected independently from a halogen atom, an Alk group, a hydroxyl, an OAlk group, a methylenedioxy, an S(O)$_n$Alk group and an OS(O)$_n$Alk group;
the substituents $R_2$, $R_3$ and $R_4$ are as defined for the compounds of formula (I).

The compounds of formula (IE) in which $R_1$ is:
 an aromatic heterocyclic radical selected from a pyrrolyl, an imidazolyl, a furyl, a thienyl, a pyrazolyl, an oxazolyl, a pyridyl, an indolyl, a benzothienyl and a thieno[3,2-b]thienyl, said radical being unsubstituted or substituted one or more times with substituents selected independently from a halogen atom, an Alk group, an OAlk group, a cyano, a nitro and an S(O)$_n$Alk group;
the substituents $R_2$, $R_3$ and $R_4$ are as defined for the compounds of formula (I).

Among the compounds of formula (I), which are subjects of the invention, a first group of compounds consists of the compounds for which:

$R_1$ is:
 a $(C_1$-$C_{12})$alkyl;
 a $(C_3$-$C_7)$cycloalkyl which is unsubstituted or substituted with $(C_1$-$C_4)$alkyl, a trifluoromethyl radical; an adamantyl;
 a phenyl which is unsubstituted or substituted one or more times with substituents selected independently from a halogen atom, an Alk group, an OAlk group, a $CH_2N$(Alk)$_2$ group, an —S(O)$_n$Alk group, a $(C_1$-$C_4)$alkoxycarbonyl group; or from a phenyl, triazolyl or thiadiazolyl radical;
 a benzyl which is unsubstituted or substituted one or more times on the phenyl with substituents selected independently from a halogen atom and an Alk group;
 an aromatic heterocyclic radical selected from a pyridyl, a thieno[3,2-b]thienyl and a benzothienyl, said radical being unsubstituted or substituted with a halogen atom or a trifluoromethyl radical;

$R_2$ is a phenyl mono- or disubstituted with a halogen atom, a hydroxyl, an OAlk group, an S(O)$_n$Alk group, an OS(O)$_n$Alk group, an —O(CH$_2$)$_m$R$_5$ group or an —S(CH$_2$)$_m$R$_6$ group;

$R_3$ is a phenyl mono- or disubstituted with a halogen atom, an OAlk group, an S(O)$_n$Alk group, an —O(CH$_2$)$_m$R$_5$ group or an —S(CH$_2$)$_m$R$_6$ group;

$R_4$ is a hydrogen atom, a $(C_1$-$C_4)$alkyl, a $(C_1$-$C_4)$alkoxy or a hydroxyl;

n is 0, 1 or 2;

Alk is a $(C_1$-$C_4)$alkyl which is unsubstituted or substituted one or more times with a fluorine atom;

The substituents m, $R_5$ and $R_6$ are as defined for the compounds of formula (I);

and also the addition salts thereof, hydrates thereof or solvates thereof.

Among the compounds of formula (I), which are subjects of the invention, the compounds singled out are the compounds of formula (IC) in which:

$R_1$ is:
 a phenyl which is unsubstituted or substituted one or more times with substituents selected independently from a halogen atom, an Alk group, an OAlk group and an —S(O)$_n$Alk group;

$R_2$ is a phenyl mono- or disubstituted with a halogen atom, a hydroxyl, an OAlk group, an S(O)$_n$Alk group, an OS(O)$_n$Alk group, an —O(CH$_2$)$_m$R$_5$ group or an —S(CH$_2$)$_m$R$_6$ group;

$R_3$ is a phenyl mono- or disubstituted with a halogen atom, an OAlk group, an S(O)$_n$Alk group, an —O(CH$_2$)$_m$R$_5$ group or an —S(CH$_2$)$_m$R$_6$ group;

$R_4$ is a hydrogen atom, a $(C_1$-$C_4)$alkyl, a $(C_1$-$C_4)$alkoxy or a hydroxyl;

n is 0, 1 or 2;

Alk is a $(C_1$-$C_4)$alkyl which is unsubstituted or substituted one or more times with a fluorine atom;

The substituents m, $R_5$ and $R_6$ are as defined for the compounds of formula (I);

and also the addition salts thereof, hydrates thereof or solvates thereof.

Among the compounds of formula (I), which are subjects of the invention, mention may also be made of the compounds for which:

$R_1$ is:
- a 1-propylbutyl;
- a cyclohexyl, a 4-tert-butylcyclohexyl, a 4-(trifluoromethyl)cyclohexyl; an adamantan-1-yl;
- a phenyl, 4-fluorophenyl, a 2-methylphenyl, a 4-methylphenyl, a 4-isopropyl-phenyl, a 4-butylphenyl, a 4-tert-butylphenyl, a 4-(trifluoromethyl)phenyl, a 4-methoxyphenyl, a 4-butoxyphenyl, a 4-tert-butoxyphenyl, a 3-(trifluoro-methoxy)phenyl, a 4-(trifluoromethoxy)phenyl, a 4-(difluoromethoxy)phenyl, a 4-(1,1,2,2-tetrafluoroethoxy)phenyl, a 4-(ethylthio)phenyl, a 3-[(trifluoro-methyl)thio]phenyl, a 4-[(trifluoromethyl)thio]phenyl, a 4-[(2,2,2-trifluoro-ethyl)thio]phenyl, a 4-(methylsulfonyl)phenyl, a 4-[[ethyl(propyl)amino]-methyl]phenyl, a 4-[[methyl(2,2,2-trifluoroethyl)amino]methyl]phenyl, a 3-chloro-4-(trifluoromethyl)phenyl, a 2-fluoro-4-(trifluoromethyl)phenyl, a 3-fluoro-4-(trifluoromethyl)phenyl, a 3-fluoro-4-propoxyphenyl, a 3-chloro-4-(trifluoromethoxy)phenyl, a 3,5-bis(trifluoromethyl)phenyl, a 4-(methoxy-carbonyl)phenyl, a biphenyl-4-yl, a 4-(1H-1,2,4-triazol-1-yl)phenyl, a 4-(1,2,3-thiadiazol-4-yl)phenyl;
- a benzyl, a [3,5-difluoro-4-(trifluoromethyl)phenyl]methyl;
- a pyridin-4-yl, a 6-(trifluoromethyl)pyridin-3-yl, a thieno[3,2-b]thien-2-yl, a 5-chloro-1-benzothien-2-yl;

$R_2$ is a 4-bromophenyl, a 4-chlorophenyl, a 4-fluorophenyl, a 4-methoxyphenyl, a 4-(methylthio)phenyl, a 4-hydroxyphenyl, a 4-[[(3,3,3-trifluoropropyl)sulfonyl]oxy]phenyl, a 4-[(propylsulfonyl)oxy]phenyl, a 2,4-dichlorophenyl, a 4-(trifluoromethoxy)phenyl, a 4-[(trifluoromethyl)thio]phenyl, a 4-[2-(dimethylamino)ethoxy]phenyl, a 4-[(3-hydroxypropyl)thio]phenyl, a 4-[(2-acetamido-ethyl)thio]phenyl or a 4-[[3-[(methylsulfonyl)amino]propyl]thio]phenyl;

$R_3$ is a 2-chlorophenyl, a 4-chlorophenyl, a 2,4-dichlorophenyl, a 4-bromo-2-chlorophenyl, a 2-chloro-4-fluorophenyl, a 2-chloro-4-methoxyphenyl, a 2-chloro-4-(methylthio)phenyl, a 2-chloro-4-(ethylthio)phenyl, a 2-chloro-4-[(3,3,3-trifluoropropyl)thio]phenyl, a 2-chloro-4-(2,2,2-trifluoroethoxy)phenyl, a 2-chloro-4-[2-(dimethylamino)ethoxy]phenyl, a 2-chloro-4-[2-(methylthio)ethoxy]phenyl, a 2-chloro-4-[(3-hydroxypropyl)thio]phenyl, a 2-chloro-4-[(2-acetamidoethyl)thio]phenyl, a 2-chloro-4-[[3-[(methylsulfonyl)amino]propyl]thio]phenyl, a 4-[(2-aminoethyl)thio]-2-chlorophenyl, a 2-chloro-4-[[2-(dimethylamino)ethyl]thio]phenyl, a 2-chloro-4-[[2-(diethylamino)ethyl]thio]phenyl, a 2-chloro-4-[[2-(isopropylamino)ethyl]thio]phenyl, a 2-chloro-4-[(2-formamidoethyl)thio]phenyl, a 2-chloro-4-[[2-[(methylsulfonyl)amino]ethyl]thio]phenyl, a 2-chloro-4-[[2-[(trifluoroacetyl)amino]ethyl]thio]phenyl or a 2-chloro-4-[[2-[(cyclopropylcarbonyl)amino]ethyl]thio]phenyl;

$R_4$ is a hydrogen atom, a methyl, a methoxy or a hydroxyl;
and also the addition salts thereof, hydrates thereof or solvates thereof.

Among the compounds of formula (I), which are subjects of the invention, mention may also be made of the compounds for which:

$R_1$ is:
- a 4-isopropylphenyl, a 4-tert-butylphenyl, a 4-(trifluoromethyl)phenyl, a 4-(trifluoromethoxy)phenyl, a 4-[(trifluoromethyl)thio]phenyl, a 2-fluoro-4-(trifluoromethyl)phenyl or a 3-fluoro-4-(trifluoromethyl)phenyl;

$R_2$ is a 4-bromophenyl, a 4-chlorophenyl, a 4-fluorophenyl, a 4-methoxyphenyl, a 4-(methylthio)phenyl, a 4-[[(3,3,3-trifluoropropyl)sulfonyl]oxy]phenyl, a 4-[(propylsulfonyl)oxy]phenyl or a 4-[[3-[(methylsulfonyl)amino]propyl]-thio]phenyl;

$R_3$ is a 2-chlorophenyl, a 2,4-dichlorophenyl, a 4-bromo-2-chlorophenyl, a 2-chloro-4-methoxyphenyl, a 2-chloro-4-(methylthio)phenyl, a 2-chloro-4-[2-(dimethylamino)ethoxy]phenyl, a 2-chloro-4-[2-(methylthio)ethoxy]phenyl, a 2-chloro-4-[(3-hydroxypropyl)thio]phenyl, a 2-chloro-4-[(2-acetamidoethyl)thio]phenyl, a 4-[(2-aminoethyl)thio]-2-chlorophenyl, a 2-chloro-4-[[2-(dimethyl-amino)ethyl]thio]phenyl, a 2-chloro-4-[[2-(diethylamino)ethyl]thio]phenyl, a 2-chloro-4-[[2-(isopropylamino)ethyl]thio]phenyl, a 2-chloro-4-[[2-[(methyl-sulfonyl)amino]ethyl]thio]phenyl, a 2-chloro-4-[(2-formamidoethyl)thio]phenyl, a 2-chloro-4-[[2-[(trifluoroacetyl)amino]ethyl]thio]phenyl or a 2-chloro-4-[[2-[(cyclopropylcarbonyl)amino]ethyl]thio]phenyl;

$R_4$ is a hydrogen atom;
and also the addition salts thereof, hydrates thereof or solvates thereof.

Among the compounds of the formula (I), which are subjects of the invention, mention may in particular be made of the following compounds:

- -5-(4-chlorophenyl)-6-(2,4-dichlorophenyl)-2-(4-isopropylbenzyl)-2,5-dihydro-3H-pyrazolo[4,3-c]pyridazin-3-one;
- -2-(4-tert-butylbenzyl)-5-(4-chlorophenyl)-6-(2,4-dichlorophenyl)-2,5-dihydro-3H-pyrazolo[4,3-c]pyridazin-3-one;
- -5-(4-chlorophenyl)-6-(2,4-dichlorophenyl)-2-[4-(trifluoromethyl)benzyl]-2,5-dihydro-3H-pyrazolo[4,3-c]pyridazin-3-one;
- -5-(4-chlorophenyl)-6-(2,4-dichlorophenyl)-2-[2-fluoro-4-(tri-fluoromethyl)benzyl]-2,5-dihydro-3H-pyrazolo[4,3-c]pyridazin-3-one;
- -5-(4-chlorophenyl)-6-(2,4-dichlorophenyl)-2-[4-[(trifluoromethyl)thio]benzyl]-2,5-dihydro-3H-pyrazolo[4,3-c]pyridazin-3-one;
- -5-(4-bromophenyl)-6-(2,4-dichlorophenyl)-2-(4-isopropylbenzyl)-2,5-dihydro-3H-pyrazolo[4,3-c]pyridazin-3-one;
- -5-(4-bromophenyl)-2-(4-butylbenzyl)-6-(2,4-dichlorophenyl)-2,5-dihydro-3H-pyrazolo[4,3-c]pyridazin-3-one;
- -5-(4-bromophenyl)-6-(2,4-dichlorophenyl)-2-[3-fluoro-4-(trifluoromethyl)benzyl]-2,5-dihydro-3H-pyrazolo[4,3-c]pyridazin-3-one;
- -5-(4-bromophenyl)-6-(2,4-dichlorophenyl)-2-[4-(trifluoromethoxy)benzyl]-2,5-dihydro-3H-pyrazolo[4,3-c]pyridazin-3-one;
- -5-(4-bromophenyl)-6-(2,4-dichlorophenyl)-2-[4-[(trifluoromethyl)thio]benzyl]-2,5-dihydro-3H-pyrazolo[4,3-c]pyridazin-3-one;
- -6-(2,4-dichlorophenyl)-5-[4-(methylthio)phenyl]-2-[4-(trifluoromethyl)benzyl]-2,5-dihydro-3H-pyrazolo[4,3-c]pyridazin-3-one;
- -6-(2,4-dichlorophenyl)-2-[2-fluoro-4-(trifluoromethyl)benzyl]-5-[4-(methylthio)phenyl]-2,5-dihydro-3H-pyrazolo[4,3-c]pyridazin-3-one;
- -6-(2,4-dichlorophenyl)-5-[4-(methylthio)phenyl]-2-[4-(trifluoromethoxy)benzyl]-2,5-dihydro-3H-pyrazolo[4,3-c]pyridazin-3-one;

- 6-(2-chlorophenyl)-5-(4-chlorophenyl)-2-[4-[(trifluoromethyl)thio]benzyl]-2,5-dihydro-3H-pyrazolo[4,3-c]pyridazin-3-one;
- 6-(2,4-dichlorophenyl)-5-(4-methoxyphenyl)-2-[4-[(trifluoromethoxy)benzyl]-2,5-dihydro-3H-pyrazolo[4,3-c]pyridazin-3-one;
- 6-(2,4-dichlorophenyl)-5-(4-methoxyphenyl)-2-[4-[(trifluoromethyl)thio]benzyl]-2,5-dihydro-3H-pyrazolo[4,3-c]pyridazin-3-one;
- 6-(2-chlorophenyl)-5-(4-fluorophenyl)-2-[4-[(trifluoromethyl)thio]benzyl]-2,5-dihydro-3H-pyrazolo[4,3-c]pyridazin-3-one;
- 4-[6-(2,4-dichlorophenyl)-3-oxo-2-[4-[(trifluoromethyl)thio]benzyl]-2,3-dihydro-5H-pyrazolo[4,3-c]pyridazin-5-yl]phenyl-3,3,3-trifluoropropane-1-sulfonate;
- 4-[6-(2,4-dichlorophenyl)-3-oxo-2-[4-[(trifluoromethyl)thio]benzyl]-2,3-dihydro-5H-pyrazolo[4,3-c]pyridazin-5-yl]phenylpropane-1-sulfonate;
- 6-(4-bromo-2-chlorophenyl)-5-[4-(methylthio)phenyl]-2-[4-(trifluoromethyl)benzyl]-2,5-dihydro-3H-pyrazolo[4,3-c]pyridazin-3-one;
- 6-{2-chloro-4-[(3-hydroxypropyl)thio]phenyl}-5-[4-(methylthio)phenyl]-2-[4-(trifluoromethyl)benzyl]-2,5-dihydro-3H-pyrazolo[4,3-c]pyridazin-3-one;
- 6-(4-bromo-2-chlorophenyl)-5-[4-(methylthio)phenyl]-2-{4-[(trifluoromethyl)thio]benzyl}-2,5-dihydro-3H-pyrazolo[4,3-c]pyridazin-3-one;
- N-(2-{[3-chloro-4-(5-[4-(methylthio)phenyl]-3-oxo-2-{4-[(trifluoromethyl)thio]benzyl}-3,5-dihydro-2H-pyrazolo[4,3-c]pyridazin-6-yl)phenyl]thio}ethyl)acetamide;
- 6-{2-chloro-4-[(3-hydroxypropyl)thio]phenyl}-5-[4-(methylthio)phenyl]-2-{4-[(trifluoromethyl)thio]benzyl}-2,5-dihydro-3H-pyrazolo[4,3-c]pyridazin-3-one;
- 6-(2-chloro-4-methoxyphenyl)-5-[4-(methylthio)phenyl]-2-[4-(trifluoromethyl)benzyl]-2,5-dihydro-3H-pyrazolo[4,3-c]pyridazin-3-one;
- 6-(2-chloro-4-methoxyphenyl)-5-[4-(methylthio)phenyl]-2-[4-(trifluoromethoxy)benzyl]-2,5-dihydro-3H-pyrazolo[4,3-c]pyridazin-3-one;
- 6-(2-chloro-4-methoxyphenyl)-5-[4-(methylthio)phenyl]-2-{4-[(trifluoromethyl)thio]benzyl}-2,5-dihydro-3H-pyrazolo[4,3-c]pyridazin-3-one;
- 6-{2-chloro-4-[2-(dimethylamino)ethoxy]phenyl}-5-[4-(methylthio)phenyl]-2-[4-(trifluoromethyl)benzyl]-2,5-dihydro-3H-pyrazolo[4,3-c]pyridazin-3-one;
- 6-{2-chloro-4-[2-(methylthio)ethoxy]phenyl}-5-[4-(methylthio)phenyl]-2-[4-(trifluoromethyl)benzyl]-2,5-dihydro-3H-pyrazolo[4,3-c]pyridazin-3-one;
- 6-[2-chloro-4-(methylthio)phenyl]-5-[4-(methylthio)phenyl]-2-[4-(trifluoromethyl)benzyl]-2,5-dihydro-3H-pyrazolo[4,3-c]pyridazin-3-one;
- 6-[2-chloro-4-(methylthio)phenyl]-5-[4-(methylthio)phenyl]-2-{4-[(trifluoromethyl)thio]benzyl}-2,5-dihydro-3H-pyrazolo[4,3-c]pyridazin-3-one;
- N-[3-({4-[6-(2,4-dichlorophenyl)-3-oxo-2-{4-[(trifluoromethyl)thio]benzyl}-2,3-dihydro-5H-pyrazolo[4,3-c]pyridazin-5-yl]phenyl}thio)propyl]methane-sulfonamide;
- N-{3-[(4-{6-(2,4-dichlorophenyl)-3-oxo-2-[4-(trifluoromethyl)benzyl]-2,3-dihydro-5H-pyrazolo[4,3-c]pyridazin-5-yl}phenyl)thio]propyl}methanesulfonamide;
- 6-{4-[(2-aminoethyl)thio]-2-chlorophenyl}-5-[4-(methylthio)phenyl]-2-[4-(trifluoromethyl)benzyl]-2,5-dihydro-3H-pyrazolo[4,3-c]pyridazin-3-one;
- 6-(2-chloro-4-{[2-(dimethylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one;
- 6-(2-chloro-4-{[2-(diethylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one;
- 6-(2-chloro-4-{[2-(isopropylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one;
- N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}methanesulfonamide;
- N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}formamide;
- N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}-2,2,2-trifluoroacetamide;
- N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}cyclopropanecarboxamide;

and also the addition salts thereof, hydrates thereof or solvates thereof.

In the following text, the term "protective group Pg" is intended to mean a group which makes it possible, firstly, to protect a reactive function such as a hydroxyl or an amine during a synthesis and, secondly, to regenerate the intact reactive function at the end of synthesis. Examples of protective groups and also methods of protection and deprotection are given in "Protective Group in Organic Synthesis", Green et al., 2nd Edition (John Wiley & Sons, Inc., New York), 1991.

In the following text, the term "leaving group" is intended to mean a group that can be readily cleaved from a molecule by heterolytic bond cleavage, with the departure of a pair of electrons. This group can thus be readily replaced with another group during a substitution reaction, for example. Such leaving groups are, for example, halogens or an activated hydroxyl group, such as a methanesulfonate, benzenesulfonate, p-toluenesulfonate, triflate, acetate, etc. Examples of leaving groups and also references for the preparation thereof are given in "Advances in Organic Chemistry", J. March, 3$^{rd}$ Edition, Wiley Interscience, 1985, p. 310-316.

In accordance with the invention, the compounds of formula (I) can be prepared according to a process which is characterized in that:

A compound of formula:

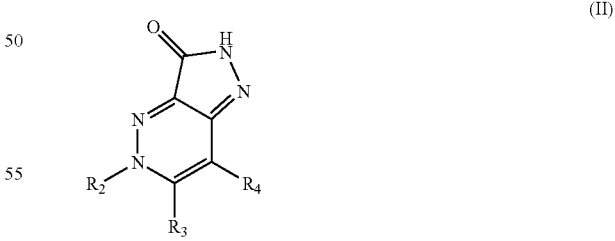

(II)

in which $R_2$, $R_3$ and $R_4$ are as defined for a compound of formula (I), is reacted with a compound of formula:

(III)

in which $R_1$ is as defined for a compound of formula (I) and Y is a leaving group as defined above, preferably a halogen atom or an activated hydroxyl group such as a methanesulfonate, benzenesulfonate, p-toluenesulfonate or triflate group.

The reaction is carried out in the presence of a base such as an alkali metal hydride, for example sodium hydride, or an alkali metal carbonate, for example potassium carbonate or cesium carbonate, in a solvent such as dioxane, N,N-dimethylformamide, tetrahydrofuran or a mixture of these solvents, and at a temperature between ambient temperature and the reflux temperature of the solvent.

According to a variant of the process, a compound of formula (I) in which $R_4$=—OH can also be prepared by reaction of a compound of formula (I) in which $R_4$=—OCH$_3$ with a strong acid such as hydrobromic acid, in a solvent such as acetic acid and at a temperature between ambient temperature and the reflux temperature of the solvent.

According to another variant, a compound of formula (I) in which $R_2$ or $R_3$=hydroxyphenyl can be prepared by reaction of a compound of formula (I) in which $R_2$ or $R_3$=methoxyphenyl with BBr$_3$, in a solvent such as dichloromethane and at a temperature between −20° C. and ambient temperature.

According to another variant, a compound of formula (I) in which $R_2$ or $R_3$=AlkS(O)$_n$O-phenyl can be prepared by reaction of a compound of formula (I) in which $R_2$ or $R_3$=hydroxyphenyl with a halide of formula Hal-S(O)$_n$Alk, in which Hal is a halogen atom, preferably chlorine, in the presence of a base such as triethylamine, in a solvent such as dichloromethane and at a temperature between −20° C. and ambient temperature.

According to another variant, a compound of formula (I) in which $R_2$ or $R_3$=phenyl-O(CH$_2$)$_m$R$_5$ can be prepared by reaction of a compound of formula (I) in which $R_2$ or $R_3$=phenyl-OH with a compound of formula Y—(CH$_2$)$_m$R$_5$, Y being as defined above and m and $R_5$ being as defined for a compound of formula (I). The reaction is carried out in the presence of a base such as an alkaline metal hydride, for example sodium hydride, or an alkaline metal carbonate, for example potassium carbonate or cesium carbonate, in a solvent such as dioxane, N,N-dimethylformamide, tetrahydrofuran, acetonitrile or ethanol or a mixture of these solvents, and at a temperature between ambient temperature and the reflux temperature of the solvent.

According to another variant, a compound of formula (I) in which $R_2$ or $R_3$=phenyl-S(CH$_2$)$_m$R$_6$ can be prepared by reaction of a compound of formula (I) in which $R_2$ or $R_3$=phenyl-Br with a compound of formula HS(CH$_2$)$_m$R$_6$, m and $R_6$ being as defined for a compound of formula (I). The reaction is carried out in the presence of a base and of the catalytic system Pd$_2$(dba)$_3$/xantphos according to the operating conditions described in Tetrahedron 2005, 61, 5253-5259.

According to another variant, a compound of formula (I) in which $R_2$ or $R_3$=phenyl-S(CH$_2$)$_m$R$_6$, in which $R_6$ is an —NR$_7$R$_8$, NR$_7$COR$_8$ or NR$_7$SO$_2$R$_9$ group, can be prepared from the compounds of formula (I) in which $R_2$ or $R_3$=phenyl-S—(CH$_2$)$_m$NH$_2$ using methods well known to those skilled in the art such as alkylation or acylation of amines.

According to another variant, the compounds of formula (I) in which $R_2$ or $R_3$=phenyl-S(CH$_2$)$_m$R$_6$, in which $R_6$ is an —NR$_7$SO$_2$R$_9$ group, can be prepared from the compounds of formula (I) in which $R_2$ or $R_3$=phenyl-S(CH$_2$)$_m$—OH and after activation of the hydroxyl function and reaction with a compound of formula HNR$_7$SO$_2$R$_9$, according to the methods well known to those skilled in the art.

The compounds of formula (I) thus obtained can be subsequently separated from the reaction medium and purified according to conventional methods, for example by crystallization or chromatography.

The compounds of formula (II) are prepared by cyclization of a compound of formula:

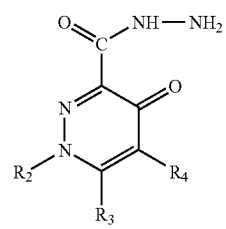

(IV)

in which $R_2$, $R_3$ and $R_4$ are as defined for a compound of formula (I). The reaction is carried out in the presence of an acid such as hydrochloric acid, in a solvent such as pyridine and at a temperature between ambient temperature and the reflux temperature of the solvent. The reaction can also be carried out in the presence of a base such as potassium tert-butoxide, in a solvent such as ethanol and at a temperature between ambient temperature and the reflux temperature of the solvent.

The compounds of formula (III) are known, commercially available or prepared according to known methods from the compounds of formula:

HO—CH$_2$—R$_1$   (V)

in which $R_1$ is as defined for a compound of formula (I). Thus, for example, when, in a compound of formula (III), Y is a halogen atom, a compound of formula (V) is treated with a halogenating agent such as SOCl$_2$, PCl$_5$, PBr$_3$, HBr or BBr$_3$, in a solvent such as dichloromethane or ether and at a temperature between 0° C. and ambient temperature. It is also possible to use methanesulfonyl chloride as halogenating agent, in the presence of a base such as triethylamine, in a solvent such as dichloromethane, and at a temperature between 0° C. and ambient temperature.

When, in a compound of formula (III), Y is a methanesulfonate, a benzenesulfonate, a p-toluenesulfonate or a trifluoromethanesulfonate, a compound of formula (V) is reacted with a sulfonyl chloride of formula W—SO$_2$—Cl in which W is a methyl, a phenyl, a p-tolyl or a trifluoromethyl. The reaction is carried out in the presence of a base such as triethylamine, pyridine or N,N-diisopropylethylamine, in a solvent such as dichloromethane or toluene and at a temperature between −20° C. and the reflux temperature of the solvent.

The compounds of formula (IV) are prepared by reaction of a compound of formula:

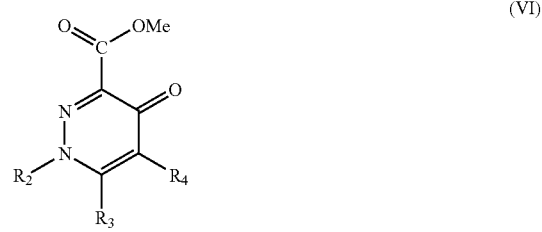

(VI)

in which $R_2$, $R_3$ and $R_4$ are as defined for a compound of formula (I), with hydrazine monohydrate, in a solvent such as dioxane, dichloromethane or methanol, or a mixture of these solvents, and at a temperature between 0° C. and ambient temperature.

The compounds of formula (V) are known, commercially available or prepared according to known methods from the compounds of formula:

(VII)

in which $R_1$ is as defined for a compound of formula (I) and Z is a hydroxyl or a ($C_1$-$C_2$)alkoxy. The reaction is carried out in the presence of a reducing agent such as borane or lithium aluminum hydride, in a solvent such as diethyl ether or tetrahydrofuran, and at a temperature between −20° C. and the reflux temperature of the solvent.

The compounds of formula (VI) are prepared by esterification of the compounds of formula:

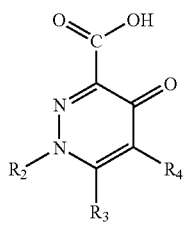
(VIII)

in which $R_2$, $R_3$ and $R_4$ are as defined for a compound of formula (I), according to conventional methods. For example, the reaction is carried out by the action of an alcohol, in the presence of isocyanatosulfuryl chloride and of triethylamine according to the method described in Synthesis, 1982, 506-508.

The compounds of formula (VII) are known, commercially available or prepared according to known methods.

The compounds of formula (VIII) are prepared according to known methods such as those described in U.S. Pat. No. 4,345,934.

Thus, for example, a pyrone derivative of formula:

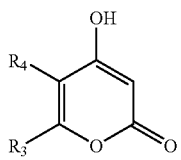
(IX)

in which $R_3$ and $R_4$ are as defined for a compound of formula (I), or a salt of the compound of formula (IX) prepared by treating the pyrone derivative with a water-soluble base such as sodium carbonate or potassium carbonate, is reacted with a diazonium salt, preferably the chloride, prepared by a conventional reaction of diazotization (action of sodium nitrite in an acidic medium in water at 0° C.) of an amine of formula:

$R_2$—$NH_2$ (X)

in which $R_2$ is as defined for a compound of formula (I). The reaction is carried out in an aqueous medium, at a temperature between −10° C. and ambient temperature. The hydrazinone compound thus obtained, of formula:

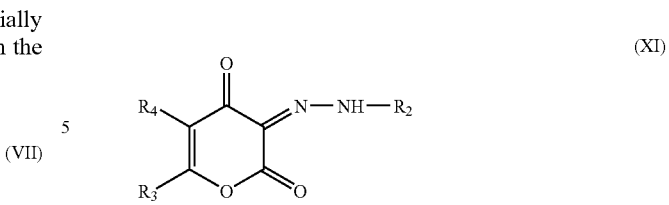
(XI)

is subsequently treated with a strong acid such as hydrochloric acid, in an aqueous medium, at a temperature between 0° C. and 100° C., so as to obtain, after rearrangement, the expected compound of formula (VIII).

The compounds of formula (IX) are prepared according to known methods such as those described in U.S. Pat. No. 5,808,062. Thus, for example, the compounds of formula (IX) are prepared according to SCHEME I below, in which $R_3$ and $R_4$ are as defined for a compound of formula (I):

SCHEME I

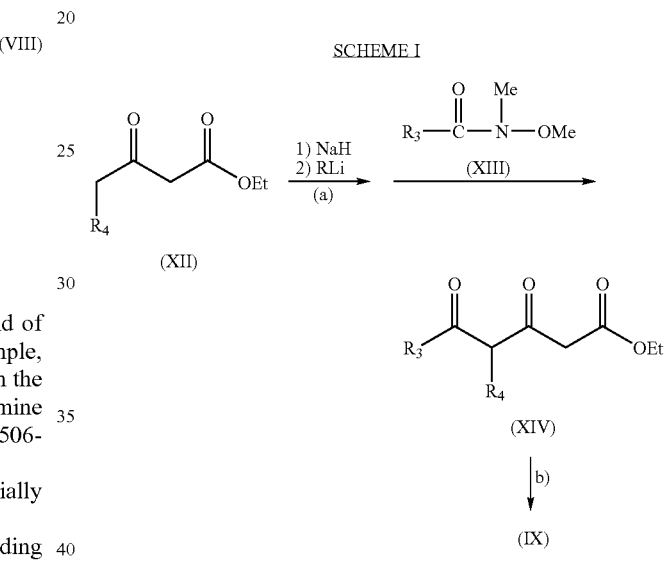

In stage a), a β-keto ester of formula (XII) is deprotonated by the action of a base such as an alkali metal hydride, for example sodium hydride, in a solvent such as diethyl ether or tetrahydrofuran, at a temperature between −10° C. and 0° C. The action of a second strong base, such as an alkyllithium (Rli), for example lithium diisopropylamide, makes it possible to obtain a dianion which is subsequently reacted with an acylating agent, for example an amide of formula (XIII), at a temperature between 0° C. and ambient temperature, so as to obtain a compound of formula (XIV).

In stage b), the compound of formula (XIV) is subsequently cyclized to a compound of formula (IX) by the action of a strong acid such as sulfuric acid, at a temperature between 0° C. and ambient temperature.

The compounds of formula (X) are known.
The compounds of formula (XII) are known.
The compounds of formula (XIII) are prepared by reaction of N-methoxy-methanamine with an acid halide of formula $R_3$COHal (XV) in which $R_3$ is as defined for a compound of formula (I) and Hal is a halogen atom, preferably chlorine, in the presence of a base such as triethylamine, in a solvent such as dichloromethane, and at a temperature between 0° C. and ambient temperature.

The compounds of formula (XV) are known or prepared according to known methods.

According to another of its aspects, a subject of the invention is also the compounds of formula (II). These compounds are of use as synthesis intermediates for the compounds of formula (I).

Thus, a subject of the invention is compounds of formula:

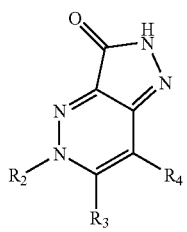

(II)

in which:
- $R_2$ is a phenyl which is unsubstituted or substituted one or more times with substituents selected independently from a halogen atom, a hydroxyl, an Alk group, an OAlk group, an $S(O)_n$Alk group or an $OS(O)_n$Alk group;
- $R_3$ is a phenyl which is unsubstituted or substituted one or more times with substituents selected independently from a halogen atom, a hydroxyl, an Alk group, an OAlk group, an $S(O)_n$Alk group or an $OS(O)_n$Alk group;
- $R_4$ is a hydrogen atom, a $(C_1$-$C_4)$alkyl, a $(C_1$-$C_4)$alkoxy or a hydroxyl;
- n is 0, 1 or 2;
- Alk is a $(C_1$-$C_4)$alkyl which is unsubstituted or substituted one or more times with a fluorine atom;

The following EXAMPLES describe the preparation of certain compounds in accordance with the invention. These examples are not limiting and merely illustrate the present invention. The numbers of the compounds exemplified refer to those given in TABLE (VI) hereinafter, which illustrates the chemical structures and the physical properties of some compounds according to the invention.

In the preparations and in the examples, the following abbreviations are used:
ether: diethyl ether
iso ether: diisopropyl ether
DMSO: dimethyl sulfoxide
DMF: N,N-dimethylformamide
THF: tetrahydrofuran
DCM: dichloromethane
EtOAc: ethyl acetate
DIPEA: diisopropylethylamine
TFA: trifluoroacetic acid
$Pd_2(dba)_3$: tris(dibenzylideneacetone)dipalladium(0)
Xantphos: 4,5-bis(diphenylphosphino)-9,9-dimethylxanthene;
2N hydrochloric ether: 2N solution of hydrochloric acid in diethyl ether
Mp: melting point
AT: ambient temperature
Bp: boiling point
HPLC: High performance liquid chromatography
Silica H: silica gel 60H sold by Merck (DARMSTAD)
Buffer solution pH=2: solution of 16.66 g of $KHSO_4$ and 32.32 g of $K_2SO_4$ in 1 liter of water.
The proton nuclear magnetic resonance ($^1$H NMR) spectra are recorded in DMSO-$d_6$. The chemical shifts δ are expressed in parts per million (ppm). For the interpretation of the spectra, the following abbreviations are used: s: singlet, d:

doublet, t: triplet, q: quadruplet, up: unresolved peak, mt: multiplet, bs: broad singlet, rd: resolved doublet, spt: septuplet.

The compounds according to the invention are analyzed by LC/UV/MS (liquid chromatography/UV detection/mass spectrometry) coupling. The molecular peak (MH$^+$) and the retention time (tr) are measured in minutes.

Method 1: M1
A Symmetry C18 column of 2.1×50 mm, 3.5 µm, is used at 30° C., flow rate 0.4 ml/minute.
The eluent is composed as follows:
solvent A: 0.005% of trifluoroacetic acid (TFA) in water at pH 3.15;
solvent B: 0.005% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=210 nm-220 nm and the mass detection is carried out in the positive ESI chemical ionization mode in order to observe the ions derived from the protonation of the compounds analyzed (MH$^+$).

Method 2: M2
An XTerra MS C18 column of 2.1×50 mm, 3.5 µm, is used at 30° C., flow rate 0.4 ml/minute.
The eluent is composed as follows:
solvent A: 10 mM AcONH$_4$ at pH=7;
solvent B: acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=220 nm and the mass detection is carried out in the positive ESI chemical ionization mode in order to observe the ions derived from the protonation of the compounds analyzed (MH$^+$).

Method 3: M3
A Varian C18 column of 2×100 mm, 3.5 µm, is used at a flow rate of 0.3 ml/minute.
The eluent is composed as follows:
solvent A: 10 mM AcONH$_4$ at pH=6.5;
solvent B: acetonitrile.
Gradient:

| Time (min) | % A | % B |
|---|---|---|
| 0 | 95 | 5 |
| 25 | 10 | 90 |
| 30 | 10 | 90 |
| 32 | 95 | 5 |
| 40 | 95 | 5 |

The UV detection is carried out at λ=220 nm and the mass detection is carried out in the positive ESI chemical ionization mode in order to observe the ions derived from the protonation of the compounds analyzed (MH⁺).

Method 4: M4

An XTerra C18 column of 2.1×50 mm, 3.5 μm, is used at 30° C., flow rate 0.3 ml/minute.

The eluent is composed as follows:
solvent A: 0.005% of trifluoroacetic acid in water;
solvent B: acetonitrile.
Gradient

| Time (min) | % A | % B |
|---|---|---|
| 0 | 95 | 5 |
| 17 | 10 | 90 |
| 22 | 10 | 90 |
| 23 | 95 | 5 |
| 30 | 95 | 5 |

The UV detection is carried out at λ=220 nm and the mass detection is carried out in the positive ESI chemical ionization mode in order to observe the ions derived from the protonation of the compounds analyzed (MH⁺).

Method 5: M5

A Symmetry C18 column of 2.1×50 mm, 3.5 μm, is used at a flow rate of 0.4 ml/minute.

The eluent is composed as follows:
solvent A: 0.005% of trifluoroacetic acid in water;
solvent B: 0.005% of trifluoroacetic acid in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is carried out at λ=220 nm and the mass detection is carried out in the positive ESI chemical ionization mode in order to observe the ions derived from the protonation of the compounds analyzed (MH⁺).

Method 6: M6

A Symmetry C18 column of 2.1×50 mm, 3.5 μm, is used at a flow rate of 0.4 ml/minute.

The eluent is composed as follows:
solvent A: 0.005% of trifluoroacetic acid in water at pH=3.1;
solvent B: 0.005% of trifluoroacetic acid in acetonitrile.
Gradient:

| Time (min) | % A | % B |
|---|---|---|
| 0 | 100 | 0 |
| 20 | 10 | 90 |
| 30 | 10 | 90 |
| 31 | 100 | 0 |
| 35 | 100 | 0 |

The UV detection is carried out at λ=210-220 nm and the mass detection is carried out in the positive ESI chemical ionization mode in order to observe the ions derived from the protonation of the compounds analyzed (MH⁺).

PREPARATIONS

1. Preparation of the Compounds of Formula (XIII)

Preparation 1.1

2,4-Dichloro-N-methoxy-N-methylbenzamide (XIII)

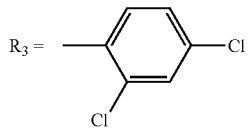

A mixture of 32.6 g of N-methoxymethanamine hydrochloride and 91.2 ml of triethylamine in 500 ml of DCM is cooled in an ice bath, and then 47 ml of 2,4-dichlorobenzoyl chloride are added slowly and the mixture is left to stir while allowing the temperature to rise to AT. After stirring for 1 hour at AT, water is added to the reaction mixture, the mixture is extracted with DCM, the organic phase is dried over Na₂SO₄ and the solvent is evaporated under vacuum. 53 g of the expected compound are obtained.

Preparation 1.2

4-Chloro-N-methoxy-N-methylbenzamide (XIII)

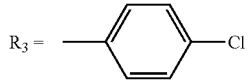

31.2 g of N-methoxymethanamine hydrochloride and 91.2 ml of triethylamine in 500 ml of DCM is cooled in an ice bath, and then 56 g of 4-chlorobenzoyl chloride are added slowly and the mixture is left to stir at AT for 4 hours. A mixture of ice/water is added, the mixture is extracted with DCM, the organic phase is washed with a buffer solution pH=2 and dried over Na₂SO₄, and the solvent is evaporated off under vacuum. 60 g of the expected compound are obtained.

Preparation 1.3

2-Chloro-N-methoxy-N-methylbenzamide (XIII)

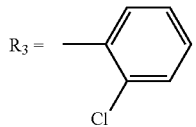

50 ml of 2-chlorobenzoyl chloride are added slowly to a mixture of 37.33 g of N-methoxymethanamine hydrochloride and 104 ml of triethylamine in 500 ml of DCM and the mixture is left to stir overnight at AT. Water is added to the reaction mixture, the mixture is extracted with DCM, the organic phase is washed with a buffer solution pH=2 and dried over Na$_2$SO$_4$, and the solvent is evaporated off under vacuum. 78.57 g of the expected compound are obtained.

2. Preparations of the Compounds of Formula (IX)

Preparation 2.1

6-(2,4-Dichlorophenyl)-4-hydroxy-2H-pyran-2-one (IX)

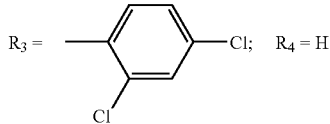

A suspension of 5.8 g of sodium hydride at 60% in oil, in 300 ml of THF, is cooled to 0° C. under a nitrogen atmosphere, then 18.9 g of ethyl 3-oxobutanoate are added slowly and the mixture is left to stir at 0° C. for 5 minutes. 97 ml of a 1.5 M solution of lithium diisopropylamide mono(tetrahydrofuran) in cyclohexane is then added dropwise at 0° C. and the mixture is left to stir at 0° C. for 20 minutes. Finally, 34 g of the compound of Preparation 1.1 are added slowly and the mixture is left to stir while allowing the temperature to return to AT and stirred overnight at AT. A mixture of ice/HCl at 10% is added, the reaction mixture is extracted with EtOAc, the organic phase is dried over Na$_2$SO$_4$ and the solvent is evaporated off under vacuum. The residue is taken up with 300 ml of concentrated H$_2$SO$_4$ and the mixture is left to stir at AT for 4 hours. The reaction mixture is poured onto ice and left to stir, and the precipitate formed is spin-filter-dried and washed with iso ether and then with pentane. 26 g of the expected compound are obtained after drying.

Preparation 2.2

6-(4-Chlorophenyl)-4-hydroxy-5-methyl-2H-pyran-2-one (IX)

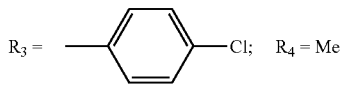

A suspension of 4.7 g of sodium hydride at 60% in oil, in 100 ml of THF, is cooled to 0° C. under a nitrogen atmosphere, a solution of 17 g of ethyl 3-oxopentanoate in 100 ml of THF is then added slowly, and the mixture is left to stir at 0° C. for 5 minutes. 86.5 ml of a 1.5 M solution of lithium diisopropylamide mono(tetrahydrofuran) in cyclohexane is then added dropwise at 0° C., and the mixture is left to stir at 0° C. for 20 minutes. Finally, a solution of 23.5 g of the compound of Preparation 1.2 in 50 ml of THF is added slowly and the mixture is left to stir while allowing the temperature to return to AT, and stirred overnight at AT. A mixture of ice/HCl at 10% is added, the reaction mixture is extracted with EtOAc, the organic phase is dried over Na$_2$SO$_4$, and the solvent is evaporated off under vacuum. The residue is taken up with 150 ml of concentrated H$_2$SO$_4$ and the mixture is left to stir at AT for 3 hours. The reaction mixture is poured onto ice and left to stir, and the precipitate formed is spin-filter-dried and washed with iso ether and then with pentane. 25 g of the expected compound are obtained after drying.

Preparation 2.3

6-(2,4-Dichlorophenyl)-4-hydroxy-5-methoxy-2H-pyran-2-one (IX)

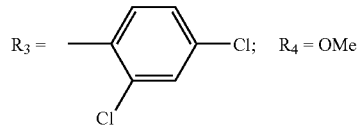

A suspension of 6 g of sodium hydride at 60% in oil, in 300 ml of THF, is cooled to 0° C. under a nitrogen atmosphere, a solution of 21.9 g of methyl 4-methoxy-3-oxobutanoate in 100 ml of THF is added slowly and the mixture is left to stir at 0° C. for 5 minutes. 100 ml of a 1.5 M solution of lithium diisopropylamide mono(tetrahydrofuran) in cyclohexane are then added dropwise and at 0° C. and the mixture is left to stir at 0° C. for 2 hours. Finally, a solution of 35.11 g of the compound of Preparation 1.1 in 100 ml of THF is added slowly and the mixture is left to stir while allowing the temperature to return to AT, and stirred overnight at AT. The reaction mixture is concentrated under vacuum, the residue is taken up in a mixture of water/HCl at 10%, the mixture is extracted with EtOAc, the organic phase is dried over Na$_2$SO$_4$, and the solvent is evaporated off under vacuum. The residue is taken up with 200 ml of concentrated H$_2$SO$_4$ and the mixture is left to stir at AT for 3 hours. The reaction mixture is poured onto ice, the mixture is extracted with DCM, the organic phase is dried over Na$_2$SO$_4$, and the solvent is evaporated off under vacuum. The residue is dissolved in a 10% K$_2$CO$_3$ solution, the solution is washed with ether, the aqueous phase is acidified by the addition of a 10% HCl solution, and the crystalline product formed is spin-filter-dried. 8.5 g of the expected compound are obtained after drying.

Preparation 2.4

6-(2-Chlorophenyl)-4-hydroxy-2H-pyran-2-one (IX)

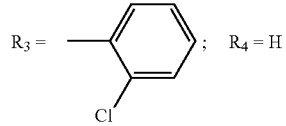

A suspension of 6 g of sodium hydride at 60% in oil, in 50 ml of THF, is cooled to 0° C. under a nitrogen atmosphere and then 19.18 ml of ethyl 3-oxobutanoate are added slowly and the mixture is left to stir at 0° C. for 5 minutes. 100 ml of a 1.5M solution of lithium diisopropylamide mono(tetrahydrofuran) in cyclohexane are then added dropwise at 0° C., and the mixture is left to stir at 0° C. for 20 minutes. Finally, 34 g of the compound of Preparation 1.3 are added slowly, and the mixture is left to stir while allowing the temperature to return to AT, and stirred for 48 hours at AT. A mixture of ice/buffer pH=2 is added, the reaction mixture is extracted with EtOAc, the organic phase is dried over Na$_2$SO$_4$, and the solvent is evaporated off under vacuum. The residue is taken up with 140 ml of concentrated $H_2SO_4$ and the mixture is left to stir at AT for 4 hours. The reaction mixture is poured onto ice, the mixture is left to stir, and the precipitate formed is spin-filter-dried and washed with iso ether and then with pentane. 28.44 g of the expected compound are obtained after drying.

3. Preparations of the Compounds of Formula (VIII)

Preparation 3.1

1-(4-Chlorophenyl)-6-(2,4-dichlorophenyl)-4-oxo-1,4-dihydropyridazine-3-carboxylic acid (VIII)

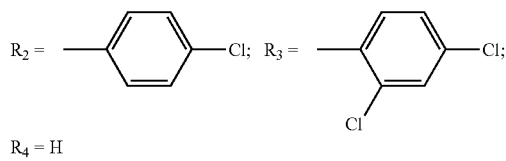

$R_4 = H$ 300 ml of concentrated HCl are added to a solution of 34.7 g of 4-chloroaniline in 70 ml of acetic acid, the mixture is cooled to 0° C., a solution of 18.8 g of sodium nitrite in 60 ml of water is added slowly and the mixture is left to stir at 0° C. for 1 hour 30 minutes so as to obtain a solution of diazonium chloride. In parallel, a solution of 70 g of the compound of Preparation 2.1 and 420 g of $Na_2CO_3$ in 500 ml of water is left to stir, the cold diazonium chloride solution is added slowly and the mixture is left to stir at AT for 2 hours. The precipitate formed is spin-filter-dried and washed with iso ether and then with pentane. The precipitate is taken up in 1 liter of concentrated HCl and the mixture is left to stir for 1 hour at AT and refluxed for 5 hours. After cooling of the reaction mixture, 2 liters of water are added, the mixture is left to stir at AT overnight, and the precipitate formed is spin-filter-dried and washed with iso ether and then with pentane. 27.8 g of the expected compound are obtained.

Preparation 3.2

1-(4-Bromophenyl)-6-(2,4-dichlorophenyl)-4-oxo-1,4-dihydropyridazine-3-carboxylic acid (VIII)

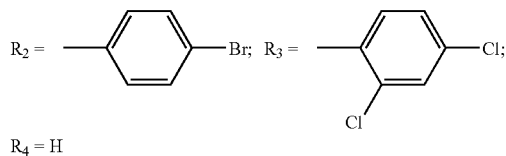

$R_4 = H$ 200 ml of concentrated HCl are added to a solution of 17.4 g of 4-bromoaniline in 50 ml of acetic acid, the mixture is cooled to 0° C., a solution of 7 g of sodium nitrite in 30 ml of water is added slowly and the mixture is left to stir at 0° C. for 1 hour 30 minutes so as to obtain a solution of diazonium chloride. In parallel, a solution of 36 g of the compound of Preparation 2.1 and 200 g of $Na_2CO_3$ in 300 ml of water and 100 ml of THF is left to stir, the cold diazonium chloride solution is added slowly and the mixture is left to stir at AT for 2 hours. The precipitate formed is spin-filter-dried and washed with iso ether and then with pentane. The precipitate is taken up in 300 ml of concentrated HCl, and the mixture is left to stir at AT for 1 hour and refluxed for 4 hours. After cooling of the reaction mixture, 2 liters of water are added, the mixture is left to stir at AT overnight, and the precipitate formed is spin-filter-dried and washed with iso ether and then with pentane. 18 g of the expected compound are obtained.

Preparation 3.3

6-(2,4-Dichlorophenyl)-1-[4-(methylthio)phenyl])-4-oxo-1,4-dihydropyridazine-3-carboxylic acid (VIII)

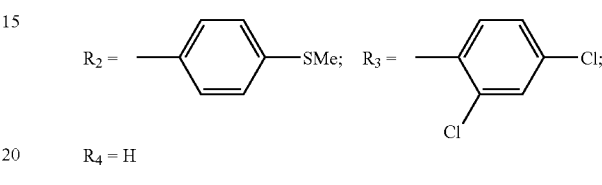

$R_4 = H$ 200 ml of concentrated HCl are added to a solution of 19.8 g of 4-(methylthio)aniline in 50 ml of acetic acid, the mixture is cooled to 0° C., a solution of 9.9 g of sodium nitrite in 30 ml of water is added slowly, and the mixture is left to stir at 0° C. for 2 hours so as to obtain a solution of diazonium chloride. In parallel, a solution of 35.8 g of the compound of Preparation 2.1 and 650 g of $Na_2CO_3$ in 650 ml of water and 250 ml of THF is left to stir, the cold diazonium chloride solution is added slowly and the mixture is left to stir at AT for 2 hours. The precipitate formed is spin-filter-dried and washed with iso ether and then with pentane. The precipitate is taken up in 700 ml of concentrated HCl and the mixture is left to stir at AT overnight and refluxed for 1 hour. After cooling of the reaction mixture, 1.5 liters of water are added, the mixture is left to stir at AT overnight and the precipitate formed is spin-filter-dried and washed with iso ether and then with pentane. 41.7 g of the expected compound are obtained.

Preparation 3.4

6-(4-Chlorophenyl)-1-(2,4-dichlorophenyl)-5-methyl-4-oxo-1,4-dihydro-pyridazine-3-carboxylic acid (VIII)

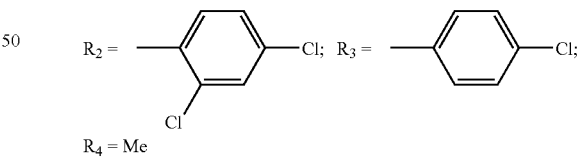

$R_4 = Me$ 120 ml of concentrated HCl are added to a solution of 17.1 g of 2,4-dichloroaniline in 20 ml of acetic acid, the mixture is cooled to 0° C., a solution of 7.3 g of sodium nitrite in 30 ml of water is added slowly and the mixture is left to stir at 0° C. for 1 hour so as to obtain a solution of diazonium chloride. In parallel, a solution of 25 g of the compound of Preparation 2.2, 100 g of $Na_2CO_3$ and 30 ml of concentrated NaOH in 200 ml of EtOH and 200 ml of water is left to stir, the cold diazonium chloride solution is added slowly and the mixture is left to stir at AT for 1 hour. The precipitate formed is spin-filter-dried and washed with iso ether and then with pentane. The precipitate is taken up in 300 ml of concentrated HCl and the mixture is left to stir at AT for 30 minutes and refluxed for 3 hours. After cooling of the reaction mixture to AT, the precipitate formed is spin-filter-dried and washed with water. 16.5 g of the expected compound are obtained after drying.

Preparation 3.5

1-(4-Chlorophenyl)-6-(2,4-dichlorophenyl)-5-methoxy-4-oxo-1,4-dihydro-pyridazine-3-carboxylic acid (VIII)

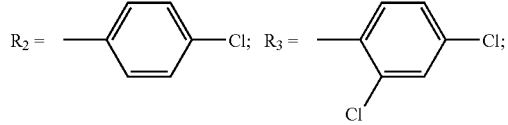

$R_4$ = OMe 60 ml of concentrated HCl are added to a solution of 5.8 g of 4-chloroaniline in 20 ml of acetic acid, the mixture is cooled to 0° C., a solution of 3.2 g of sodium nitrite in 10 ml of water is added slowly and the mixture is left to stir at 0° C. for 2 hours so as to obtain a solution of diazonium chloride. In parallel, a solution of 13 g of the compound of Preparation 2.3 and 150 g of $Na_2CO_3$ in 200 ml of water is left to stir, the cold diazonium chloride solution is added slowly and the mixture is left to stir at AT for 2 hours. The precipitate formed is spin-filter-dried and washed with iso ether and then with pentane. The precipitate is taken up in 200 ml of concentrated HCl, the mixture is left to stir at AT overnight, and the precipitate formed is spin-filter-dried and washed with iso ether and then with pentane. 16 g of the expected compound are obtained after drying.

By following the protocols described in Preparations 3, the compounds of formula (VIII) given in TABLE I hereinafter are prepared:

TABLE I

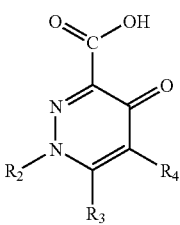
(VIII)

| Preparations | $R_2$ | $R_3$ | $R_4$ |
|---|---|---|---|
| 3.6 | 4-F-C6H4 | 2,4-diCl-C6H3 | H |
| 3.7 | 4-Cl-C6H4 | 2-Cl-C6H4 | H |
| 3.8 | 4-OMe-C6H4 | 2,4-diCl-C6H3 | H |
| 3.9 | 4-F-C6H4 | 2-Cl-C6H4 | H |
| 3.10 | 4-OMe-C6H4 | 2-Cl-C6H4 | H |
| 3.11 | 4-SMe-C6H4 | 2-Cl-C6H4 | H |
| 3.12 | 4-Cl-C6H4 | 2-Cl-4-F-C6H3 | H |

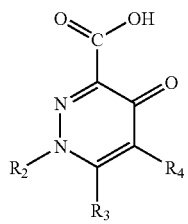

TABLE I-continued (VIII)

Structure: pyridazine carboxylic acid with R2 on N, R3 and R4 on ring carbons.

| Preparations | R2 | R3 | R4 |
|---|---|---|---|
| 3.13 | 4-SMe-phenyl | 2-Cl,4-Cl-phenyl | OMe |
| 3.14 | 4-SMe-phenyl | 2-Cl,4-F-phenyl | H |
| 3.15 | 4-SMe-phenyl | 2-Cl,4-Br-phenyl | H |
| 3.16 | 4-SMe-phenyl | 2-Cl,4-OMe-phenyl | H |
| 3.17 | 4-SMe-phenyl | 2-Cl,4-SMe-phenyl | H |
| 3.18 | 4-OCF3-phenyl | 2-Cl,4-Cl-phenyl | H |
| 3.19 | 4-SCF3-phenyl | 2-Cl,4-Cl-phenyl | H |

4. Preparations of the Compounds of Formula (VI)

Preparation 4.1

Methyl 1-(4-chlorophenyl)-6-(2,4-dichlorophenyl)-4-oxo-1,4-dihydropyridazine-3-carboxylate (VI)

R2 = 4-chlorophenyl; R3 = 2,4-dichlorophenyl;

R4 = H

A mixture of 27.8 g of the compound of Preparation 3.1 and 30 ml of triethylamine in 200 ml of DCM and 100 ml of THF is cooled in an ice bath, 6.14 ml of isocyanatosulfuryl chloride are added, and the mixture is left to stir at 0° C. for 30 minutes and then allowed to return to AT. 300 ml of MeOH are then added, the mixture is refluxed for 1 hour, 10 ml of triethylamine are added and the refluxing is continued for 2 hours. The reaction mixture is concentrated under vacuum, the residue is taken up in an ice/water mixture, the mixture is acidified to pH=3 by the addition of 2N HCl and extracted with DCM, the organic phase is dried over Na$_2$SO$_4$, and the solvent is evaporated off under vacuum. 26.5 g of the expected compound are obtained.

Preparation 4.2

Methyl 1-(4-bromophenyl)-6-(2,4-dichlorophenyl)-4-oxo-1,4-dihydropyridazine-3-carboxylate (VI)

R2 = 4-bromophenyl; R3 = 2,4-dichlorophenyl;

R4 = H

A mixture of 18 g of the compound of Preparation 3.2 in 200 ml of DCM and 150 ml of THF is cooled in an ice bath, 3.57 ml of isocyanatosulfuryl chloride and then 5.85 ml of triethylamine are added, and the mixture is left to stir at 0° C. for 30 minutes and then allowed to return to AT. 300 ml of MeOH and 10 ml of triethylamine are then added and the mixture is heated at 100° C. for 3 hours. The reaction mixture is concentrated under vacuum, the residue is taken up with water, the mixture is acidified to pH=3 by the addition of 2N HCl and extracted with DCM, the organic phase is dried over Na$_2$SO$_4$, and the solvent is evaporated off under vacuum. The residue is chromatographed on silica gel, elution being carried out with a mixture of DCM/propan-2-ol (100/2; v/v). 8 g of the expected compound are obtained after crystallization from a mixture of EtOH/iso ether.

Preparation 4.3

Methyl 6-(2,4-dichlorophenyl)-1-[4-(methylthio)phenyl]-4-oxo-1,4-dihydro-pyridazine-3-carboxylate (VI)

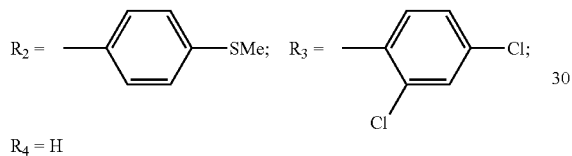

R$_4$ = H

A mixture of 36.14 g of the compound of Preparation 3.3 in 300 ml of DCM and 100 ml of THF is cooled to 0° C., 37 ml of triethylamine and then 7.88 ml of isocyanatosulfuryl chloride are added, and the mixture is left to stir at 0° C. for 30 minutes and then allowed to return to AT. 350 ml of MeOH are then added, the mixture is refluxed for 1 hour, 35 ml of triethylamine are added, and the refluxing is continued for 2 hours. The reaction mixture is concentrated under vacuum, the residue is taken up with an ice/water mixture, the mixture is acidified to pH=3 by the addition of a buffer solution pH=2, and extracted with DCM, the organic phase is dried over Na$_2$SO$_4$, and the solvent is evaporated off under vacuum. 30.6 g of the expected compound are obtained.

Preparation 4.4

Methyl 6-(4-chlorophenyl)-1-(2,4-dichlorophenyl)-5-methyl-4-oxo-1,4-dihydro-pyridazine-3-carboxylate (VI)

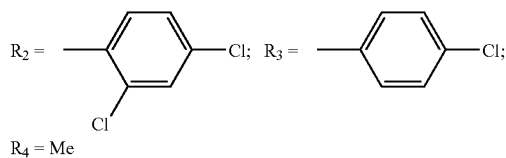

R$_4$ = Me

A mixture of 15 g of the compound of Preparation 3.4 in 150 ml of DCM and 50 ml of THF is cooled to 0° C., 3.20 ml of isocyanatosulfuryl chloride and then 5.15 ml of triethylamine are added, and the mixture is left to stir at 0° C. for 2 hours. 400 ml of MeOH and 25 ml of triethylamine are then added and the mixture is refluxed for 3 hours. The reaction mixture is concentrated under vacuum, the residue is taken up with an ether/EtOH mixture, and the crystalline compound formed is spin-filter-dried, washed with pentane and dried. 15 g of the expected compound are obtained.

Preparation 4.5

Methyl 1-(4-chlorophenyl)-6-(2,4-dichlorophenyl)-5-methoxy-4-oxo-1,4-dihydro-pyridazine-3-carboxylate (VI)

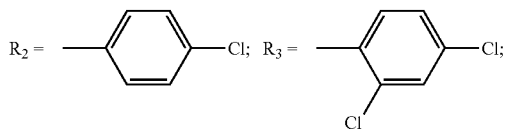

R$_4$ = OMe

A mixture of 8 g of the compound of Preparation 3.5 in 150 ml of DCM and 150 ml of THF is cooled to 0° C., 8 ml of triethylamine and then 1.64 ml of isocyanatosulfuryl chloride are added, and the mixture is left to stir at 0° C. for 30 minutes and then allowed to return to AT. 200 ml of MeOH are then added and the mixture is refluxed for 2 hours. The reaction mixture is concentrated under vacuum, the residue is taken up with water and the precipitate formed is spin-filter-dried and dried. 7.4 g of the expected compound are obtained.

By following the protocols described in Preparations 4, the compounds of formula (VI) given in TABLE II below are prepared:

TABLE II

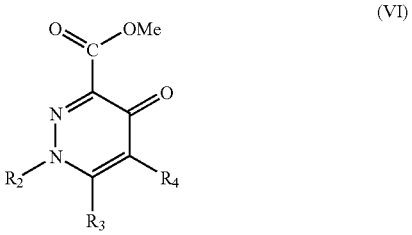

| Preparations | R$_2$ | R$_3$ | R$_4$ |
|---|---|---|---|
| 4.6 | 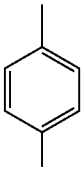 | 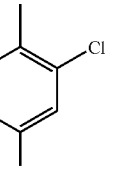 | H |

TABLE II-continued
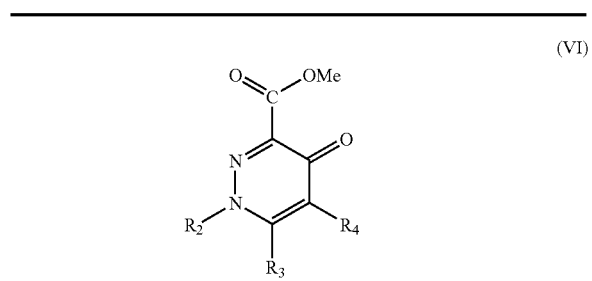
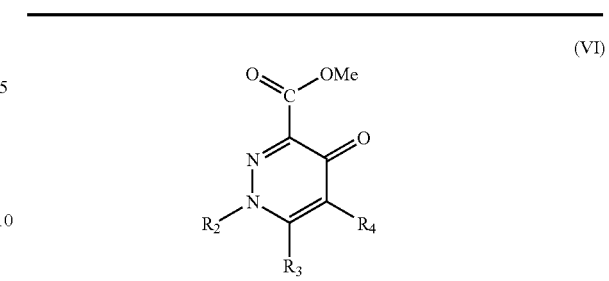

TABLE II-continued

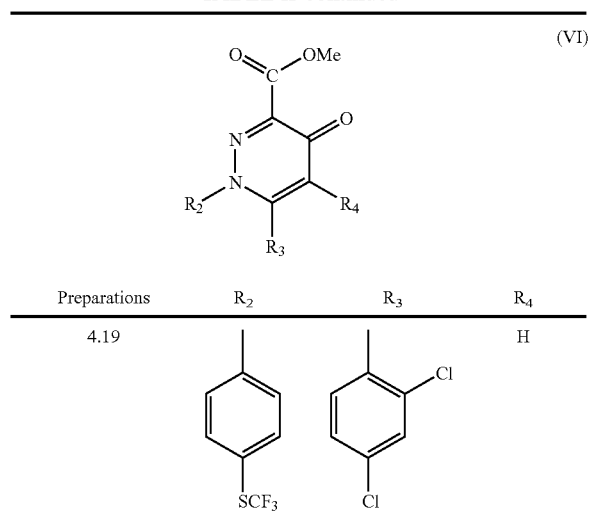

| Preparations | $R_2$ | $R_3$ | $R_4$ |
|---|---|---|---|
| 4.19 | 4-SCF$_3$-phenyl | 2,4-Cl$_2$-phenyl | H |

5. Preparations of the Compounds of Formula (IV)

Preparation 5.1

1-(4-Chlorophenyl)-6-(2,4-dichlorophenyl)-4-oxo-1,4-dihydropyridazine-3-carbohydrazide hydrochloride (IV, HCl)

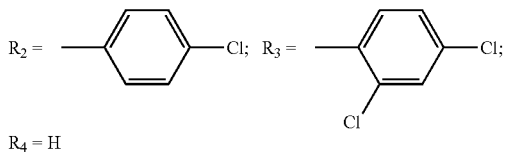

$R_4 = H$

A mixture of 26.5 g of the compound of Preparation 4.1 and 5.5 ml of hydrazine monohydrate in 400 ml of dioxane is left to stir at AT for 3 hours. The reaction mixture is concentrated under vacuum, the residue is taken up with 100 ml of EtOH, 100 ml of 2N hydrochloric ether and then 200 ml of ether are added, the mixture is left to stir and the precipitate formed is spin-filter-dried. 23 g of the expected compound are obtained.

Preparation 5.2

1-(4-Bromophenyl)-6-(2,4-dichlorophenyl)-4-oxo-1,4-dihydropyridazine-3-carbohydrazide (IV)

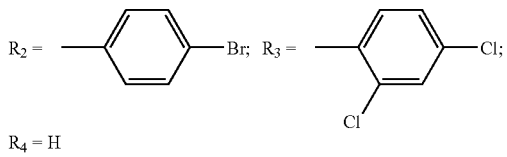

$R_4 = H$

A mixture of 8 g of the compound of Preparation 4.2 and 3 ml of hydrazine monohydrate in 150 ml of dioxane is left to stir at AT for 3 hours. The reaction mixture is concentrated under vacuum, the residue is taken up in ether, the mixture is left to stir at AT overnight and the precipitate formed is spin-filter-dried. 5.5 g of the expected compound are obtained.

Preparation 5.3

6-(2,4-Dichlorophenyl)-1-[4-(methylthio)phenyl]-4-oxo-1,4-dihydropyridazine-3-carbohydrazide hydrochloride (IV, HCl)

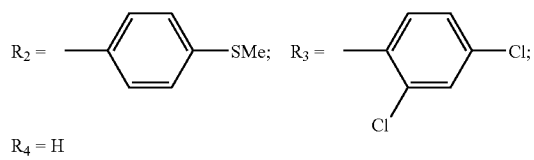

$R_4 = H$

A mixture of 30.6 g of the compound of Preparation 4.3 and 7 ml of hydrazine monohydrate in 400 ml of dioxane is left to stir at AT for 2 hours. The reaction mixture is concentrated under vacuum, the residue is taken up with 100 ml of EtOH, 100 ml of 2N hydrochloric ether and then 200 ml of ether are added, the mixture is left to stir and the precipitate formed is spin-filter-dried. 32 g of the expected compound are obtained.

Preparation 5.4

6-(4-Chlorophenyl)-1-(2,4-dichlorophenyl)-5-methyl-4-oxo-1,4-dihydro-pyridazine-3-carbohydrazide (IV)

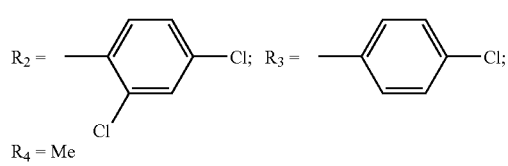

$R_4 = Me$

A mixture of 15 g of the compound of Preparation 4.4 and 7 ml of hydrazine monohydrate in 400 ml of dioxane and 300 ml of DCM is left to stir at AT for 24 hours. The reaction mixture is concentrated under vacuum, the residue is taken up in an ether/EtOH mixture, and the precipitate formed is spin-filter-dried and dried. 11.5 g of the expected compound are obtained.

Preparation 5.5

1-(4-Chlorophenyl)-6-(2,4-dichlorophenyl)-5-methoxy-4-oxo-1,4-dihydro-pyridazine-3-carbohydrazide hydrochloride (IV, HCl):

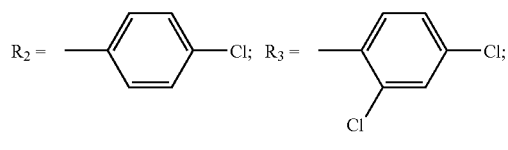

$R_4 = OMe$

A mixture of 7.4 g of the compound of Preparation 4.5 and 1 g of hydrazine monohydrate in 200 ml of dioxane and 50 ml of MeOH is left to stir at AT for 16 hours. The reaction mixture is concentrated under vacuum, the residue is taken up in 50 ml of EtOH, 2N hydrochloric ether and then iso ether are added, and the precipitate formed is spin-filter-dried, washed with iso ether and then with pentane and dried. 8.2 g of the expected compound are obtained.

By following the protocols described in Preparations 5, the compounds of formula (IV) given in TABLE III below are prepared:

TABLE III

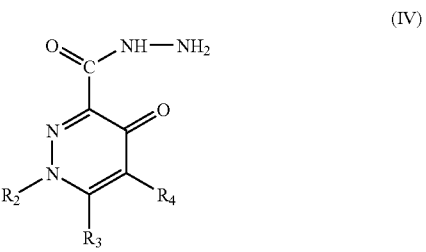

| Preparations | $R_2$ | $R_3$ | $R_4$ |
|---|---|---|---|
| 5.6 (HCl) | 4-F-phenyl | 2,4-diCl-phenyl | H |
| 5.7 (HCl) | 4-Cl-phenyl | 2-Cl-phenyl | H |
| 5.8 (HCl) | 4-OMe-phenyl | 2,4-diCl-phenyl | H |
| 5.9 (HCl) | 4-F-phenyl | 2-Cl-phenyl | H |
| 5.10 (HCl) | 4-OMe-pyridyl | 2-Cl-phenyl | H |
| 5.11 (HCl) | 4-SMe-phenyl | 2-Cl-phenyl | H |
| 5.12 (HCl) | 4-Cl-phenyl | 3-Cl-4-F-phenyl | H |
| 5.13 (HCl) | 4-SMe-phenyl | 3,4-diCl-phenyl | OMe |
| 5.14 (HCl) | 4-SMe-phenyl | 3-Cl-4-F-phenyl | H |
| 5.15 (HCl) | 4-SMe-phenyl | 3-Cl-4-Br-phenyl | H |
| 5.16 (HCl) | 4-SMe-phenyl | 3-Cl-4-OMe-phenyl | H |

TABLE III-continued

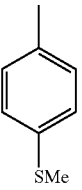

| Preparations | R$_2$ | R$_3$ | R$_4$ |
|---|---|---|---|
| 5.17(HCl) | 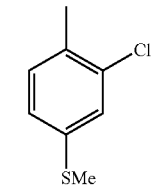 4-SMe-phenyl | 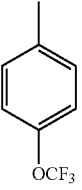 2-Cl,4-SMe-phenyl | H |
| 5.18(HCl) | 4-OCF$_3$-phenyl | 2,4-diCl-phenyl | H |
| 5.19(HCl) | 4-SCF$_3$-phenyl | 2,4-diCl-phenyl | H |

6. Preparations of the compounds of formula (II)

Preparation 6.1

5-(4-Chlorophenyl)-6-(2,4-dichlorophenyl)-2,5-dihydro-3H-pyrazolo[4,3-c]-pyridazin-3-one (II)

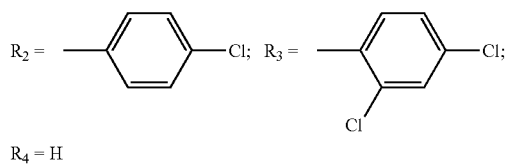

R$_4$ = H

A mixture of 5 g of the compound of Preparation 5.1 and 500 ml of pyridine is heated at 135° C. for 36 hours. The reaction mixture is concentrated under vacuum, the residue is taken up with water, the mixture is left to stir at AT overnight, and the precipitate formed is spin-filter-dried and dried. 3.5 g of the expected compound are obtained.

Preparation 6.2

5-(4-Bromophenyl)-6-(2,4-dichlorophenyl)-2,5-dihydro-3H-pyrazolo[4,3-c]-pyridazin-3-one (II)

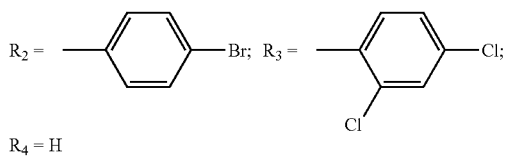

R$_4$ = H

A mixture of 5.5 g of the compound of Preparation 5.2, 500 ml of pyridine and 10 ml of concentrated HCl is heated at 120° C. overnight. The reaction mixture is concentrated under vacuum, the residue is taken up with water, and the precipitate formed is spin-filter-dried and dried. 5 g of the expected compound are obtained.

Preparation 6.3

6-(2,4-Dichlorophenyl)-5-[4-(methylthio)phenyl]-2,5-dihydro-3H-pyrazolo-[4,3-c]pyridazin-3-one (II)

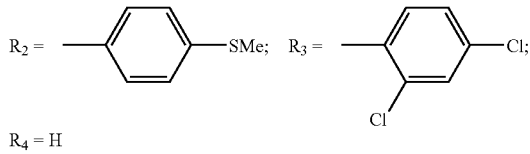

R$_4$ = H

A mixture of 5 g of the compound of Preparation 5.3 and 486 ml of pyridine is refluxed for 72 hours. The reaction mixture is concentrated under vacuum, the residue is taken up with water, the mixture is left to stir at AT for 1 hour, and the precipitate formed is spin-filter-dried (4.31 g). 0.2 g of precipitate is chromatographed on silica H gel, elution being carried out with DCM and then with a DCM/MeOH mixture (100/2.5; v/v). 0.07 g of the expected compound is obtained.

Preparation 6.4

6-(4-Chlorophenyl)-5-(2,4-dichlorophenyl)-7-methyl-2,5-dihydro-3H-pyrazolo-[4,3-c]pyridazin-3-one (II)

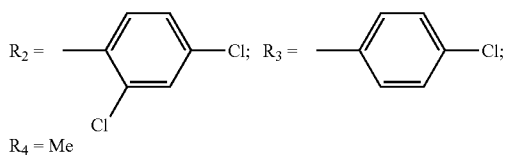

R$_4$ = Me

A mixture of 5.2 g of the compound of Preparation 4.4, 50 ml of pyridine and 2 ml of concentrated HCl is refluxed for 3 days. After cooling to AT, water is added to the reaction mixture and the precipitate formed is spin-filter-dried. The precipitate is dissolved in EtOAc and an insoluble product is filtered off. The aqueous spin-filter-drying liquors are extracted with EtOAc, the organic phase is washed with a 10% HCl solution, the combined organic phases are dried over Na$_2$SO$_4$, and the solvent is evaporated off under vacuum. 2.3 g of the expected compound are obtained.

Preparation 6.5

5-(4-Chlorophenyl)-6-(2,4-dichlorophenyl)-7-methoxy-2,5-dihydro-3H-pyrazolo-[4,3-c]pyridazin-3-one (II)

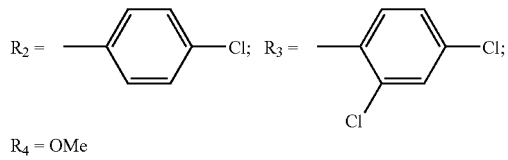

R$_4$ = OMe

A mixture of 3.6 g of the compound of Preparation 5.5 and 1.7 g of potassium tert-butoxide in 400 ml of EtOH is refluxed for 4 hours. The reaction mixture is concentrated under vacuum, the residue is taken up with a 10% HCl solution, and the precipitate formed is spin-filter-dried and washed with iso ether and then with pentane. 2.5 g of the expected compound are obtained.

By following the protocols described in Preparations 6, the compounds of formula (II) given in TABLE IV below are prepared:

TABLE IV

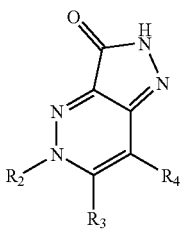

(II)

| Preparations | R$_2$ | R$_3$ | R$_4$ |
|---|---|---|---|
| 6.6 | 4-F-C$_6$H$_4$ | 2,4-Cl$_2$-C$_6$H$_3$ | H |
| 6.7 | 4-Cl-C$_6$H$_4$ | 2-Cl-C$_6$H$_4$ | H |
| 6.8 | 4-OMe-C$_6$H$_4$ | 2,4-Cl$_2$-C$_6$H$_3$ | H |
| 6.9 | 4-F-C$_6$H$_4$ | 2-Cl-C$_6$H$_4$ | H |
| 6.10 | 4-OMe-C$_6$H$_4$ | 2-Cl-C$_6$H$_4$ | H |
| 6.11 | 4-SMe-C$_6$H$_4$ | 2-Cl-C$_6$H$_4$ | H |
| 6.12 | 4-Cl-C$_6$H$_4$ | 2-Cl-4-F-C$_6$H$_3$ | H |
| 6.13 | 4-SMe-C$_6$H$_4$ | 2,4-Cl$_2$-C$_6$H$_3$ | OMe |

TABLE IV-continued (II) [pyrazolo-pyridazinone structure with R2, R3, R4 substituents]

| Preparations | R2 | R3 | R4 |
|---|---|---|---|
| 6.14 | 4-SMe-phenyl | 2-Cl-4-F-phenyl | H |
| 6.15 | 4-SMe-phenyl | 2-Cl-4-Br-phenyl | H |
| 6.16 | 4-SMe-phenyl | 2-Cl-4-OMe-phenyl | H |
| 6.17 | 4-SMe-phenyl | 2-Cl-4-SMe-phenyl | H |
| 6.18 | 4-OCF3-phenyl | 2,4-diCl-phenyl | H |
| 6.19 | 4-SCF3-phenyl | 2,4-diCl-phenyl | H |

7. Preparations of the Compounds of Formula (III)

Preparation 7.1

[4-(Trifluoromethyl)cyclohexyl]methyl methanesulfonate, mixture of cis and trans (III)

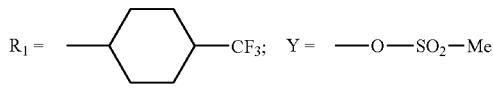

$R_1 =$ [4-(trifluoromethyl)cyclohexyl]; $Y = $ —O—SO$_2$—Me

A) [4-(Trifluoromethyl)cyclohexyl]methanol, mixture of cis and trans 65 ml of a 1M solution of borane in THF are added, dropwise and at AT, to a mixture of 5.15 g of a cis and trans mixture of 4-(trifluoromethyl)-cyclohexanecarboxylic acid in 150 ml of THF, and the mixture is left to stir at AT for 1 hour and then heated at 100° C. for 4 hours. 150 ml of MeOH are then added and the mixture is refluxed for 1 hour. Finally, 100 ml of 2N hydrochloric ether are added, dropwise, and the mixture is refluxed for 45 minutes. After cooling to AT, the reaction mixture is concentrated under vacuum, the residue is taken up with a 10% NaOH solution, the mixture is left to stir for 30 minutes and extracted with EtOAc, the organic phase is dried over Na$_2$SO$_4$, and the solvent is evaporated off under vacuum. 4.35 g of the expected compound are obtained.

B) [4-(Trifluoromethyl)cyclohexyl]methyl methanesulfonate, mixture of cis and trans A mixture of 4.35 g of the compound of stage A and 5.1 ml of triethylamine in 50 ml of DCM is cooled to 0° C., 1.85 ml of methanesulfonyl chloride are added dropwise and the mixture is left to stir while allowing the temperature to return to AT. After stirring at AT for 4 hours, ice is added to the reaction mixture, the mixture is extracted with DCM, the organic phase is dried over Na$_2$SO$_4$, and the solvent is evaporated off under vacuum. 4 g of the expected compound are obtained in the form of an oil.

Preparation 7.2

Adamant-1-ylmethyl methanesulfonate (III)

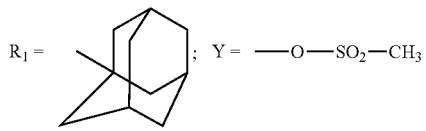

$R_1 =$ [adamantyl]; $Y = $ —O—SO$_2$—CH$_3$

A mixture of 3 g of adamantan-1-ylmethanol and 5 ml of triethylamine in 50 ml of DCM is cooled to 0° C., 2 ml of methanesulfonyl chloride are added dropwise, and the mixture is left to stir while allowing the temperature to return to AT. A mixture of water/ice is added to the reaction mixture, the mixture is extracted with DCM, the organic phase is dried

Preparation 7.3

4-(Chloromethyl)-2-fluoro-1-propoxybenzene (III)

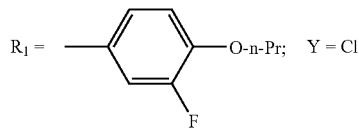

A) 3-Fluoro-4-propoxybenzoic acid

A mixture of 2 g of 3-fluoro-4-hydroxybenzoic acid and 5.31 g of $K_2CO_3$ in 50 ml of acetonitrile is refluxed for 24 hours, 0.5 ml of 1-iodopropane is added and the refluxing is continued for 7 hours. After cooling to AT, the reaction mixture is concentrated under vacuum, the residue is taken up with water, the mixture is extracted with EtOAc and the solvent is evaporated off under vacuum. The residue is taken up in 30 ml of EtOH, 5 ml of a concentrated NaOH solution are added, and the mixture is left to stir at 60° C. for 1 hour. The mixture is concentrated under vacuum, the residue is taken up with a 10% HCl solution, the mixture is extracted with DCM, the organic phase is dried over $Na_2SO_4$, and the solvent is evaporated off under vacuum. 0.8 g of the expected compound is obtained.

B) (3-Fluoro-4-propoxyphenyl)methanol 8 ml of a 1M solution of borane in THF are added, dropwise, to a mixture of 0.8 g of the compound of the preceding stage in 300 ml of THF, and the mixture is left to stir at AT for 30 minutes and then heated at 100° C. for 2 hours. 100 ml of MeOH are then added and the mixture is heated at 100° C. for 1 hour. Finally, 20 ml of 2 N hydrochloric ether are added and the mixture is heated at 100° C. for 1 hour. The reaction mixture is concentrated under vacuum, the residue is taken up with water, the mixture is extracted with DCM, the organic phase is dried over $Na_2SO_4$, and the solvent is evaporated off under vacuum. 0.8 g of the expected compound is obtained.

C) 4-(Chloromethyl)-2-fluoro-1-propoxybenzene

A mixture of 0.8 g of the compound of the preceding stage, 0.4 ml of methanesulfonyl chloride and 0.2 ml of triethylamine in 10 ml of DCM is left to stir at AT overnight. Ice is added to the reaction mixture, followed by buffer at pH=2, the mixture is extracted with DCM, the organic phase is dried over $Na_2SO_4$, and the solvent is evaporated off under vacuum. 1.2 g of the expected compound are obtained.

Preparation 7.4

N-[4-(Chloromethyl)benzyl]1-N-ethylpropan-1-amine hydrochloride (III)

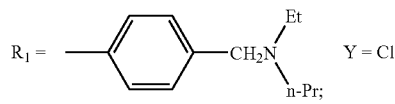

A) [4-[[ethyl(propyl)amino]methyl]phenyl]methanol

A mixture of 5 g of [4-(chloromethyl)phenyl]methanol, 5.56 g of N-ethylpropan-1-amine, 5.29 g of potassium iodide and 4.41 g of $K_2CO_3$ in 200 ml of acetonitrile is left to stir at AT for 48 hours. The reaction mixture is concentrated under vacuum, the residue is taken up with water, the mixture is extracted with DCM, the organic phase is dried over $Na_2SO_4$, and the solvent is evaporated off under vacuum. 3.5 g of the expected compound are obtained.

B) N-[4-(chloromethyl)benzyl]-N-ethylpropan-1-amine hydrochloride 2.87 g of thionyl chloride are added, dropwise, to a mixture of 0.5 g of the compound of the preceding stage in 5 ml of 2N hydrochloric ether and the mixture is left to stir at AT for 2 hours. The reaction mixture is concentrated under vacuum, the residue is taken up with DCM, and the solvent is evaporated off under vacuum. 0.6 g of the expected compound is obtained.

Preparation 7.5

N-[4-(Chloromethyl)benzyl]-2,2,2-trifluoro-N-methylethanamine hydrochloride (III)

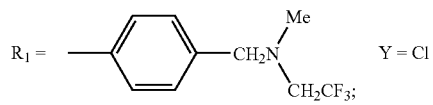

A) Methyl 4-[(methylamino)methyl]benzoate 1.13 g of NaH at 60% in oil, and then 2.35 ml of methyl iodide are added to a solution of 5 g of methyl 4-[[(tert-butoxycarbonyl)amino]methyl]benzoate in 150 ml of THF and the mixture is left to stir at AT overnight. The reaction mixture is concentrated under vacuum, the residue is taken up with a water/ice mixture, the mixture is extracted with EtOAc, the organic phase is dried over $Na_2SO_4$, and the solvent is evaporated off under vacuum. The residue is taken up with 80 ml of 2N hydrochloric ether, 1 ml of water is added, and the mixture is left to stir at AT overnight. The reaction mixture is concentrated under vacuum, the residue is taken up with a 5% $NaHCO_3$ solution, the mixture is extracted with DCM, the organic phase is dried over $Na_2SO_4$, and the solvent is evaporated off under vacuum. 2.2 g of the expected compound are obtained.

B) Methyl 4-[[methyl-(2,2,2-trifluoroethyl)amino]methylbenzoate

A mixture of 2.2 g of the compound of the preceding stage, 3.13 g of 2,2,2-tri-fluoroethyltrifluoromethanesulfonate and 2.06 g of NaHCO$_3$ in 20 ml of EtOH is heated at 80° C. for 5 hours. The reaction mixture is concentrated under vacuum, the residue is taken up with water, the mixture is extracted with DCM, the organic phase is dried over Na$_2$SO$_4$, and the solvent is evaporated off under vacuum. 2 g of the expected compound are obtained.

C) [4-[[methyl-(2,2,2-trifluoroethyl)amino]methyl]phenyl]methanol

A suspension of 0.581 g of LiAlH$_4$ in 30 ml of ether is cooled to 0° C., a solution of 2 g of the compound of the preceding stage in 10 ml of ether is added dropwise, and the mixture is left to stir while allowing the temperature to return to AT. 1.4 ml of water and then 1.4 ml of 15% NaOH and 4.4 ml of water are then added, the mixture is left to stir, and the mineral salts are filtered off. The filtrate is concentrated under vacuum, the residue is taken up with water, the mixture is extracted with ether, the organic phase is dried over Na$_2$SO$_4$, and the solvent is evaporated off under vacuum. 2 g of the expected compound are obtained.

D) N-[4-(Chloromethyl)benzyl]-2,2,2-trifluoro-N-methylethanamine hydrochloride 2 ml of thionyl chloride are added to a mixture of 0.5 g of the compound of the preceding stage in 10 ml of 2N hydrochloric ether and the mixture is left to stir at AT overnight. The reaction mixture is concentrated under vacuum and 0.5 g of the expected compound is obtained.

By following the protocols described in Preparations 7, the compounds of formula (III) given in TABLE V below are prepared:

TABLE V

| Preparations | Y—CH$_2$—R$_1$ (III) Y | R$_1$ |
|---|---|---|
| 7.6 | —O—SO$_2$—CH$_3$ | phenyl-nBu |
| 7.7 | —Cl | phenyl-O-t-Bu |
| 7.8 | —Cl | phenyl-SCF$_3$ (meta) |
| 7.9 | —Cl | —CH(nPr)$_2$ |
| 7.10 | —O—SO$_2$—CH$_3$ | cyclohexyl-t-Bu cis/trans |

TABLE V-continued

| Preparations | Y—CH$_2$—R$_1$ (III) Y | R$_1$ |
|---|---|---|
| 7.11 | —Cl | phenyl-CF$_3$ with F |
| 7.12 | —Cl | phenyl-SCF$_3$ |

Example 1

Compound No. 1

5-(4-Chlorophenyl)-2-(cyclohexylmethyl)-6-(2,4-dichlorophenyl)-2,5-dihydro-3H-pyrazolo[4,3-c]pyridazin-3-one A mixture of 0.5 g of the compound of Preparation 6.1, 0.27 ml of (bromomethyl)cyclohexane and 0.27 g of K$_2$CO$_3$ in 20 ml of dioxane and 5 ml of DMF is heated at 130° C. for 48 hours. The reaction mixture is concentrated under vacuum, the residue is taken up with water, the mixture is extracted with DCM, the organic phase is dried over Na$_2$SO$_4$, and the solvent is evaporated off under vacuum. 0.22 g is obtained after crystallization from iso ether.

MH$^+$: 487; tr=11.24 (M1);
$^1$H NMR: DMSO-d$_6$ (250 MHz): δ (ppm): 0.75-1.95: up: 11H; 3.70: mt: 2H, 7.29-7.74: up: 8H.

Example 2

Compound No. 2 and Compound No. 3

5-(4-Chlorophenyl)-6-(2,4-dichlorophenyl)-2-[[4-(trifluoromethyl)cyclohexyl]-methyl]-2,5-dihydro-3H-pyrazolo[4,3-c]pyridazin-3-one, the least polar isomer and the most polar isomer A mixture of 0.5 g of the compound of Preparation 6.1, 0.664 g of the compound of Preparation 7.1 and 0.352 g of K$_2$CO$_3$ in 20 ml of dioxane and 5 ml of DMF is heated at 130° C. for 48 hours. The reaction mixture is concentrated under vacuum, the residue is taken up with water, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/2; v/v). The two isomers are separated:

Compound No. 2: the least polar: m=0.12 g after crystallization from iso ether;
MH$^+$: 555; tr=11.45 (M1);
$^1$H NMR: DMSO-d$_6$ (500 MHz): δ (ppm): 1.42-1.72: up: 8H, 2.24: mt: 1H, 2.31: mt: 1H, 3.94: mt: 2H, 7.37-7.76: up: 8H.

Compound No. 3: the most polar: m=0.025 g after crystallization from iso ether.
MH$^+$: 555; tr=11.42 (M1);
$^1$H NMR: DMSO-d$_6$ (500 MHz): δ (ppm): 0.99-1.34: up: 4H, 1.73: mt: 2H, 1.78-1.94: up: 3H, 2.24: mt: 1H, 3.78: mt: 2H, 7.40-7.58: m: 6H.

Example 3

Compound No. 4

2-(Adamantan-1-ylmethyl)-5-(4-chlorophenyl)-6-(2,4-dichlorophenyl)-2,5-dihydro-3H-pyrazolo[4,3-c]pyridazin-3-one A mixture of 0.5 g of the compound of Preparation 6.1, 0.62 g of the compound of Preparation 7.2 and 0.624 g of $Cs_2CO_3$ in 20 ml of dioxane and 5 ml of DMF is heated at 140° C. overnight. The reaction mixture is concentrated under vacuum, the residue is taken up with water, the mixture is extracted with DCM, the organic phase is dried over $Na_2SO_4$, and the solvent is evaporated off under vacuum. The residue is chromatographed on silica gel, elution being carried out with a mixture of DCM/propan-2-ol (97/3; v/v). 0.025 g of the expected compound is obtained after crystallization from iso ether.

Example 4

Compound No. 7

5-(4-Chlorophenyl)-6-(2,4-dichlorophenyl)-2-(4-isopropylbenzyl)-2,5-dihydro-3H-pyrazolo[4,3-c]pyridazin-3-one A mixture of 0.5 g of the compound of Preparation 6.1 in 30 ml of THF and 5 ml of DMF is cooled to 0° C., 0.052 g of NaH at 60% in oil and then 0.26 ml of 4-isopropylbenzyl bromide are added, and the mixture is left to stir while allowing the temperature to return to AT. The mixture is then heated at 60° C. for 6 hours and then stirred at AT overnight. The reaction mixture is concentrated under vacuum, the residue is taken up with water, the mixture is extracted with DCM, the organic phase is dried over $Na_2SO_4$ and the solvent is evaporated off under vacuum. The residue is chromatographed on silica gel, elution being carried out with a mixture of DCM/propan-2-ol (97/3; v/v). 0.06 g of the expected compound is obtained.

Example 5

Compound No. 36 and Compound No. 37

5-(4-Bromophenyl)-2-[(4-tert-butylcyclohexyl)methyl]-6-(2,4-dichlorophenyl)-2,5-dihydro-3H-pyrazolo[4,3-c]pyridazin-3-one, the least polar isomer and the most polar isomer A mixture of 0.5 g of the compound of Preparation 6.2, 0.57 g of the compound of Preparation 7.10 and 0.32 g of $K_2CO_3$ in 30 ml of dioxane and 5 ml of DMF is heated at 140° C. for 5 hours. The reaction mixture is concentrated under vacuum, the residue is taken up with water, the mixture is extracted with EtOAc, the organic phase is dried over $Na_2SO_4$, and the solvent is evaporated off under vacuum. The residue is chromatographed on silica gel, elution being carried out with a mixture of DCM/MeOH (100/2; v/v). The two isomers are separated:

Compound No. 36: the least polar: m=0.035 g after crystallization from iso ether;
MH$^+$: 587; tr=13.05 (M1);
$^1$H NMR: DMSO-d$_6$ (250 MHz): δ (ppm): 0.77-1.67: up: 18H, 2.26: se: 1H; 3.94: mt: 2H, 7.32-7.77: m: 8H.

Compound No. 37: the most polar: m=0.065 g after crystallization from iso ether.
MH$^+$: 587; tr=13.03 (M1);
$^1$H NMR: DMSO-d$_6$ (250 MHz): δ (ppm): 0.81: s: 9H, 0.86-1.12: up: 4H, 1.58-1.90: up: 4H, 3.73: mt: 2H, 7.29-7.79: up: 8H.

Example 6

Compound No. 51

5-(4-Chlorophenyl)-6-(2,4-dichlorophenyl)-7-hydroxy-2-[4-(trifluoromethyl)-benzyl]-2,5-dihydro-3H-pyrazolo[4,3-c]pyridazin-3-one A mixture of 0.6 g of Compound No. 50 and 30 ml of a solution of HBr at 45% in acetic acid is heated at 80° C. for 5 hours. The reaction mixture is concentrated under vacuum, the residue is taken up with a saturated solution of $NaHCO_3$, the mixture is left to stir at AT for 1 hour, and the precipitate formed is spin-filter-dried. The precipitate is taken up with MeOH, the mixture is acidified by the addition of concentrated HCl, and the precipitate formed is spin-filter-dried and dried. 0.09 g of the expected compound is obtained.

Example 7

Compound No. 57

6-(2,4-Dichlorophenyl)-5-(4-fluorophenyl)-2-[4-(trifluoromethoxy)benzyl]-2,5-dihydro-3H-pyrazolo[4,3-c]pyridazin-3-one A mixture of 0.53 g of the compound of Preparation 6.6, 0.56 g of 1-(bromomethyl)-4-(trifluoromethoxy)benzene and 1.88 g of $Cs_2CO_3$ in 30 ml of dioxane and 5 ml of DMF is heated at 160° C. for 2 hours. The reaction mixture is concentrated under vacuum, the residue is taken up with water, the mixture is extracted with DCM, the organic phase is dried over $Na_2SO_4$ and the solvent is evaporated off under vacuum. The residue is chromatographed on silica H gel, elution being carried out with DCM and then with a mixture of DCM/MeOH (100/5; v/v). 0.04 g of the expected compound is obtained after crystallization from iso ether.

Example 8

Compound No. 65

6-(2,4-Dichlorophenyl)-5-(4-methoxyphenyl)-2-[4-[(trifluoromethyl)thio]benzyl]-2,5-dihydro-3H-pyrazolo[4,3-c]pyridazin-3-one A mixture of 2 g of the compound of Preparation 6.8, 1.73 g of 1-(bromomethyl)-4-[(trifluoromethyl)thio]benzene and 6.87 g of $Cs_2CO_3$ in 103 ml of dioxane is refluxed for 2 hours. The reaction mixture is concentrated under vacuum, the residue is taken up with water, the mixture is extracted with DCM, the organic phase is dried over $Na_2SO_4$ and the solvent is evaporated off under vacuum. The residue is chromatographed on silica gel H, elution being carried out with DCM and then with a mixture of DCM/MeOH (100/5; v/v). 1.164 g of the expected compound are obtained.

Example 9

Compound No. 76

6-(2,4-Dichlorophenyl)-5-(4-hydroxyphenyl)-2-[4-[(trifluoromethyl)thio]benzyl]-2,5-dihydro-3H-pyrazolo[4,3-c]pyridazin-3-one A solution of 0.91 g of Compound No. 65 in 50 ml of DCM is cooled to −20° C., 6.3 ml of a 1M solution of $BBr_3$ in DCM are added under a nitrogen atmosphere, and the mixture is left to stir for 48 hours while allowing the temperature to return to AT. The reaction mixture is poured into ice-cold water, the mixture is extracted with DCM, the organic phase is dried over $Na_2SO_4$ and the solvent is evaporated off under vacuum. The residue is chromatographed on silica gel H, elution being carried out with DCM and then with a mixture of DCM/MeOH (100/1; v/v). 0.49 g of the expected compound is obtained.

Example 10

Compound No. 77

4-[6-(2,4-dichlorophenyl)-3-oxo-2-[4-[(trifluoromethyl)thio]benzyl]-2,3-dihydro-5H-pyrazolo[4,3-c]pyridazin-5-yl]phenyl-3,3,3-trifluoropropane-1-sulfonate A solution of 0.245 g of Compound No. 76 and 0.12 ml of triethylamine in 100 ml of DCM is cooled to 0° C., 0.17 g of 3,3,3-trifluoropropane-1-sulfonyl chloride is added, and the mixture is left to stir while allowing the temperature to return to AT. Water is added to the reaction mixture, the mixture is extracted with DCM, the organic phase is washed with water and dried over $Na_2SO_4$, and the solvent is evaporated off under vacuum. 0.25 g of the expected compound is obtained after crystallization from iso ether.

Example 11

Compound No. 78

4-[6-(2,4-dichlorophenyl)-3-oxo-2-[4-[(trifluoromethyl)thio]benzyl]-2,3-dihydro-5H-pyrazolo[4,3-c]pyridazin-5-yl]phenylpropane-1-sulfonate A solution of 0.17 g of Compound No. 76 and 0.08 ml of triethylamine in 100 ml of DCM is cooled to 0° C., 0.07 ml of propane-1-sulfonyl chloride is added, and the mixture is left to stir for 2 hours while allowing the temperature to return to AT. Water is added to the reaction mixture, the mixture is extracted with DCM, the organic phase is washed with water and dried over $Na_2SO_4$, and the solvent is evaporated off under vacuum. 0.167 g of the expected compound is obtained after crystallization from iso ether.

Example 12

Compound No. 90-SAR 117027

N-[2-[[3-Chloro-4-[5-[4-(methylthio)phenyl]-3-oxo-2-[4-(trifluoromethyl)-benzyl]-3,5-dihydro-2H-pyrazolo[4,3-c]pyridazin-6-yl]phenyl]thio]ethyl]acetamide A mixture of 0.46 ml of N-(2-mercaptoethyl)acetamide and 0.066 g of NaH at 60% in oil, in 25 ml of xylene, is left to stir at 60° C. for 1 hour. 1 g of compound No. 89, 0.12 g of $Pd_2(dba)_3$ and 0.088 g of xantphos are then added and the mixture is refluxed overnight. The reaction mixture is concentrated under vacuum, the residue is taken up with a 10% HCl solution, the mixture is extracted with EtOAc, an insoluble material is filtered off, the product is separated by settling out, the organic phase is dried over $Na_2SO_4$, and the solvent is evaporated off under vacuum. The residue is chromatographed on silica gel, elution being carried out with a mixture of DCM/MeOH (100/5; V/V). 0.86 g of the expected compound is obtained after crystallization from iso ether.

$MH^+$=644; tr=9.48 (M1).

Example 13

Compound No. 91-SAR 115935

6-[2-Chloro-4-[(3-hydroxypropyl)thio]phenyl]-5-[4-(methylthio)phenyl]-2-[4-(trifluoromethyl)benzyl]-2,5-dihydro-3H-pyrazolo[4,3-c]pyridazin-3-one A mixture of 0.24 g of 3-mercaptopropan-1-ol and 0.04 g of NaH at 60% in oil, in 34 ml of xylene, is left to stir at 60° C. for 1 hour. 0.61 g of compound No. 89, 0.074 g of $Pd_2(dba)_3$ and 0.055 g of xantphos are then added and the mixture is refluxed overnight. The reaction mixture is concentrated under vacuum, the residue is taken up with a 10% HCl solution, the mixture is extracted with EtOAc, an insoluble material is filtered off, the product is separated by settling out, the organic phase is dried over $Na_2SO_4$, and the solvent is evaporated off under vacuum. The residue is chromatographed on silica gel, elution being carried out with a mixture of DCM/EtOAc (100/30; V/V). 0.68 g of the expected compound is obtained.

$MH^+$=617; tr=9.96 (M1).

Example 14

Compound No. 92-SAR 117026

N-[3-[(3-Chloro-4-[5-[4-(methylthio)phenyl]-3-oxo-2-[4-(trifluoromethyl)-benzyl]-3,5-dihydro-2H-pyrazolo[4,3-c]pyridazin-6-yl]phenyl)thio]propyl]methanesulfonamide A) 3-[[3-Chloro-4-[5-[4-(methylthio)phenyl]-3-oxo-2-[4-(trifluoromethyl)-benzyl]-3,5-dihydro-2H-pyrazolo[4,3-c]pyridazin-6-yl]phenyl]thio]propyl-methane-sulfonate A solution of 0.58 g of compound No. 91 and 0.26 ml of triethylamine in 10 ml of DCM is cooled to 0° C., 0.11 ml of methanesulfonyl chloride is added and the mixture is left to stir overnight while allowing the temperature to return to AT. The reaction mixture is concentrated under vacuum, the residue is taken up with a buffer solution, pH=2, the mixture is extracted with DCM, the organic phase is dried over $Na_2SO_4$ and the solvent is evaporated off under vacuum. The residue is chromatographed on silica gel, elution being carried out with a mixture of DCM/EtOAc (100/35; V/V). 0.53 g of the expected compound is obtained after crystallization from iso ether.

B) N-[3-[(3-Chloro-4-[5-[4-(methylthio)phenyl]-3-oxo-2-[4-(trifluoromethyl)-benzyl]-3,5-dihydro-2H-pyrazolo[4,3-c]pyridazin-6-yl]phenyl)thio]propyl]methane-sulfonamide A solution of 0.3 g of methanesulfonamide and 0.12 g of NaH at 60% in oil, in 15 ml of DMF, is cooled to 0° C., 0.52 g of the compound from the preceding stage is added and the mixture is left to stir for 5 hours while allowing the temperature to return to AT. 0.006 g of NaI is then added and the mixture is left to stir at AT for 30 minutes. The reaction mixture is concentrated under vacuum, the residue is taken up with water, the mixture is extracted with EtOAc, the organic phase is dried over $Na_2SO_4$, and the solvent is evaporated off under vacuum. The residue is chromatographed on silica gel, elution being carried out with a mixture of DCM/MeOH (100/5; V/V). 0.19 g of the expected compound is obtained after crystallization from iso ether.

$MH^+$=694; tr=9.98 (M1).

Example 15

Compound No. 94-SAR 125856

6-[2-Chloro-4-[(3,3,3-trifluoropropyl)thio]phenyl]-5-[4-(methylthio)phenyl]-2-[4-(trifluoromethyl)thio]benzyl]-2,5-dihydro-3H-pyrazolo[4,3-c]pyridazin-3-one A mixture of 0.32 g of compound No. 93, 0.1 g of sodium 3,3,3-trifluoropropane-1-thiolate, 0.036 g of $Pd_2(dba)_3$ and 0.027 g of xantphos in 20 ml of xylene is refluxed overnight. The reaction mixture is concentrated under vacuum, the residue is taken up with a 10% HCl solution, the mixture is extracted with EtOAc, an insoluble material is filtered off, the product is separated by settling out, the organic phase is dried over $Na_2SO_4$, and the solvent is evaporated off under vacuum. The residue is chromatographed on silica gel, elution being carried out with a mixture of DCM/EtOAc (100/20; V/V). 0.11 g of the expected compound is obtained.

$MH^+$=687; tr=11.82 (M1).

Example 16

Compound No. 95-SAR 119436

N-[2-[[3-Chloro-4-[5-[4-(methylthio)phenyl]-3-oxo-2-[4-[(trifluoromethyl)thio]-benzyl]-3,5-dihydro-2H-pyrazolo[4,3-c]pyridazin-6-yl]phenyl]thio]ethyl]acetamide This compound is prepared according to the protocol described in Example 12, using 1 g of compound No. 93, 0.44 ml of N-(2-mercaptoethyl)acetamide, 0.06 g of NaH at 60% in oil, 0.11 g of $Pd_2(dba)_3$ and 0.084 g of xantphos in 25 ml of xylene. 0.57 g of the expected compound is obtained.

$MH^+$=676; tr=9.94 (M1).

Example 17

Compound No. 96-SAR 124029

6-[2-Chloro-4-(ethylthio)phenyl]-5-[4-(methylthio)phenyl]-2-[4-[(trifluoro-methyl)thio]benzyl]-2,5-dihydro-3H-pyrazolo[4,3-c]pyridazin-3-one This compound is prepared according to the protocol described in Example 12, using 1 g of compound No. 93, 0.07 g of NaH at 60% in oil, 0.13 ml of ethanethiol, 0.11 g of $Pd_2(dba)_3$ and 0.084 g of xantphos in 25 ml of xylene. 0.489 g of the expected compound is obtained.

$MH^+$=619; tr=11.80 (M1).

Example 18

Compound No. 102-SAR 100912

6-[2-Chloro-4-[2-(dimethylamino)ethoxy]phenyl]-5-[4-(methylthio)phenyl]-2-[4-(trifluoromethyl)benzyl]-2,5-dihydro-3H-pyrazolo[4,3-c]pyridazin-3-one A) 6-(2-Chloro-4-hydroxyphenyl)-5-[4-(methylthio)phenyl]-2-[4-(trifluoro-methyl)benzyl]-2,5-dihydro-3H-pyrazolo[4,3-c]pyridazin-3-one A solution of 2 g of compound No. 99 in 40 ml of DCM is cooled to −20° C., 10.77 ml of a 1M solution of $BBr_3$ in DCM are added under a nitrogen atmosphere and the mixture is left to stir for 48 hours while allowing the temperature to return to AT. The reaction mixture is poured onto ice, the mixture is extracted with DCM, the organic phase is dried over $Na_2SO_4$, and the solvent is evaporated off under vacuum. 2.047 g of the expected compound are obtained.

B) 6-[2-Chloro-4-[2-(dimethylamino)ethoxy]phenyl]-5-[4-(methylthio)phenyl]-2-[4-(trifluoromethyl)benzyl]-2,5-dihydro-3H-pyrazolo[4,3-c]pyridazin-3-one A mixture of 0.5 g of the compound from the preceding stage, 0.27 g of 2-chloro-N,N-dimethylethanamine hydrochloride and 1.5 g of $Cs_2SO_3$ in 30 ml of acetonitrile is refluxed overnight. The reaction mixture is concentrated under vacuum, the residue is taken up with water, the mixture is extracted with DCM, the organic phase is dried over $Na_2SO_4$, and the solvent is evaporated under vacuum. The residue is chromatographed on silica gel, elution being carried out with a mixture of DCM/EtOAc (100/30; V/V). 0.05 g of the expected compound is obtained.

$MH^+$=614; tr=7.14 (M1).

Example 19

Compound No. 103-SAR 157102

6-[2-Chloro-4-(2,2,2-trifluoroethoxy)phenyl]-5-[4-(methylthio)phenyl]-2-[4-(trifluoromethyl)benzyl]-2,5-dihydro-3H-pyrazolo[4,3-c]pyridazin-3-one A mixture of 0.45 g of the compound obtained in stage A of Example 18, 0.38 g of 2,2,2-trifluoroethyltrifluoromethanesulfonate and 0.28 g of $NaHCO_3$ in 14 ml of EtOH is refluxed for 2 hours. The reaction mixture is concentrated under vacuum, the residue is taken up with water, the mixture is extracted with DCM, the organic phase is dried over $Na_2SO_4$, and the solvent is evaporated off under vacuum. The residue is chromatographed on silica gel, elution being carried out with a mixture of DCM/EtOAc (100/30; V/V). 0.145 g of the expected compound is obtained after crystallization from iso ether.

$MH^+$=625; tr=10.87 (M1).

Example 20

Compound No. 111-SSR 154266

6-(2,4-Dichlorophenyl)-5-[4-[2-(dimethylamino)ethoxy]phenyl]-2-[4-(trifluoro-methyl)benzyl]-2,5-dihydro-3H-pyrazolo[4,3-c]pyridazin-3-one A) 6-(2,4-Dichlorophenyl)-5-(4-hydroxyphenyl)-2-[4-(trifluoromethyl)benzyl]-2,5-dihydro-3H-pyrazolo[4,3-c]pyridazin-3-one A solution of 4.5 g of compound No. 64 in 83 ml of DCM is cooled to −20° C., 24.75 ml of a 1M solution of BBr$_3$ in DCM are added under a nitrogen atmosphere and the mixture is left to stir for 48 hours while allowing the temperature to return to AT. The reaction mixture is poured onto ice, the mixture is extracted with DCM, the organic phase is dried over Na$_2$SO$_4$, and the solvent is evaporated off under vacuum. 4.55 g of the expected compound are obtained.

B) 6-(2,4-Dichlorophenyl)-5-[4-[2-(dimethylamino)ethoxy]phenyl]-2-[4-(tri-fluoromethyl)benzyl]-2,5-dihydro-3H-pyrazolo[4,3-c]pyridazin-3-one 0.02 g of NaH at 60% in oil is added to a mixture of 0.2 g of the compound from the preceding stage in 20 ml of dioxane, and the mixture is left to stir for 1 hour 30 minutes at AT. 0.37 g of Cs$_2$CO$_3$ and then 0.1 g of 2-chloro-N,N-dimethyl-ethanamine hydrochloride are added and the mixture is refluxed for 2 hours. The reaction mixture is concentrated under vacuum, the residue is taken up with water, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/5; V/V). 0.24 g of the expected compound is obtained after crystallization from iso ether.

MH$^+$=602; tr=8.67 (M1).

Example 21

Compound No. 121-SAR 137338 A

6-[4-[(2-Aminoethyl)thio]-2-chlorophenyl]-5-[4-(methylthio)phenyl]-2-[4-(tri-fluoromethyl)benzyl]-2,5-dihydro-3H-pyrazolo[4,3-c]pyridazin-3-one hydrochloride A) tert-Butyl[2-[(3-chloro-4-[5-[4-(methylthio)phenyl]-3-oxo-2-[4-(trifluoro-methyl)benzyl]-3,5-dihydro-2H-pyrazolo[4,3-c]pyridazin-6-yl]phenyl]thio]ethyl]-carbamate A mixture of 3.33 ml of tert-butyl (2-mercaptoethyl)carbamate and 0.31 g of NaH at 60% in oil, in 50 ml of xylene, is left to stir for 1 hour at 60° C. 4.63 g of compound No. 89, 0.56 g of Pd$_2$(dba)$_3$ and 0.4 g of xantphos are then added and the mixture is refluxed overnight. The reaction mixture is concentrated under vacuum, the residue is taken up with a 10% HCl solution, the mixture is extracted with EtOAc, an insoluble material is filtered off, the product is separated by settling out, the organic phase is dried over Na$_2$SO$_4$, and the solvent is evaporated off under vacuum. The residue is chromatographed on silica gel, elution being carried out with a mixture of DCM/EtOAc (100/40; V/V). 4.15 g of the expected compound are obtained after crystallization from iso ether.

B) 6-[4-[(2-Aminoethyl)thio]-2-chlorophenyl]-5-[4-(methylthio)phenyl]-2-[4-(tri-fluoromethyl)benzyl]-2,5-dihydro-3H-pyrazolo[4,3-c]pyridazin-3-one hydrochloride A mixture of 4.15 g of the compound from the preceding stage and 43.27 ml of a 2N solution of hydrochloric ether in 15 ml of DCM is left to stir at AT for 2 hours. The reaction mixture is concentrated under vacuum, the residue is taken up with ether, and the precipitate formed is spin-dried. 256 g of the expected compound are obtained.

Example 22

Compound No. 122-SAR 137529

6-[2-Chloro-4-[[2-(dimethylamino)ethyl]thio]phenyl]-5-[4-(methylthio)phenyl]-2-[4-(trifluoromethyl)benzyl]-2,5-dihydro-3H-pyrazolo[4,3-c]pyridazin-3-one A mixture of 0.4 g of compound No. 121 in the form of a free base, 0.11 ml of a 37% solution of formaldehyde in water and 0.89 g of sodium triacetoxyborohydride in 25 ml of THF is left to stir at AT overnight. 30 ml of MeOH are then added and the mixture is refluxed for 30 minutes. The reaction mixture is concentrated under vacuum, the residue is taken up with water, the aqueous phase is alkalinized through the addition of 30% NaOH, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/5; V/V). 0.277 g of the expected compound is obtained after crystallization from iso ether.

Example 23

Compound No. 123-SAR 139296

6-(2-Chloro-4-{[2-(diethylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one A mixture of 0.45 g of compound No. 121 in the form of a free base, 0.11 ml of acetaldehyde and 0.33 g of sodium triacetoxyborohydride in 25 ml of THF is left to stir overnight at AT. 30 ml of MeOH are then added and the mixture is refluxed for 30 minutes. The reaction mixture is concentrated under vacuum, the residue is taken up with water, the aqueous phase is alkalinized through the addition of 30% NaOH, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/5; V/V). 0.061 g of the expected compound is obtained.

Example 24

Compound No. 125-SAR 139298

N-{2-[(3-Chloro-4-{5-[4-(methylthio)phenyl]-3-oxo-2-[4-(trifluoromethyl)-benzyl]-3,5-dihydro-2H-pyrazolo[4,3-c]pyridazin-6-yl}phenyl)thio]ethyl}methane-sulfonamide 0.06 ml of methanesulfonyl chloride is added to a mixture of 0.4 g of compound No. 121 in the form of a free base and 0.18 ml of triethylamine in 15 ml of DCM, and the mixture is left to stir for 3 hours at AT. The reaction mixture is concentrated under vacuum, the residue is taken up with a 10% HCl solution, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/5; V/V). 0.294 g of the expected compound is obtained.

Example 25

Compound No. 126-SAR 140559

N-{2-[(3-Chloro-4-{5-[4-(methylthio)phenyl]-3-oxo-2-[4-(trifluoromethyl)-benzyl]-3,5-dihydro-2H-pyrazolo[4,3-c]pyridazin-6-yl}phenyl)thio]ethyl}formamide 0.71 ml of acetic anhydride is added, dropwise, to a solution of 0.45 g of compound No. 121 in 1.69 ml of formic acid and the mixture is left to stir overnight at AT. The reaction mixture is concentrated under vacuum, the residue is taken up with ice-cold water, the aqueous phase is alkalinized through the addition of a concentrated solution of NaOH, the mixture is extracted with DCM, the organic phase is dried over Na$_2$SO$_4$, and the solvent is evaporated off under vacuum. The residue is chromatographed on silica gel, elution being carried out with a mixture of DCM/MeOH (100/5; V/V). 0.32 g of the expected compound is obtained after crystallization from iso ether.

The table which follows illustrates the chemical structures and the physical properties of some examples of compounds according to the invention. In this table:

Me, Et, nPr, iPr, nBu and tBu represent, respectively, methyl, ethyl, n-propyl, n-butyl and tert-butyl groups.

TABLE VI

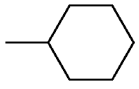

(I)

| Compound No. | R$_1$ | R$_2$ | R$_3$ | R$_4$ | MH+; tr (min) (Method) NMR |
|---|---|---|---|---|---|
| 1 | 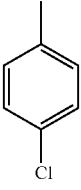 | 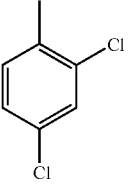 | 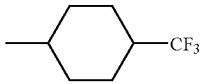 | H | 487; 11.24 (M1) |
| 2 |  | 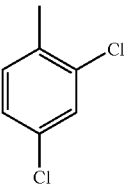 | 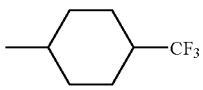 | H | 555; 11.45 (M1) The least polar |
| 3 | 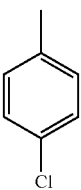 | 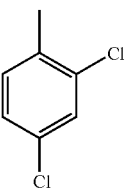 | 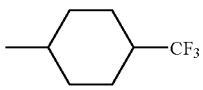 | H | 555; 11.42 (M1) The most polar |

TABLE VI-continued
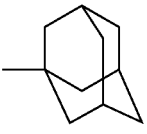
(I)
| Compound No. | R₁ | R₂ | R₃ | R₄ | MH+; tr (min) (Method) NMR |
|---|---|---|---|---|---|
| 4 | 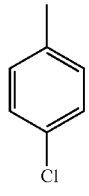 | 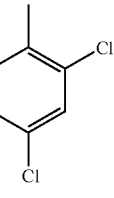 4-Cl-C₆H₄ | 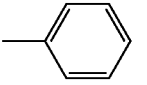 2,4-Cl₂-C₆H₃ | H | 539; 12.40 (M1) |
| 5 | 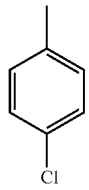 | 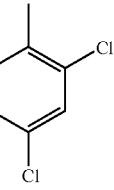 | 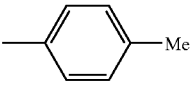 | H | 481; 10.53 (M1) |
| 6 | 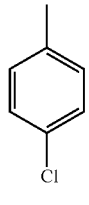 4-Me-C₆H₄ | 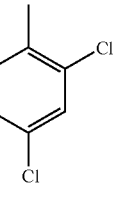 | 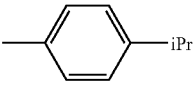 | H | 495; 10.79 (M1) |
| 7 | 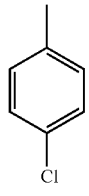 4-iPr-C₆H₄ | 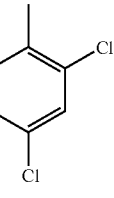 | 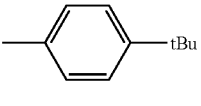 | H | 523; 11.69 (M1) NMR |
| 8 | 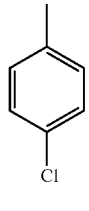 4-tBu-C₆H₄ | 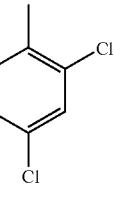 | 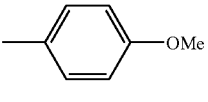 | H | 537; 11.92 (M1) NMR |
| 9 | 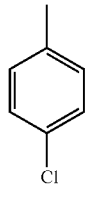 4-OMe-C₆H₄ | 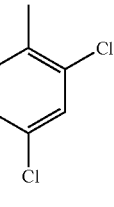 | | H | 511; 10.45 (M1) |

TABLE VI-continued
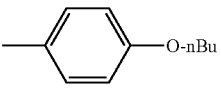
(I)
| Compound No. | R₁ | R₂ | R₃ | R₄ | MH+; tr (min) (Method) NMR |
|---|---|---|---|---|---|
| 10 | 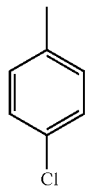 4-O-nBu-phenyl | 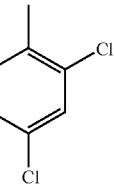 4-Cl-phenyl | 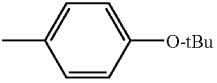 2,4-diCl-phenyl | H | 553; 11.81 (M1) |
| 11 | 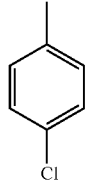 4-O-tBu-phenyl | 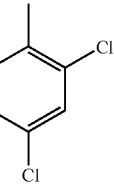 4-Cl-phenyl | 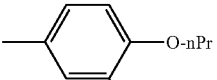 2,4-diCl-phenyl | H | 553; 11.35 (M1) |
| 12 | 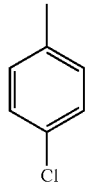 4-O-nPr-3-F-phenyl | 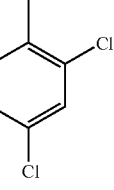 4-Cl-phenyl | 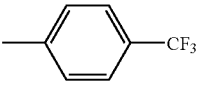 2,4-diCl-phenyl | H | 557; 23.75 (M3) |
| 13 | 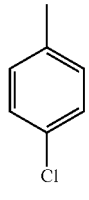 4-CF₃-phenyl | 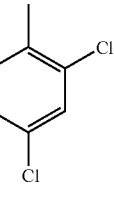 4-Cl-phenyl | 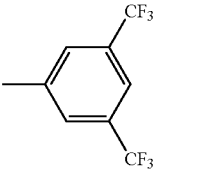 2,4-diCl-phenyl | H | 549; 11.17 (M1) NMR |
| 14 | 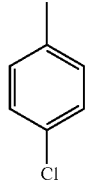 3,5-di-CF₃-phenyl | 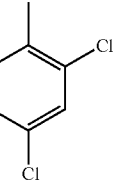 4-Cl-phenyl | 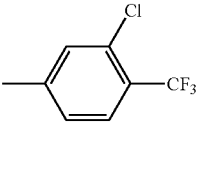 2,4-diCl-phenyl | H | 617; 12.09 (M1) |
| 15 | 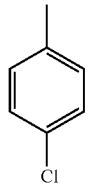 2-Cl-4-CF₃-phenyl | 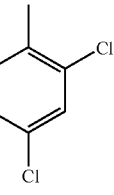 4-Cl-phenyl | 2,4-diCl-phenyl | H | 583; 11.71 (M1) |

TABLE VI-continued (I)

| Compound No. | R₁ | R₂ | R₃ | R₄ | MH+; tr (min) (Method) NMR |
|---|---|---|---|---|---|
| 16 | 3-F,4-CF₃-benzyl | 4-Cl-phenyl | 2,4-diCl-phenyl | H | 567; 11.52 (M1) NMR |
| 17 | 3,5-diF,4-CF₃-benzyl | 4-Cl-phenyl | 2,4-diCl-phenyl | H | 599; 11.59 (M1) |
| 18 | 4-OCHF₂-phenyl | 4-Cl-phenyl | 2,4-diCl-phenyl | H | 547; 10.91 (M1) |
| 19 | 4-OCF₂CHF₂-phenyl | 4-Cl-phenyl | 2,4-diCl-phenyl | H | 597; 11.31 (M1) |
| 20 | 3-OCF₃-phenyl | 4-Cl-phenyl | 2,4-diCl-phenyl | H | 565; 11.38 (M1) |
| 21 | 3-Cl,4-OCF₃-phenyl | 4-Cl-phenyl | 2,4-diCl-phenyl | H | 599; 12.01 (M1) |

TABLE VI-continued
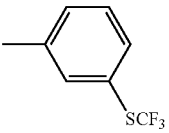
(I)
| Compound No. | R₁ | R₂ | R₃ | R₄ | MH+; tr (min) (Method) NMR |
|---|---|---|---|---|---|
| 22 | 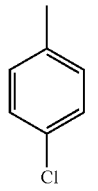 | 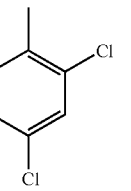 | 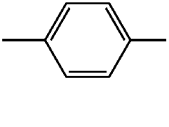 | H | 581; 11.93 (M1) |
| 23 | 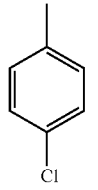 | 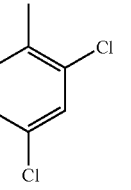 | 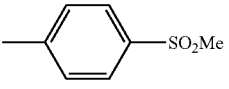 | H | 581; 11.98 (M1) NMR |
| 24 | 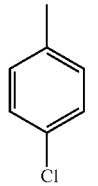 | 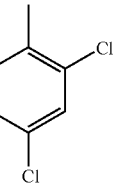 | 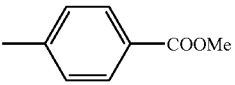 | H | 559; 9.52 (M1) |
| 25 | 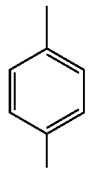 | 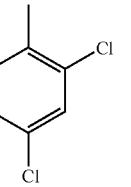 | 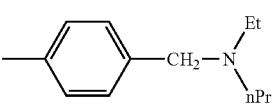 | H | 539; 10.30 (M1) |
| 26 | 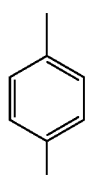 | 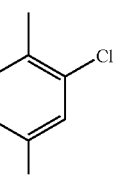 | 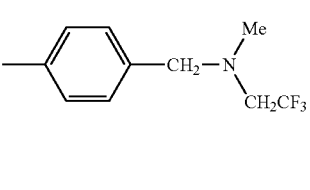 | H | 580; 7.69 (M1) HCl |
| 27 | 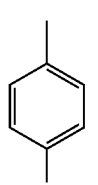 | 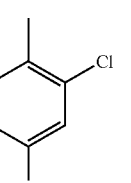 | | H | 606; 11.32 (M1) HCl |

TABLE VI-continued (I)

| Compound No. | R₁ | R₂ | R₃ | R₄ | MH+; tr (min) (Method) NMR |
|---|---|---|---|---|---|
| 28 | 4-biphenyl-CH₂- | 4-Cl-C₆H₄- | 2,4-diCl-C₆H₃- | H | 557; 11.60 (M1) |
| 29 | 4-(1,2,4-triazol-1-yl)phenyl- | 4-Cl-C₆H₄- | 2,4-diCl-C₆H₃- | H | 548; 9.50 (M1) |
| 30 | 4-(1,2,3-thiadiazol-4-yl)phenyl- | 4-Cl-C₆H₄- | 2,4-diCl-C₆H₃- | H | 565; 10.36 (M1) |
| 31 | —CH₂—C₆H₅ | 4-Cl-C₆H₄- | 2,4-diCl-C₆H₃- | H | 495; 10.72 (M1) |
| 32 | 4-pyridyl- | 4-Cl-C₆H₄- | 2,4-diCl-C₆H₃- | H | 482; 7.54 (M1) |
| 33 | 6-CF₃-pyridin-3-yl- | 4-Cl-C₆H₄- | 2,4-diCl-C₆H₃- | H | 550; 10.46 (M1) |

TABLE VI-continued
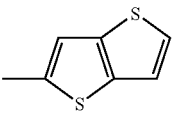
(I)
| Compound No. | R₁ | R₂ | R₃ | R₄ | MH+; tr (min) (Method) NMR |
|---|---|---|---|---|---|
| 34 | 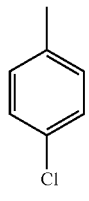 | 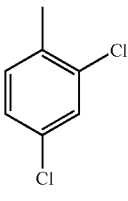 | 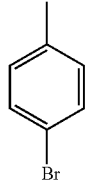 | H | 543; 11.16 (M1) |
| 35 | —CH(nPr)₂ | 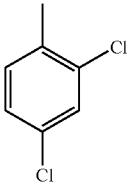 | 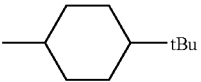 | H | 547; 12.29 (M1) |
| 36 | 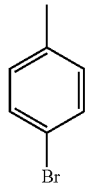 | 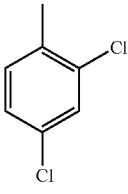 | 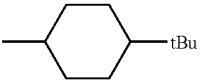 | H | 587; 13.05 (M1) The least polar |
| 37 | 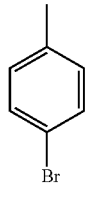 | 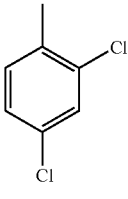 | 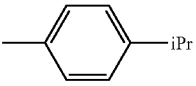 | H | 587; 13.03 (M1) The most polar |
| 38 | 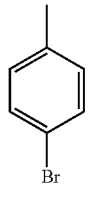 | 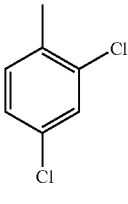 | 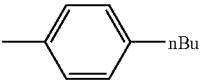 | H | 567; 11.74 (M1) NMR |
| 39 | 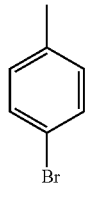 | 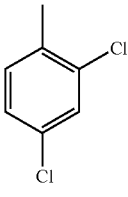 | | H | 581; 12.27 (M1) NMR |

TABLE VI-continued
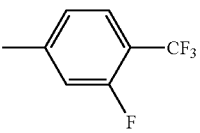
(I)
| Compound No. | R₁ | R₂ | R₃ | R₄ | MH+; tr (min) (Method) NMR |
|---|---|---|---|---|---|
| 40 | 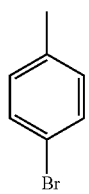 | 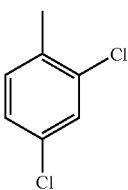 | 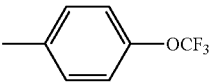 | H | 611; 11.47 (M1) NMR |
| 41 | 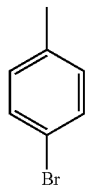 | 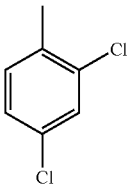 | 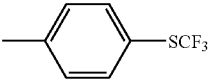 | H | 609; 11.52 (M1) NMR |
| 42 | 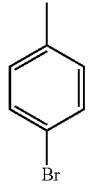 | 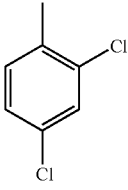 | 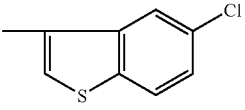 | H | 625; 11.81 (M1) NMR |
| 43 | 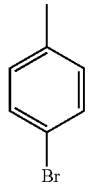 | 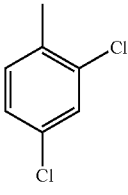 | 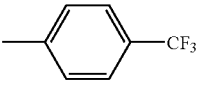 | H | 615; 11.86 (M1) |
| 44 | 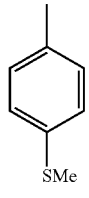 | 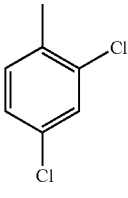 | 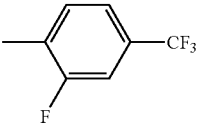 | H | 561; 11.27 (M1) NMR |
| 45 | 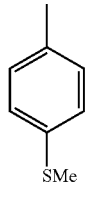 | 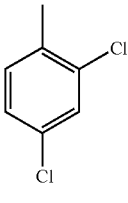 | | H | 579; 11.05 (M5) NMR |

TABLE VI-continued
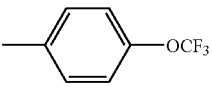
(I)
| Compound No. | R₁ | R₂ | R₃ | R₄ | MH+; tr (min) (Method) NMR |
|---|---|---|---|---|---|
| 46 | 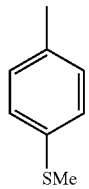 | 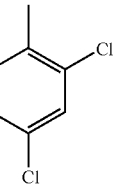 | 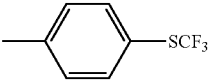 | H | 577; 15.07 (M4) NMR |
| 47 | 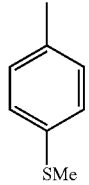 | 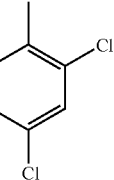 | 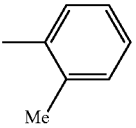 | H | 593; 11.70 (M1) |
| 48 | 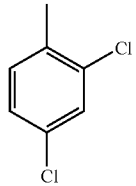 | 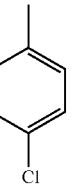 | 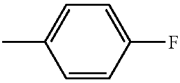 | Me | 509; 11.07 (M1) |
| 49 | 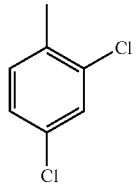 | 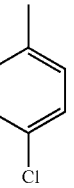 | 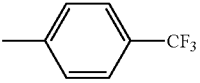 | Me | 513; 10.76 (M1) |
| 50 | 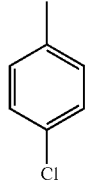 | 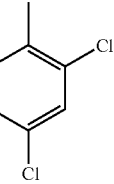 | 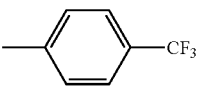 | OMe | 579; 11.70 (M1) |
| 51 | 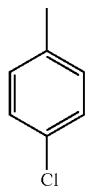 | | 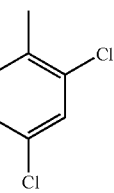 | OH | 565; 10.47 (M1) |

TABLE VI-continued
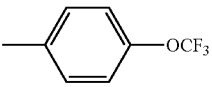
(I)
| Compound No. | R₁ | R₂ | R₃ | R₄ | MH+; tr (min) (Method) NMR |
|---|---|---|---|---|---|
| 52 | 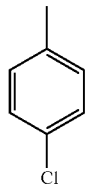 | 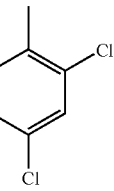 | 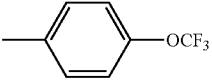 | OMe | 595; 11.83 (M1) |
| 53 | 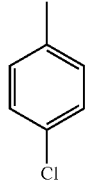 | 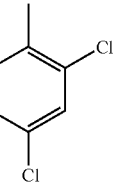 | 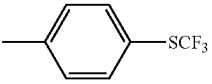 | OH | 581; 10.57 (M1) |
| 54 | 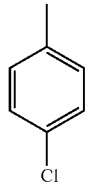 | 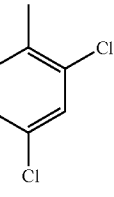 | 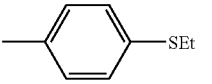 | OMe | 611; 12.13 (M1) |
| 55 | 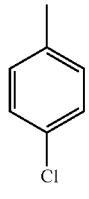 | 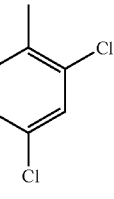 | 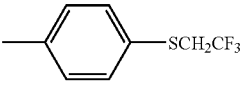 | H | 541; 11.11 (M5) |
| 56 | 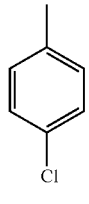 | 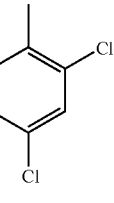 | 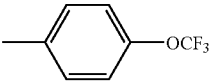 | H | 595; 11.45 (M1) |
| 57 | 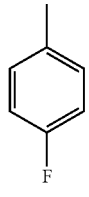 | 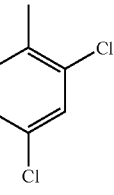 | | H | 549; 10.97 (M1) |

TABLE VI-continued
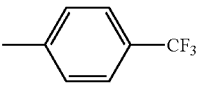
(I)
| Compound No. | R₁ | R₂ | R₃ | R₄ | MH+; tr (min) (Method) NMR |
|---|---|---|---|---|---|
| 58 | 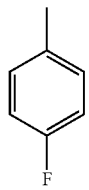 | 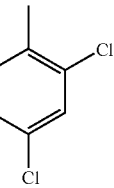 | 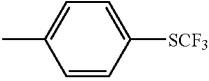 | H | 533; 10.83 (M1) |
| 59 | 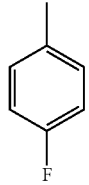 | 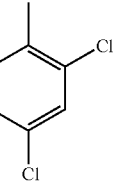 | 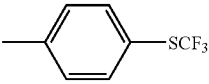 | H | 565; 11.32 (M1) |
| 60 | 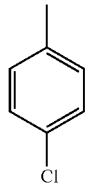 | 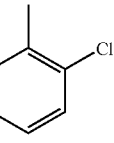 | 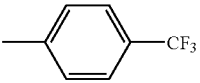 | H | 547; 11.10 (M1) NMR |
| 61 | 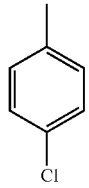 | 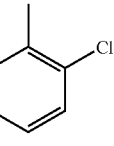 | 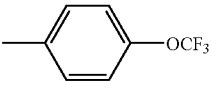 | H | 515; 10.60 (M1) |
| 62 | 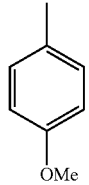 | 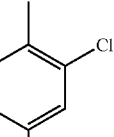 | 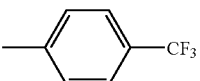 | H | 561; 10.60 (M2) NMR |
| 63 | 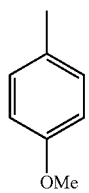 | 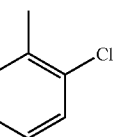 | | H | 563; 10.91 (M1) |

TABLE VI-continued
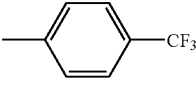
| Compound No. | R₁ | R₂ | R₃ | R₄ | MH+; tr (min) (Method) NMR |
|---|---|---|---|---|---|
| 64 | 4-CF₃-C₆H₄- | 4-OMe-C₆H₄- | 2,4-di-Cl-C₆H₃- | H | 545; 10.77 (M1) |
| 65 | 4-SCF₃-C₆H₄- | 4-OMe-C₆H₄- | 2,4-di-Cl-C₆H₃- | H | 577; 10.90 (M2) NMR |
| 66 | 4-SCF₃-C₆H₄- | 4-F-C₆H₄- | 2-Cl-C₆H₄- | H | 531; 10.70 (M1) NMR |
| 67 | 4-CF₃-C₆H₄- | 4-F-C₆H₄- | 2-Cl-C₆H₄- | H | 499; 10.22 (M1) |
| 68 | 4-OCF₃-C₆H₄- | 4-F-C₆H₄- | 2-Cl-C₆H₄- | H | 515; 10.38 (M1) |
| 69 | 4-SCF₃-C₆H₄- | 4-OMe-C₆H₄- | 2-Cl-C₆H₄- | H | 543; 10.43 (M2) |

TABLE VI-continued
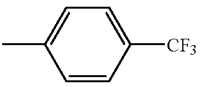
(I)
| Compound No. | R₁ | R₂ | R₃ | R₄ | MH+; tr (min) (Method) NMR |
|---|---|---|---|---|---|
| 70 | 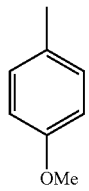 | 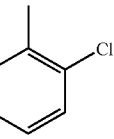 | 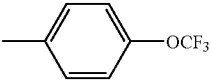 | H | 511; 9.92 (M2) |
| 71 | 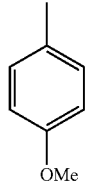 | 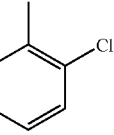 | 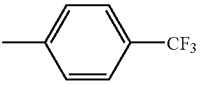 | H | 527; 10.08 (M2) |
| 72 | 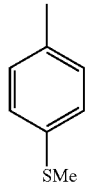 | 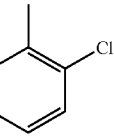 | 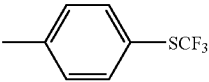 | H | 527; 10.51 (M1) |
| 73 | 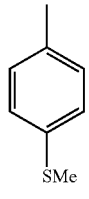 | 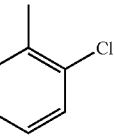 | 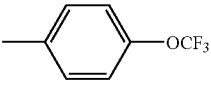 | H | 559; 10.97 (M1) |
| 74 | 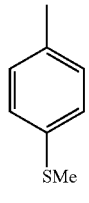 | 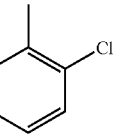 | 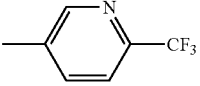 | H | 543; 10.62 (M1) |
| 75 | 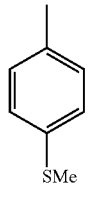 | 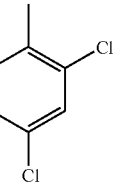 |  | H | 562; 10.34 (M1) |

TABLE VI-continued
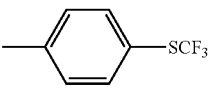
(I)
| Compound No. | R₁ | R₂ | R₃ | R₄ | MH+; tr (min) (Method) NMR |
|---|---|---|---|---|---|
| 76 | 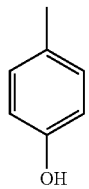 —SCF₃ | 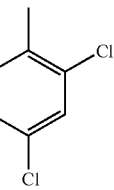 —OH | 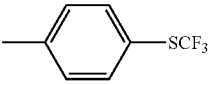 Cl, Cl | H | 563; 10.10 (M2) |
| 77 | 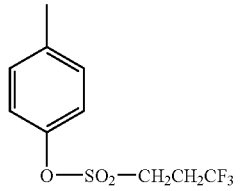 —SCF₃ | 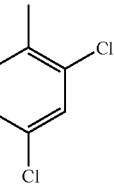 —O—SO₂—CH₂CH₂CF₃ | 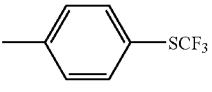 Cl, Cl | H | 723; 11.49 (M1) NMR |
| 78 | 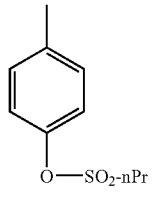 —SCF₃ | 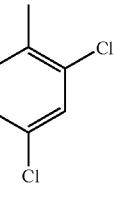 —O—SO₂-nPr | 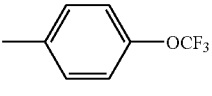 Cl, Cl | H | 669; 11.39 (M1) |
| 79 | 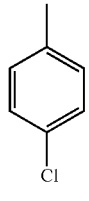 —OCF₃ | 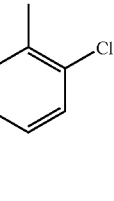 Cl | 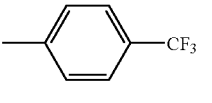 Cl | H | 531; 10.73 (M1) |
| 80 SSR156612 | 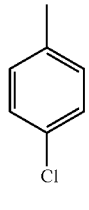 —CF₃ | 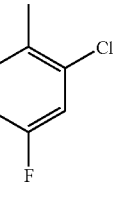 Cl | 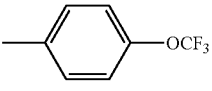 Cl, F | H | 533; 10.68 (M1) |
| 81 SSR156613 | 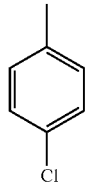 —OCF₃ | 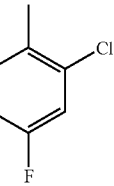 Cl | Cl, F | H | 549; 10.83 (M1) |

TABLE VI-continued (I)

| Compound No. | R₁ | R₂ | R₃ | R₄ | MH+; tr (min) (Method) NMR |
|---|---|---|---|---|---|
| 82 SSR156614 | 4-SCF₃-phenyl | 4-Cl-phenyl | 2-Cl-4-F-phenyl | H | 565; 11.16 (M1) |
| 83 SAR113787 | 4-CF₃-phenyl | 4-SMe-phenyl | 2,4-diCl-phenyl | OMe | 591; 11.59 (M1) |
| 84 SAR113953 | 4-OCF₃-phenyl | 4-SMe-phenyl | 2,4-diCl-phenyl | OMe | 607; 11.73 (M1) |
| 85 SAR113786 | 4-SCF₃-phenyl | 4-SMe-phenyl | 2,4-diCl-phenyl | OMe | 623; 12.06 (M1) |
| 86 SSR156807 | 4-CF₃-phenyl | 4-SMe-phenyl | 2-Cl-4-F-phenyl | H | 545; 10.32 (M2) |
| 87 SSR156808 | 4-OCF₃-phenyl | 4-SMe-phenyl | 2-Cl-4-F-phenyl | H | 561; 10.46 (M2) |

TABLE VI-continued
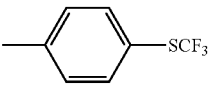
| Compound No. | R₁ | R₂ | R₃ | R₄ | MH+; tr (min) (Method) NMR |
|---|---|---|---|---|---|
| 88 SSR156809 | 4-SCF₃-phenyl | 4-SMe-phenyl | 3-Cl-4-F-phenyl | H | 577; 11.03 (M1) |
| 89 SAR112753 | 4-CF₃-phenyl | 4-SMe-phenyl | 3-Cl-4-Br-phenyl | H | 605; 11.18 (M1) NMR |
| 90 SAR117027 | 4-CF₃-phenyl | 4-SMe-phenyl | 3-Cl-4-S(CH₂)₂NHCOMe-phenyl | H | 644; 9.48 (M1) |
| 91 SAR115935 | 4-CF₃-phenyl | 4-SMe-phenyl | 3-Cl-4-S(CH₂)₃OH-phenyl | H | 617; 9.96 (M1) NMR |
| 92 SAR117026 | 4-CF₃-phenyl | 4-SMe-phenyl | 3-Cl-4-S(CH₂)₃NHSO₂Me-phenyl | H | 694; 9.98 (M1) |
| 93 SAR118666 | 4-SCF₃-phenyl | 4-SMe-phenyl | 3-Cl-4-Br-phenyl | H | 637; 18.70 (M6) NMR |

TABLE VI-continued
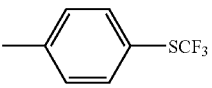
(I)
| Compound No. | R₁ | R₂ | R₃ | R₄ | MH+; tr (min) (Method) NMR |
|---|---|---|---|---|---|
| 94 SAR125856 | 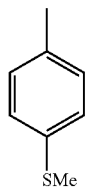 4-SCF₃-C₆H₄ | 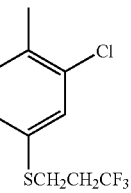 4-SMe-C₆H₄ | 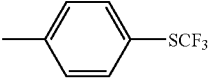 3-Cl-4-SCH₂CH₂CF₃-C₆H₃ | H | 687; 11.82 (M1) |
| 95 SAR119436 | 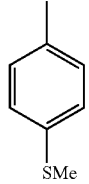 4-SCF₃-C₆H₄ | 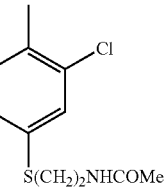 4-SMe-C₆H₄ | 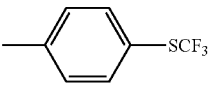 3-Cl-4-S(CH₂)₂NHCOMe-C₆H₃ | H | 676; 9.94 (M1) NMR |
| 96 SAR124029 | 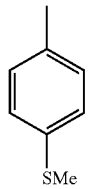 4-SCF₃-C₆H₄ | 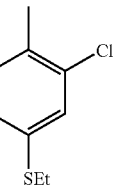 4-SMe-C₆H₄ | 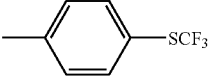 3-Cl-4-SEt-C₆H₃ | H | 619; 11.80 (M1) |
| 97 SAR119435 | 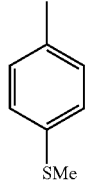 4-SCF₃-C₆H₄ | 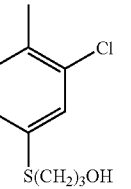 4-SMe-C₆H₄ | 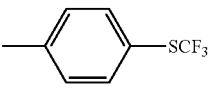 3-Cl-4-S(CH₂)₃OH-C₆H₃ | H | 649; 10.40 (M1) NMR |
| 98 SAR123057 | 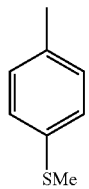 4-SCF₃-C₆H₄ | 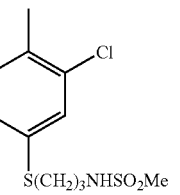 4-SMe-C₆H₄ | 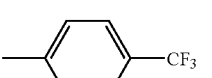 3-Cl-4-S(CH₂)₃NHSO₂Me-C₆H₃ | H | 726; 10.43 (M1) |
| 99 SSR156515 | 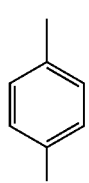 4-CF₃-C₆H₄ | 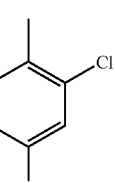 4-SMe-C₆H₄ | 3-Cl-4-OMe-C₆H₃ | H | 557; 10.52 (M1) NMR |

TABLE VI-continued
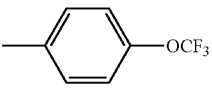
(I)
| Compound No. | R₁ | R₂ | R₃ | R₄ | MH+; tr (min) (Method) NMR |
|---|---|---|---|---|---|
| 100 SSR156516 | 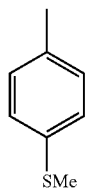 —OCF₃ | 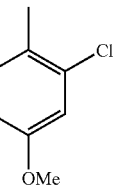 SMe |  Cl OMe | H | 573; 10.28 (M2) NMR |
| 101 SSR156517 | 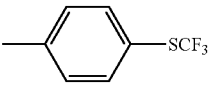 —SCF₃ | 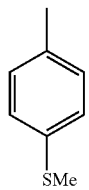 SMe | 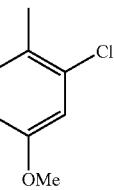 Cl OMe | H | 589; 10.62 (M2) NMR |
| 102 SAR100912 |  CF₃ | 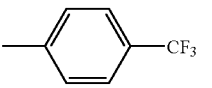 SMe | 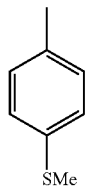 Cl O(CH₂)₂N(Me)₂ | H | 614; 7.14 (M1) NMR |
| 103 SSR157102 | 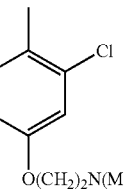 CF₃ |  SMe | 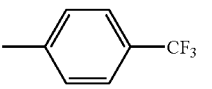 Cl OCH₂CF₃ | H | 625; 10.87 (M1) |
| 104 SAR101384 | 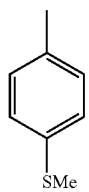 CF₃ | 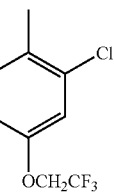 SMe |  Cl O(CH₂)₂SMe | H | 617; 11.06 (M1) NMR |
| 105 SAR105567 | 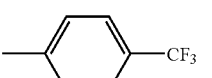 CF₃ | 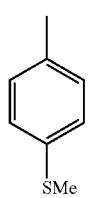 SMe | 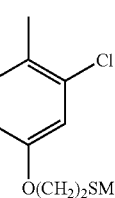 Cl SMe | H | 573; 10.91 (M1) NMR |

TABLE VI-continued
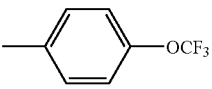
(I)
| Compound No. | R₁ | R₂ | R₃ | R₄ | MH+; tr (min) (Method) NMR |
|---|---|---|---|---|---|
| 106 SAR105566 | 4-OCF₃-phenyl | 4-SMe-phenyl | 3-Cl-4-SMe-phenyl | H | 589; 11.07 (M1) |
| 107 SAR105565 | 4-SCF₃-phenyl | 4-SMe-phenyl | 3-Cl-4-SMe-phenyl | H | 605; 11.40 (M1) NMR |
| 108 SAR126526 | 4-CF₃-phenyl | 4-OCF₃-phenyl | 2,4-diCl-phenyl | H | 599; 11.41 (M1) |
| 109 SAR127293 | 4-OCF₃-phenyl | 4-OCF₃-phenyl | 2,4-diCl-phenyl | H | 615; 11.54 (M1) |
| 110 SAR127183 | 4-SCF₃-phenyl | 4-OCF₃-phenyl | 2,4-diCl-phenyl | H | 631; 11.85 (M1) |
| 111 SSR154266 | 4-CF₃-phenyl | 4-O(CH₂)₂N(Me)₂-phenyl | 2,4-diCl-phenyl | H | 602; 8.67 (M1) |

TABLE VI-continued
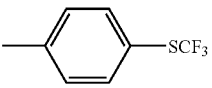
(I)
| Compound No. | R₁ | R₂ | R₃ | R₄ | MH+; tr (min) (Method) NMR |
|---|---|---|---|---|---|
| 112 SAR123058 | 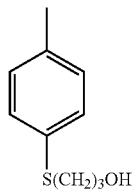 | 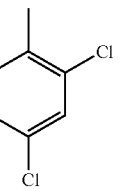 | 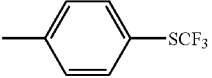 | H | 637; 10.66 (M1) |
| 113 SAR124030 | 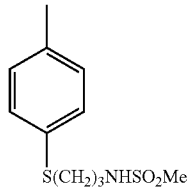 | 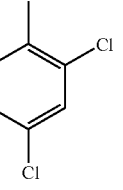 | 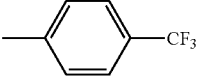 | H | 714; 10.75 (M1) |
| 114 | 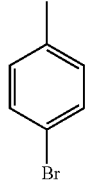 | 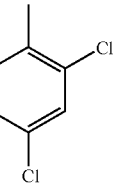 | 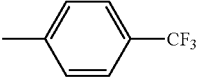 | H | |
| 115 SAR121779 | 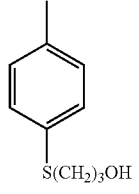 | 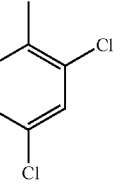 | 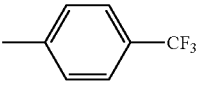 | H | 605; 10.17 (M1) |
| 116 SAR122848 | 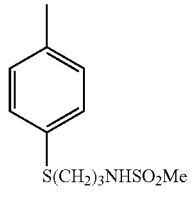 | 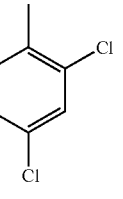 | 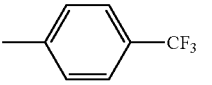 | H | 682; 10.28 (M1) NMR |
| 117 SAR122847 | 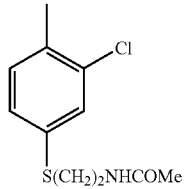 | 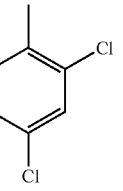 | | H | 632; 9.77 (M1) |

TABLE VI-continued
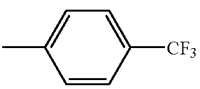
(I)
| Compound No. | R₁ | R₂ | R₃ | R₄ | MH+; tr (min) (Method) NMR |
|---|---|---|---|---|---|
| 118 SAR135535 | 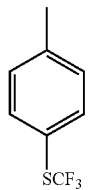 4-CF₃-C₆H₄ | 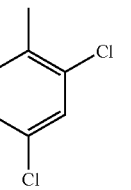 4-SCF₃-C₆H₄ | 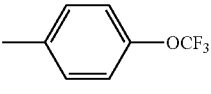 2,4-diCl-C₆H₃ | H | 615; 11.76 (M1) |
| 119 SAR135537 | 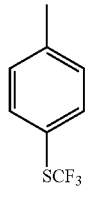 4-OCF₃-C₆H₄ | 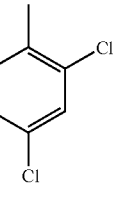 4-SCF₃-C₆H₄ | 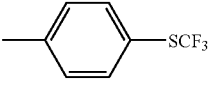 2,4-diCl-C₆H₃ | H | 631; 11.86 (M1) |
| 120 SAR135536 | 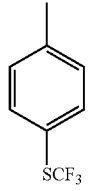 4-SCF₃-C₆H₄ | 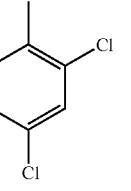 4-SCF₃-C₆H₄ | 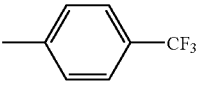 2,4-diCl-C₆H₃ | H | 647; 12.18 (M1) |
| 121 SAR137338A | 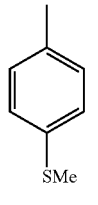 4-CF₃-C₆H₄ | 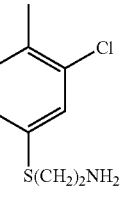 4-SMe-C₆H₄ | 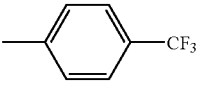 3-Cl-4-S(CH₂)₂NH₂-C₆H₃ | H | 602; 7.22 (M1) NMR |
| 122 SAR137529 | 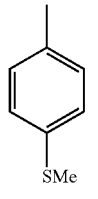 4-CF₃-C₆H₄ | 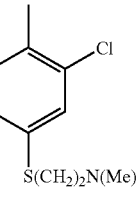 4-SMe-C₆H₄ | 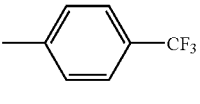 3-Cl-4-S(CH₂)₂N(Me)₂-C₆H₃ | H | 630; 10.04 (M2) NMR |
| 123 SAR139296 | 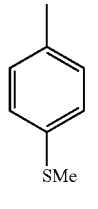 4-CF₃-C₆H₄ | 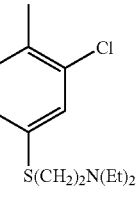 4-SMe-C₆H₄ | 3-Cl-4-S(CH₂)₂N(Et)₂-C₆H₃ | H | 658; 7.48 (M1) NMR |

TABLE VI-continued

![Structure (I): pyrazolo-pyridazinone core with CH2-R1 on N, R2 on N, R3 and R4 substituents]

| Compound No. | R₁ | R₂ | R₃ | R₄ | MH+; tr (min) (Method) NMR |
|---|---|---|---|---|---|
| 124 SAR140308 | –C₆H₄–CF₃ (4-) | –C₆H₄–SMe (4-) | –C₆H₃(Cl)–S(CH₂)₂NHiPr | H | 644; 7.49 (M1) NMR |
| 125 SAR139298 | –C₆H₄–CF₃ (4-) | –C₆H₄–SMe (4-) | –C₆H₃(Cl)–S(CH₂)₂NHSO₂Me | H | 680; 9.8 (M1) NMR |
| 126 SAR140559 | –C₆H₄–CF₃ (4-) | –C₆H₄–SMe (4-) | –C₆H₃(Cl)–S(CH₂)₂NHCOH | H | 630; 9.41 (M1) NMR |
| 127 SAR142061 | –C₆H₄–CF₃ (4-) | –C₆H₄–SMe (4-) | –C₆H₃(Cl)–S(CH₂)₂NHCOCF₃ | H | 698; 10.54 (M1) NMR |
| 128 SAR142062 | –C₆H₄–CF₃ (4-) | pyridyl-SMe | –C₆H₃(Cl)–S(CH₂)₂NHCO–cyclopropyl | H | 670; 9.97 (M1) NMR |

Compound No. 7: ¹H NMR: DMSO-$d_6$ (400 MHz): δ (ppm): 1.18: d: 6H, 2.86: spt: 1H, 5.07: mt: 2H, 7.22: mt: 4H, 7.37-7.77: up: 8H.
Compound No. 8: ¹H NMR: DMSO-$d_6$ (200 MHz): δ (ppm): 1.25: s: 9H, 5.06: mt: 2H, 7.14-7.81: up: 12H.
Compound No. 13: ¹H NMR: DMSO-$d_6$ (250 MHz): δ (ppm): 5.23: mt: 2H, 7.40-7.80: up: 12H.
Compound No. 16: ¹H NMR: DMSO-$d_6$ (250 MHz): δ (ppm): 5.25: mt: 2H, 7.37-7.82: up: 11H.
Compound No. 23: ¹H NMR: DMSO-$d_6$ (250 MHz): δ (ppm): 5.21: mt: 2H, 7.28-7.94: up: 12H.
Compound No. 38: ¹H NMR: DMSO-$d_6$ (400 MHz): δ (ppm): 1.18: d: 6H, 2.86: spt: 1H, 5.07: mt: 2H, 7.14-7.74: up: 12H.
Compound No. 39: ¹H NMR: DMSO-$d_6$ (400 MHz): δ (ppm): 0.88: t: 3H, 1.29: mt: 2H, 1.52: mt: 2H, 2.55: mt: 2H, 7.01-7.85: up: 12H.
Compound No. 40: ¹H NMR: DMSO-$d_6$ (250 MHz): δ (ppm): 5.24: mt: 2H, 7.22-7.88: up: 11H.

Compound No. 41: ¹H NMR: DMSO-d$_6$ (250 MHz): δ (ppm): 5.16: mt: 2H, 7.30-7.73: up: 12H.
Compound No. 42: ¹H NMR: DMSO-d$_6$ (250 MHz): δ (ppm): 5.16: mt: 2H, 7.21-7.80: up: 12H.
Compound No. 44: ¹H NMR: DMSO-d$_6$ (250 MHz): δ (ppm): 2.45: s: 3H, 5.23: mt: 2H, 7.23: d: 2H, 7.36: d: 2H, 7.46: s: 1H, 7.53: mt: 3H, 7.65-7.78: up: 4H.
Compound No. 45: ¹H NMR: DMSO-d$_6$ (250 MHz): δ (ppm): 2.45: s: 3H, 5.26: up: 2H, 7.23: d: 2H, 7.36: d: 2H, 7.46: s: 1H, 7.49-7.79: up: 6H.
Compound No. 46: ¹H NMR: DMSO-d$_6$ (250 MHz): δ (ppm): 2.45: s: 3H, 5.16: mt: 2H, 7.23: d: 2H, 7.31-7.40: up: 4H, 7.42-7.57: up: 4H, 7.65-7.72: up: 2H.
Compound No. 60: ¹H NMR: DMSO-d$_6$ (250 MHz): δ (ppm): 5.21: mt: 2H, 7.32-7.53: up: 10H, 7.61-7.70: up: 2H.
Compound No. 62: ¹H NMR: DMSO-d$_6$ (400 MHz): δ (ppm): 3.74: s: 3H, 5.16: mt: 2H, 6.91: d: 2H, 7.30-7.55: up: 8H, 7.61-7.70: up: 2H.
Compound No. 65: ¹H NMR: DMSO-d$_6$ (250 MHz): δ (ppm): 3.73: s: 3H, 5.20: mt: 2H, 6.92: d: 2H, 7.36: d: 2H, 7.42-7.56: up: 4H, 7.61-7.79: up: 4H.
Compound No. 66: ¹H NMR: DMSO-d$_6$ (250 MHz): δ (ppm): 5.20: mt: 2H, 7.21: t: 2H, 7.31-7.55: up: 8H, 7.63: mt: 1H, 7.72: d: 2H.
Compound No. 77: ¹H NMR: DMSO-d$_6$ (250 MHz): δ (ppm): 2.92: mt: 2H, 3.88: mt: 2H, 5.21: mt: 2H, 7.37-7.79: up: 12H.
Compound No. 89: SAR112753: ¹H NMR: DMSO-d$_6$ (250 MHz): δ (ppm): 2.40: s: 3H, 5.18: rd: 2H, 7.18: d: 2H, 7.31: d: 2H, 7.40: s: 1H, 7.48: d: 2H, 7.55: d: 1H, 7.61: rd: 1H, 7.69: d: 2H, 7.73: d: 1H.
Compound No. 91: SAR115935: ¹H NMR: DMSO-d$_6$ (400 MHz): δ (ppm): 1.67: t: 2H, 2.45: s: 3H, 3.03: t: 2H, 3.47: mt: 2H, 4.61: t: 1H, 5.22: rd: 2H, 7.22: d: 2H, 7.28: rd: 1H, 7.31-7.36: 2mt: 3H, 7.40: s: 1H, 7.53: d: 3H, 7.73: d: 2H.
Compound No. 93: SAR118666: ¹H NMR: DMSO-d$_6$ (250 MHz): δ (ppm): 2.40: s: 3H, 5.15: rd: 2H, 7.18: d: 2H, 7.32: d: 2H, 7.42: 2mt: 3H, 7.55: d: 1H; 7.61: rd: 1H; 7.69: d: 2H, 7.73: d: 1H.
Compound No. 95: SAR119436: ¹H NMR: DMSO-d$_6$ (250 MHz): δ (ppm): 1.72: s: 3H, 2.39: s: 3H, 3.00: mt: 2H, 3.17: mt: 2H, 5.15: rd: 2H, 7.18: d: 2H, 7.29: 2 mt: 3H, 7.35: s: 1H; 7.37: d: 1H; 7.41: d: 2H, 7.49: d: 1H; 7.67: d: 2H, 8.05: t: 1H.
Compound No. 97: SAR119435: ¹H NMR: DMSO-d$_6$ (250 MHz): δ (ppm): 1.61: mt: 2H, 2.40: s: 3H, 2.97: t: 2H, 3.42: mt: 2H, 4.53: t: 1H; 5.15: rd: 2H, 7.13-7.33: up: 6H, 7.36: s: 1H; 7.42: d: 2H, 7.48: d: 1H; 7.67: d: 2H.
Compound No. 99: SSR156515: ¹H NMR: DMSO-d$_6$ (250 MHz): δ (ppm): 2.40: s: 3H, 3.70: s: 3H, 5.20: rd: 2H, 6.92: d: 1H; 6.98: d: 1H; 7.17: d: 2H, 7.29: d+mt: 3H, 7.48: d+mt: 3H, 7.69: d: 2H.
Compound No. 100: SSR156516: ¹H NMR: DMSO-d$_6$ (250 MHz): δ (ppm): 2.40: s: 3H, 3.71: s: 3H, 5.1: rd: 2H, 6.91: rd: 1H; 6.97: d: 1H; 7.16: d: 2H, 7.23-7.54: up: 8H.
Compound No. 101: SSR156517: ¹H NMR: DMSO-d$_6$ (250 MHz): δ (ppm): 2.42: s: 3H, 3.71: s: 3H, 8.14: rd: 2H, 6.92: rd: 1H; 6.98: d: 1H; 7.17: mt: 2H, 7.28: 2mt: 3H, 7.42: d: 2H, 7.49: d: 1H; 7.67: d: 2H.
Compound No. 102: SAR100912: ¹H NMR: DMSO-d$_6$ (250 MHz): δ (ppm): 2.12: s: 6H, 2.39: s: 3H, 2.51: t: 2H, 3.99: t: 2H, 5.17: rd: 2H, 6.91: rd: 1H, 6.98: d: 1H, 7.17: d: 2H, 7.29: d+mt: 3H, 7.43-7.53: up: 3H, 7.69: d: 2H.
Compound No. 104: SAR101384: ¹H NMR: DMSO-d$_6$ (250 MHz): δ (ppm): 2.06: s: 3H, 2.41: s: 3H, 2.75: t: 2H, 4.10: t: 2H, 5.7: rd: 2H, 6.93: rd: 1H, 7.00: d: 1H, 7.16: d: 2H, 7.29: d+mt: 3H, 7.48: d: 3H, 7.68: d: 2H.
Compound No. 105: SAR105567: ¹H NMR: DMSO-d$_6$ (400 MHz): δ (ppm): 2.46: s: 3H, 2.48: s: 3H, 5.22: rd: 2H, 7.18-2.30: up: 4H, 7.31-7.41: up: 3H, 7.53: d: 3H, 7.73: d: 2H.
Compound No. 107: SAR105565: ¹H NMR: DMSO-d$_6$ (400 MHz): δ (ppm): 2.46: s: 3H, 2.48: s: 3H, 5.20: rd: 2H, 7.20-7.32: up: 3H, 7.33-7.39: up: 3H, 7.46: d: 2H, 7.53: d: 1H, 7.72: d: 2H.
Compound No. 113: SAR124030: ¹H NMR: DMSO-d$_6$ (250 MHz): δ (ppm): 1.65: up: 2H, 2.81: s: 3H, 2.96: mt: 4H, 5.17: rd: 2H, 7.02: t: 1H, 7.27: 2d: 4H, 7.37-7.53: up: 4H, 7.56-7.75: up: 4H.
Compound No. 116: SAR122848: ¹H NMR: DMSO-d$_6$ (250 MHz): δ (ppm): 1.66: mt: 2H, 2.83: s: 3H, 2.97: mt: 4H, 5.18: rd: 2H, 7.01: t: 1H, 7.28: 2d: 4H, 7.41: s: 3H, 7.44-7.53: up: 3H, 7.63: mt: 1H, 7.69: d: 1H.
Compound No. 121: SAR137338A: ¹H NMR: DMSO-d$_6$ (400 MHz): δ (ppm): 2.23: bs: 2H, 2.45: s: 3H, 2.7: t: 2H, 3.01: t: 2H, 5.23: rd: 2H, 7.22: d: 2H, 7.31: d: 1H, 7.32-7.37: up: 3H, 7.41: s: 1H, 7.5-7.56: up: 3H, 7.73: d: 2H.
Compound No. 122: SAR137529: ¹H NMR: DMSO-d$_6$ (250 MHz): δ (ppm): 2.08: s: 6H, 2.37: t: 2H, 2.40: s: 3H, 3.05: t: 2H, 5.17: rd: 2H, 7.17: d: 2H, 7.25: d: 1H, 7.27-7.34: up: 3H, 7.36: s: 1H, 7.45-7.51: up: 3H, 7.69: d: 2H.
Compound No. 123: SAR139296: ¹H NMR: DMSO-d$_6$ (250 MHz): δ (ppm): 0.85: t: 6H, 2.32-2.5: up: 4H, 2.4: s: 3H, 2.52: t: 2H, 3.02: t: 2H, 5.18: rd: 2H, 7.17: d: 2H, 7.22-7.41: up: 5H, 7.42-7.54: up: 3H, 7.69: d: 2H.
Compound No. 124: SAR140308: ¹H NMR: DMSO-d$_6$ (250 MHz): δ (ppm): 0.86: d: 6H, 2.4: s: 3H, 2.6-2.74: up: 3H, 3.02: t: 2H, 5.18: rd: 2H, 7.17: d: 2H, 7.23-7.34: up: 4H, 7.36: s: 1H, 7.48: d: 3H, 7.69: d: 2H.
Compound No. 125: SAR139298: ¹H NMR: DMSO-d$_6$ (250 MHz): δ (ppm): 2.4: s: 3H, 2.85: s: 3H, 3.08: s: 4H, 5.2: rd: 2H, 7.18: d: 2H, 7.22-7.4: up: 6H, 7.44-7.61: up: 3H, 7.69: d: 2H.
Compound No. 126: SAR140559: ¹H NMR: DMSO-d$_6$ (250 MHz): δ (ppm): 2.4: s: 3H, 3.03: t: 2H, 3.2: t: 2H, 5.18: rd: 2H, 7.17: d: 2H, 7.17: d: 2H, 7.25-7.39: up: 5H, 7.44-7.55: up: 3H, 7.69: d: 2H, 7.97: s: 1H, 8.17: t: 1H.
Compound No. 127: SAR142061: ¹H NMR: DMSO-d$_6$ (250 MHz): δ (ppm): 2.39: s: 3H, 3.12: t: 2H, 3.32: q: 2H, 5.18: rd: 2H, 7.17: d: 2H, 7.26-7.39: up: 5H, 7.45-7.54: up: 3H, 7.69: d: 2H, 9.58: t: 1H.
Compound No. 128: SAR142062: ¹H NMR: DMSO-d$_6$ (250 MHz): δ (ppm): 0.55-0.66: up: 4H, 1.45: mt: 1H, 2.4: s: 3H, 3.01: t: 2H, 3.17: t: 2H, 5.18: rd: 2H, 7.17: d: 2H, 7.26-7.38: up: 5H, 7.44-7.55: up: 3H, 7.69: d: 2H, 8.28: t: 1H.

The compounds of formula (I) have a very good affinity in vitro (IC50≦5.10-7M) for human or rodent cannabinoid CB1 receptors, under the experimental conditions described by M. Rinaldi-Carmona et al. (FEBS Letters, 1994, 350, 240-244).

The antagonistic nature of the compounds of formula (I) was demonstrated by the results obtained in the models of adenylate cyclase inhibition as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The in vivo interaction of a compound of formula (I) with the CB 1 receptors present in the brain is determined in mice with the test for binding of [3H]-CP55940, ex vivo, after an intravenous injection or an oral administration as described in Rinaldi-Carmona M. et al., FEBS Letters 1994, 350, 240-244, Rinaldi-Carmona M. et al., Life Sciences 1995, 56, 1941-1947 and Rinaldi-Carmona M. et al., J. Pharmacol. Exp. Ther. 2004, 310, 905-914.

The in vivo interaction of a compound of formula (I) with the CB 1 receptors present at the periphery is determined in mice with the test for reversion of the inhibitory effect of CP55940 on gastrointestinal transit after an oral administration as described in Rinaldi-Carmona M. et al., J. Pharmacol. Exp. Ther. 2004, 310, 905-914.

The toxicity of the compounds of formula (I) is compatible with their use as a medicament.

Thus, according to another of its aspects, the invention relates to medicaments for human or veterinary medicine, which comprise a compound of formula (I), or an addition salt of the latter with a pharmaceutically acceptable acid, or else a solvate or a hydrate of the compound of formula (I).

Thus, the compounds according to the invention can be used in humans or in animals (in particular in mammals, including, in a non-limiting manner, dogs, cats, horses, cattle, sheep) in the treatment or prevention of diseases involving cannabinoid $CB_1$ receptors.

For example and in a non-limiting manner, the compounds of formula (I) can be used as psychotropic medicaments, in particular for the treatment of psychiatric disorders including anxiety, depression, mood disorders, insomnia, delirious conditions, obsessive disorders, psychoses in general, schizophrenia, attention deficit hyperactivity disorder (ADHD) in hyperkinetic children, and also for the treatment of disorders related to the use of psychotropic substances, in particular in the case of a substance abuse and/or a substance dependency, including alcohol dependency and nicotine dependency.

The compounds of formula (I) according to the invention can be used as medicaments for the treatment of migraine, stress, diseases of psychosomatic origin, panic attacks, epilepsy, motor disorders, in particular dyskinesia or Parkinson's disease, shaking and dystonia.

The compounds of formula (I) according to the invention can also be used as medicaments in the treatment of memory disorders, cognitive disorders, in particular in the treatment of senile dementia and Alzheimer's disease, and also in the treatment of attention or consciousness disorders. Furthermore, the compounds of formula (I) may be of use as neuroprotective agents, in the treatment of ischemia and cranial trauma and the treatment of acute or chronic neurodegenerative diseases, including chorea, Huntington's chorea and Tourette's syndrome.

The compounds of formula (I) according to the invention can be used as medicaments in the treatment of pain: neuropathic pain, acute peripheral pain, chronic pain of inflammatory origin, and pain caused by an anticancer treatment.

The compounds of formula (I) according to the invention can be used as medicaments in human or veterinary medicine, in the treatment and prevention of appetite disorders, appetence disorders (appetence for sugars, carbohydrates, drugs, alcohol or any appetizing substance) and/or eating behavioral disorders, in particular for the treatment of obesity or bulimia and also for the treatment of type II diabetes or non-insulin-dependent diabetes and for the treatment of dyslipidemia and metabolic syndrome. Thus, the compounds of formula (I) according to the invention can be used in the treatment and prevention of obesity and the risks associated with obesity, especially the cardiovascular risks.

Furthermore, the compounds of formula (I) according to the invention can be used as medicaments in the treatment and prevention of gastrointestinal disorders, diarrhea disorders, ulcers, vomiting, bladder and urinary disorders, liver diseases such as chronic cirrhosis, fibrosis, hepatic steatosis or steatohepatitis; and also disorders of endocrine origin, cardiovascular disorders, hypotension, atherosclerosis, hemorrhagic shock, septic shock, asthma, chronic bronchitis, chronic obstructive pulmonary diseases, Raynaud's syndrome, glaucoma, fertility disorders, interruption of pregnancy, premature birth, inflammatory phenomena, immune system diseases, in particular autoimmune diseases and neuroinflammatory diseases such as rheumatoid arthritis, rectional arthritis, diseases resulting in demyelinization, multiple sclerosis, infectious and viral diseases such as encephalitis, cerebral strokes, and also as medicaments for anticancer chemotherapy, for the treatment of Guillain-Barré syndrome and for the treatment of bone diseases and osteoporosis.

Furthermore, the compounds of formula (I) according to the invention can be used for their protective effects against drug-induced cardiotoxicity.

According to the present invention, the compounds of formula (I) can most particularly be used for the treatment of psychiatric disorders, in particular schizophrenia, attention and consciousness disorders, attention deficit hyperactivity disorders (ADHD) in hyperkinetic children; for the treatment of appetite disorders and obesity; for the treatment of memory deficiencies and cognitive disorders; for the treatment of dependency on and withdrawal from a substance, in particular alcohol dependency, nicotine dependency, alcohol withdrawal and tobacco withdrawal; acute or chronic neurodegenerative diseases.

More particularly, the compounds of formula (I) according to the present invention can be used in the preparation of medicaments which can be used in the treatment and prevention of appetite disorders, appetence disorders, metabolic disorders, obesity, type II diabetes, metabolic syndrome, dyslipidemia, gastrointestinal disorders, inflammatory phenomena, immune system diseases, psychotic disorders, alcohol dependency and nicotine dependency.

According to one of its aspects, the present invention relates to the use of a compound of formula (I), of its pharmaceutically acceptable salts, or of its solvates or hydrates, for the treatment of the disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, or a solvate or hydrate of said compound, and also at least one pharmaceutically acceptable excipient.

Said excipients are selected according to the pharmaceutical form and the method of administration desired, from the usual excipients known to those skilled in the art.

The pharmaceutical compositions according to the present invention can contain, along with a compound of formula (I), one (or more) other active ingredient(s) that can be used in the treatment of the disorders and diseases indicated above.

Thus, a subject of the present invention is also pharmaceutical compositions containing a compound of formula (I) according to the present invention combined with one (or more) active ingredient(s) selected from one of the following therapeutic classes:

another cannabinoid $CB_1$ receptor antagonist or allosteric modulators of cannabinoid $CB_1$ receptors;
a cannabinoid $CB_2$ receptor modulator;
an angiotensin II $AT_1$ receptor antagonist;
a converting enzyme inhibitor;
a calcium antagonist;
a diuretic;
a beta-blocker;
an antihyperlipemic or an antihypercholesterolemic;
an antidiabetic agent;

another anti-obesity agent or agent acting on metabolic disorders;
a nicotine agonist, a partial nicotine agonist;
an antidepressant, an antipsychotic, an anxiolytic;
an anticancer agent or an antiproliferative agent;
an opioid antagonist;
and also:
an agent for improving memory;
an agent that can be used in the treatment of alcoholism or withdrawal symptoms;
an agent that can be used for treating osteoporosis;
a non-steroidal or steroidal anti-inflammatory;
an anti-infective;
an analgesic;
an antiasthmatic.

The expression "angiotensin II $AT_1$ receptor antagonist" is intended to mean a compound such as candesartan cilexitil, eprosartan, irbesartan, losartan potassium, olmesartan medoxomil, telmisartan or valsartan, it being possible for each of these compounds to itself be combined with a diuretic such as hydrochlorothiazide.

The term "converting enzyme inhibitor" is intended to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril or zofenopril, it being possible for each of these compounds for itself to be combined with a diuretic such as hydrochlorothiazide or indapamide or with a calcium antagonist such as amlodipine, diltiazem, felodipine or verapamil.

The term "calcium antagonist" is intended to mean a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline or verapamil.

The term "beta-blocker" is intended to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol or xibenolol.

The term "antihyperlipemic" or "antihypercholesterolemic" is intended to mean a compound selected from fibrates, such as alufibrate, beclobrate, bezafibrate, ciprofibrate, clinofibrate, clofibrate, etofibrate or fenofibrate; statins (inhibitors of HMG-CoA reductase), such as atorvastatin, fluvastatin sodium, lovastatin, pravastatin, rosuvastatin, simvastatin, or a compound such as acipimox, aluminum nicotinate, azacosterol, cholestyramine, dextrothyroxine, meglutol, niceritrol, nicoclonate, nicotinic acid, beta-sitosterol or tiadenol.

The term "antidiabetic agent" is intended to mean a compound belonging to one of the following classes: sulfonylureas, biguanidines, alpha-glucosidase inhibitors, thiazolidinediones, metiglinides, such as acarbose, acetohexamide, carbutamide, chlorpropamide, glibenclamide, glibomuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone or voglibose, and also insulin and insulin analogues.

The expression "anti-obesity agent or agent for acting on metabolic disorders" is intended to mean a compound such as amfepramone, benfluorex, benzphetamine, indanorex, mazindole, mefenorex, methamphetamine, D-norpseudoephedrine, sibutramine, a topiramate, a lipase inhibitor (orlistat cetilistat), a PPAR agonist (Peroxisome Proliferator Activated Receptor Agonist), a dopamine agonist, a leptin receptor agonist, a serotonin re-uptake inhibitor, a beta-3 agonist, a CCK-A agonist, an NPY inhibitor, an MC4 receptor agonist, an MCH (Melanin Concentrating Hormone) receptor antagonist, an orexin antagonist, a phosphodiesterase inhibitor, an 11βHSD (11-β-hydroxy steroid dehydrogenase inhibitor), a DPP-IV (dipeptidyl peptidase IV) inhibitor, a histamine H3 antagonist (or inverse agonist), a CNTF (Ciliary Neurotrophic Factor) derivative, a GHS (Growth Hormone Secretagogue) receptor agonist, a ghrelin modulator, a diacylglycerol acyltransferase (DGAT) inhibitor, a phosphodiesterase (PDE) inhibitor, a thyroid hormone agonist, a glucocorticoid receptor antagonist, a stearoyl-CoA-desaturase (SCD) inhibitor, a phosphate transport, glucose transport, fatty acid transport or dicarboxylate transport modulator, a $5HT_2$ antagonist, a $5HT_6$ antagonist or a bombesin agonist.

The term "opioid antagonist" is intended to mean a compound such as naltrexone, naloxone or nalmefene.

The expression "agent that can be used in the treatment of alcoholism and withdrawal symptoms" is intended to mean acamprosate, benzodiazepines, beta-blockers, clonidine or carbamazepine.

The expression "agent that can be used for treating osteoporosis" is intended to mean, for example, bisphosphonates such as etidronate, clodronate, tiludronate or risedronate.

According to the present invention, other compounds with antihyperlipemic, antihypercholesterolemic, antidiabetic or anti-obesity properties may also be combined. More particularly, compounds belonging to one of the following classes may be combined:
PTP 1 B (Protein Tyrosine Phosphase-1B) inhibitors, VPAC 2 receptor agonists, GLK modulators, retinoid modulators, glycogen phosphorylase (HGLPa) inhibitors, glucagon antagonists, glucose-6-phosphate inhibitors, pyruvate dehydrogenase kinase (PKD) activators, RXR, FXR or LXR modulators, SGLT (Sodium Dependant Glucose Transporter) inhibitors, CETP (Cholesteryl Ester Transfer Protein) inhibitors, squalene synthetase inhibitors, squalene epoxidase inhibitors, triglyceride synthesis inhibitors, LDL (Low Density Lipoprotein) receptor inducers, IBAT inhibitors, FBPase (fructose-1,6-biphosphatase) inhibitors, CART (Cocaine-Amphetamine-Regulated Transcript) modulators, MC 4 (melanocortin 4) modulators and orexin receptor antagonists.

According to another aspect of the invention, the compound of formula (I), or one of its solvates or hydrates, and the other active ingredient combined can be administered simultaneously, separately or sequentially over time.

The term "simultaneous use" is intended to mean the administration of the compounds of the composition according to the invention within one and the same pharmaceutical form.

The term "separate use" is intended to mean the administration, at the same time, of the two compounds of the composition according to the invention, each within a separate pharmaceutical form.

The term "sequential use over time" is intended to mean the successive administration of the first compound of the composition of the invention, within one pharmaceutical form, and then of the second compound of the composition according to the invention, within a separate pharmaceutical form. In this case, the time elapsed between the administration of the first compound of the composition according to the invention and the administration of the second compound of the same composition according to the invention does not generally exceed 24 hours.

In the pharmaceutical compositions of the present invention for oral, sublingual, subcutaneous, intramuscular, intravenous, topical, local, intratracheal, intranasal, transdermal or rectal administration, the active ingredient of formula (I) above, or its possible solvate or hydrate, can be administered in a unit administration form, as a mixture with conventional pharmaceutical excipients, to animals and to human beings for the prophylaxis or treatment of the above disorders or diseases.

The appropriate unit administration forms include forms for oral administration, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

By oral administration, the dose of active ingredient administered per day can reach 0.01 to 100 mg/kg, taken as one or more dosage intakes, preferably 0.02 to 50 mg/kg.

There may be specific cases where higher or lower dosages are appropriate; such dosages do not depart from the scope of the invention. According to the usual practice, the dosage suitable for each patient is determined by the physician according to the method of administration and the weight and response of said patient.

According to another of its aspects, the present invention also relates to a method for treating the pathologies indicated above, which comprises the administration to a patient of an effective dose of a compound according to the invention, or hydrates or solvates.

What is claimed is:

1. A compound of formula (I):

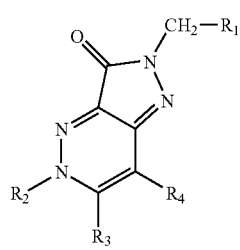

(I)

wherein:

$R_1$ is:
a $(C_1-C_{12})$alkyl which is unsubstituted or substituted one or more times with a fluorine atom;
a non-aromatic $(C_3-C_{12})$ carbocyclic radical which is unsubstituted or substituted one or more times with substituents selected independently from a $(C_1-C_4)$alkyl, a $(C_1-C_4)$alkoxy, a fluorine atom, a hydroxyl, trifluoromethyl radical, a trifluoromethoxy radical and a $(C_1-C_4)$alkylthio;
a phenyl which is unsubstituted or substituted one or more times with substituents selected independently from a halogen atom, a hydroxyl, an Alk group, an OAlk group, a methylenedioxy, a $CH_2$—NHAlk group, a —$CH_2N$(Alk)$_2$ group, a cyano, a nitro, an $S(O)_n$Alk group, an $OS(O)_n$Alk group, a $(C_1-C_4)$alkylcarbonyl group and a $(C_1-C_4)$alkoxycarbonyl group; or from a phenyl, phenoxy, pyrrolyl, imidazolyl, pyridyl, pyrazolyl, oxazolyl, thiazolyl, triazolyl or thiadiazolyl radical, said radical being unsubstituted or substituted one or more times with a $(C_1-C_4)$alkyl;
a benzyl which is unsubstituted or substituted one or more times on the phenyl with substituents selected independently from a halogen atom, an Alk group, a hydroxyl, an OAlk group, a methylenedioxy, an $S(O)_n$Alk group and an $OS(O)_n$Alk group;
a phenethyl which is unsubstituted or substituted one or more times on the phenyl with substituents selected independently from a halogen atom, a $(C_1-C_4)$alkyl, a $(C_1-C_4)$alkoxy, a trifluoromethyl radical and a trifluoromethoxy radical;
a benzhydryl; a benzhydrylmethyl;
an aromatic heterocyclic radical selected from a pyrrolyl, an imidazolyl, a furyl, a thienyl, a pyrazolyl, an oxazolyl, a pyridyl, an indolyl, a benzothienyl and a thieno[3,2-b]thienyl, said radical being unsubstituted or substituted one or more times with substituents selected independently from a halogen atom, an Alk group, an OAlk group, a cyano, a nitro and an $S(O)_n$Alk group;
$R_2$ is a phenyl which is unsubstituted or substituted one or more times with substituents selected independently from a halogen atom, a hydroxyl, an Alk group, an OAlk group, an $S(O)_n$Alk group, an $OS(O)_n$Alk group, an —$O(CH_2)_m R_5$ group or an —$S(CH_2)_m R_6$ group;
$R_3$ is a phenyl which is unsubstituted or substituted one or more times with substituents selected independently from a halogen atom, a hydroxyl, an Alk group, an OAlk group, an $S(O)_n$Alk group, an $OS(O)_n$Alk group, an —$O(CH_2)_m R_5$ group or an —$S(CH_2)_m R_6$ group;
$R_4$ is a hydrogen atom, a $(C_1-C_4)$alkyl, a $(C_1-C_4)$alkoxy or a hydroxyl;
$R_5$ is an —$NR_7R_8$ group or an —SAlk group;
$R_6$ is a hydroxyl, an —$NR_7R_8$ group, an $NR_7COR_8$ group or an —$NR_7SO_2R_9$ group;
$R_7$ is a hydrogen atom or a $(C_1-C_4)$alkyl;
$R_8$ is a hydrogen atom, an Alk group or a $(C_3-C_7)$cycloalkyl;
$R_9$ is a $(C_1-C_4)$alkyl;
m is 2 or 3;
n is 0, 1 or 2; and
Alk is a $(C_1-C_4)$alkyl which is unsubstituted or substituted one or more times with a fluorine atom;
or a salt thereof.

2. The compound of formula (I) according to claim 1, wherein:
$R_1$ is a $(C_1-C_{12})$alkyl which is unsubstituted or substituted one or more times with a fluorine atom; or a salt thereof.

3. The compound of formula (I) according to claim 1, wherein:
$R_1$ is a non-aromatic $(C_3-C_{12})$carbocyclic radical which is unsubstituted or substituted one or more times with substituents selected independently from a $(C_1-C_4)$alkyl, a $(C_1-C_4)$alkoxy, a fluorine atom, a hydroxyl, a trifluoromethyl radical, a trifluoromethoxy radical and a $(C_1-C_4)$alkylthio; or a salt thereof.

4. The compound of formula (I) according to claim 1, wherein
$R_1$ is a phenyl which is unsubstituted or substituted one or more times with substituents selected independently from a halogen atom, a hydroxyl, an Alk group, an OAlk group, a methylenedioxy, a $CH_2$—NHAlk group, a —$CH_2N(Alk)_2$ group, a cyano, a nitro, an $S(O)_n$Alk group, an $OS(O)_n$Alk group, a $(C_1-C_4)$alkylcarbonyl group and a $(C_1-C_4)$alkoxycarbonyl group; or from a phenyl, phenoxy, pyrrolyl, imidazolyl, pyridyl, pyrazolyl, oxazolyl, thiazolyl, triazolyl or thiadiazolyl radical, said radical being unsubstituted or substituted one or more times with a $(C_1-C_4)$alkyl; or a salt thereof.

5. The compound of formula (I) according to claim 1, wherein
$R_1$ is a benzyl which is unsubstituted or substituted one or more times on the phenyl with substituents selected independently from a halogen atom, an Alk group, a hydroxyl, an OAlk group, a methylenedioxy, an $S(O)_n$Alk group and an $OS(O)_n$Alk group; or a salt thereof.

6. The compound of formula (I), wherein
$R_1$ is an aromatic heterocyclic radical selected from a pyrrolyl, an imidazolyl, a furyl, a thienyl, a pyrazolyl, an oxazolyl, a pyridyl, an indolyl, a benzothienyl and a thieno[3,2-b]thienyl, said radical being unsubstituted or substituted one or more times with substituents selected independently from a halogen atom, an Alk group, an OAlk group, a cyano, a nitro and an $S(O)_n$Alk group; or a salt thereof.

7. The compound of formula (I) according to claim 1, wherein:
$R_1$ is:
a $(C_1-C_{12})$alkyl;
a $(C_3-C_7)$cycloalkyl which is unsubstituted or substituted with $(C_1-C_4)$alkyl, a trifluoromethyl radical; an adamantyl;
a phenyl which is unsubstituted or substituted one or more times with substituents selected independently from a halogen atom, an Alk group, an OAlk group, a $CH_2N(Alk)_2$ group, an —$S(O)_n$Alk group, a $(C_1-C_4)$alkoxycarbonyl group; or from a phenyl, triazolyl or thiadiazolyl radical;
a benzyl which is unsubstituted or substituted one or more times on the phenyl with substituents selected independently from a halogen atom and an Alk group;
an aromatic heterocyclic radical selected from a pyridyl, a thieno[3,2-b]thienyl and a benzothienyl, said radical being unsubstituted or substituted with a halogen atom or a trifluoromethyl radical;
$R_2$ is a phenyl mono- or disubstituted with a halogen atom, a hydroxyl, an OAlk group, an $S(O)_n$Alk group, an $OS(O)_n$Alk group, an —$O(CH_2)_mR_5$ group or an —$S(CH_2)_mR_6$ group;
$R_3$ is a phenyl mono- or disubstituted with a halogen atom, an OAlk group, an $S(O)_n$Alk group, an —$O(CH_2)_mR_5$ group or an —$S(CH_2)_mR_6$ group;
$R_4$ is a hydrogen atom, a $(C_1-C_4)$alkyl, a $(C_1-C_4)$alkoxy or a hydroxyl;
n is 0, 1 or 2; and
Alk is a $(C_1-C_4)$alkyl which is unsubstituted or substituted one or more times with a fluorine atom; or a salt thereof.

8. The compound of formula (I) according to claim 1, wherein:
$R_1$ is:
a 1-propylbutyl;
a cyclohexyl, a 4-tert-butylcyclohexyl, a 4-(trifluoromethyl)cyclohexyl; an adamantan-1-yl;
a phenyl, 4-fluorophenyl, a 2-methylphenyl, a 4-methylphenyl, a 4-isopropylphenyl, a 4-butylphenyl, a 4-tert-butylphenyl, a 4-(trifluoromethyl)phenyl, a 4-methoxyphenyl, a 4-butoxyphenyl, a 4-tert-butoxyphenyl, a 3-(trifluoro-methoxy)phenyl, a 4-(trifluoromethoxy)phenyl, a 4-(difluoromethoxy)phenyl, a 4-(1,1,2,2-tetrafluoroethoxy)phenyl, a 4-(ethylthio)phenyl, a 3-[(trifluoromethyl)thio]phenyl, a 4-[(trifluoromethyl)thio]phenyl, a 4-[(2,2,2-trifluoroethyl)thio]phenyl, a 4-(methylsulfonyl)phenyl, a 4-[[ethyl(propyl)amino]methyl]phenyl, a 4-[[methyl(2,2,2-trifluoroethyl)amino]methyl]phenyl, a 3-chloro-4-(trifluoromethyl)phenyl, a 2-fluoro-4-(trifluoromethyl)phenyl, a 3-fluoro-4-(trifluoromethyl)phenyl, a 3-fluoro-4-propoxyphenyl, a 3-chloro-4-(trifluoromethoxy)phenyl, a 3,5-bis(trifluoromethyl)phenyl, a 4-(methoxy-carbonyl)phenyl, a biphenyl-4-yl, a 4-(1H-1,2,4-triazol-1-yl)phenyl, a 4-(1,2,3-thiadiazol-4-yl)phenyl;
a benzyl, a [3,5-difluoro-4-(trifluoromethyl)phenyl]methyl;
a pyridin-4-yl, a 6-(trifluoromethyl)pyridin-3-yl, a thieno[3,2-b]thien-2-yl, a 5-chloro-1-benzothien-2-yl;
$R_2$ is a 4-bromophenyl, a 4-chlorophenyl, a 4-fluorophenyl, a 4-methoxyphenyl, a 4-(methylthio)phenyl, a 4-hydroxyphenyl, a 4-[[(3,3,3-trifluoropropyl)-sulfonyl]oxy]phenyl, a 4-[(propylsulfonyl)oxy]phenyl, a 2,4-dichlorophenyl, a 4-(trifluoromethoxy)phenyl, a 4-[(trifluoromethyl)thio]phenyl, a 4-[2-(dimethylamino)ethoxy]phenyl, a 4-[(3-hydroxypropyl)thio]phenyl, a 4-[(2-acetamidoethyl)thio]phenyl or a 4-[[3-[(methylsulfonyl)amino]propyl]thio]phenyl;
$R_3$ is a 2-chlorophenyl, a 4-chlorophenyl, a 2,4-dichlorophenyl, a 4-bromo-2-chlorophenyl, a 2-chloro-4-fluorophenyl, a 2-chloro-4-methoxyphenyl, a 2-chloro-4-(methylthio)phenyl, a 2-chloro-4-(ethylthio)phenyl, a 2-chloro-4-[(3,3,3-trifluoropropyl)thio]phenyl, a 2-chloro-4-(2,2,2-trifluoroethoxy)phenyl, a 2-chloro-4-[2-(dimethylamino)ethoxy]phenyl, a 2-chloro-4-[2-(methylthio)ethoxy]phenyl, a 2-chloro-4-[(3-hydroxypropyl)thio]phenyl, a 2-chloro-4-[(2-acetamidoethyl)thio]phenyl, a 2-chloro-4-[[3-[(methylsulfonyl)amino]propyl]thio]phenyl, a 4-[(2-aminoethyl)thio]-2-chlorophenyl, a 2-chloro-4-[[2-(dimethylamino)ethyl]thio]phenyl, a 2-chloro-4-[[2-(diethylamino)ethyl]thio]phenyl, a 2-chloro-4-[[2-(isopropylamino)ethyl]thio]phenyl, a 2-chloro-4-[(2-formamidoethyl)thio]phenyl, a 2-chloro-4-[[2-[(methylsulfonyl)amino]ethyl]thio]phenyl, a 2-chloro-4-[[2-[(trifluoroacetyl)amino]ethyl]thio]phenyl or a 2-chloro-4-[[2-[(cyclopropylcarbonyl)amino]ethyl]thio]phenyl; and
$R_4$ is a hydrogen atom, a methyl, a methoxy or a hydroxyl; or a salt thereof.

9. The compound of formula (I) according to claim 1, wherein:
$R_1$ is:
a 4-isopropylphenyl, a 4-tert-butylphenyl, a 4-(trifluoromethyl)phenyl, a 4-(trifluoromethoxy)phenyl, a 4-[(trifluoromethyl)thio]phenyl, a 2-fluoro-4-(trifluoromethyl)phenyl or a 3-fluoro-4-(trifluoromethyl)phenyl;

R₂ is a 4-bromophenyl, a 4-chlorophenyl, a 4-fluorophenyl, a 4-methoxyphenyl, a 4-(methylthio)phenyl, a 4-[[(3,3,3-trifluoropropyl)sulfonyl]oxy]phenyl, a 4-[(propylsulfonyl)oxy]phenyl or a 4-[[3-[(methylsulfonyl)amino]propyl]-thio]phenyl;

R₃ is a 2-chlorophenyl, a 2,4-dichlorophenyl, a 4-bromo-2-chlorophenyl, a 2-chloro-4-methoxyphenyl, a 2-chloro-4-(methylthio)phenyl, a 2-chloro-4-[2-(dimethylamino)ethoxy]phenyl, a 2-chloro-4-[2-(methylthio)ethoxy]phenyl, a 2-chloro-4-[(3-hydroxypropyl)thio]phenyl, a 2-chloro-4-[(2-acetamidoethyl)thio]phenyl, a 4-[(2-aminoethyl)thio]-2-chlorophenyl, a 2-chloro-4-[[2-(dimethylamino)ethyl]thio]phenyl, a 2-chloro-4-[[2-(diethylamino)ethyl]thio]phenyl, a 2-chloro-4-[[2-(isopropylamino)-ethyl]thio]phenyl, a 2-chloro-4-[[2-[(methylsulfonyl)amino]ethyl]thio]phenyl, a 2-chloro-4-[(2-formamidoethyl)thio]phenyl, a 2-chloro-4-[[2-[(trifluoroacetyl)-amino]ethyl]thio]phenyl or a 2-chloro-4-[[2-[(cyclopropylcarbonyl)amino]-ethyl]thio]phenyl; and R₄ is a hydrogen atom;

or a salt thereof.

10. The compound of formula (I) according to claim 1, which is selected from:

5-(4-chlorophenyl)-6-(2,4-dichlorophenyl)-2-(4-isopropylbenzyl)-2,5-dihydro-3H-pyrazolo[4,3-c]pyridazin-3-one;

2-(4-tert-butylbenzyl)-5-(4-chlorophenyl)-6-(2,4-dichlorophenyl)-2,5-dihydro-3H-pyrazolo[4,3-c]pyridazin-3-one;

5-(4-chlorophenyl)-6-(2,4-dichlorophenyl)-2-[4-(trifluoromethyl)benzyl]-2,5-dihydro-3H-pyrazolo[4,3-c]pyridazin-3-one;

5-(4-chlorophenyl)-6-(2,4-dichlorophenyl)-2-[2-fluoro-4-(trifluoromethyl)benzyl]-2,5-dihydro-3H-pyrazolo[4,3-c]pyridazin-3-one;

5-(4-chlorophenyl)-6-(2,4-dichlorophenyl)-2-[4-[(trifluoromethyl)thio]benzyl]-2,5-dihydro-3H-pyrazolo[4,3-c]pyridazin-3-one;

5-(4-bromophenyl)-6-(2,4-dichlorophenyl)-2-(4-isopropylbenzyl)-2,5-dihydro-3H-pyrazolo[4,3-c]pyridazin-3-one;

5-(4-bromophenyl)-2-(4-butylbenzyl)-6-(2,4-dichlorophenyl)-2,5-dihydro-3H-pyrazolo[4,3-c]pyridazin-3-one;

5-(4-bromophenyl)-6-(2,4-dichlorophenyl)-2-[3-fluoro-4-(trifluoromethyl)benzyl]-2,5-dihydro-3H-pyrazolo[4,3-c]pyridazin-3-one;

5-(4-bromophenyl)-6-(2,4-dichlorophenyl)-2-[4-(trifluoromethoxy)benzyl]-2,5-dihydro-3H-pyrazolo[4,3-c]pyridazin-3-one;

5-(4-bromophenyl)-6-(2,4-dichlorophenyl)-2-[4-[(trifluoromethyl)thio]benzyl]-2,5-dihydro-3H-pyrazolo[4,3-c]pyridazin-3-one;

6-(2,4-dichlorophenyl)-5-[4-(methylthio)phenyl]-2-[4-(trifluoromethyl)benzyl]-2,5-dihydro-3H-pyrazolo[4,3-c]pyridazin-3-one;

6-(2,4-dichlorophenyl)-2-[2-fluoro-4-(trifluoromethyl)benzyl]-5-[4-(methylthio)phenyl]-2,5-dihydro-3H-pyrazolo[4,3-c]pyridazin-3-one;

6-(2,4-dichlorophenyl)-5-[4-(methylthio)phenyl]-2-[4-(trifluoromethoxy)benzyl]-2,5-dihydro-3H-pyrazolo[4,3-c]pyridazin-3-one;

6-(2-chlorophenyl)-5-(4-chlorophenyl)-2-[4-[(trifluoromethyl)thio]benzyl]-2,5-dihydro-3H-pyrazolo[4,3-c]pyridazin-3-one;

6-(2,4-dichlorophenyl)-5-(4-methoxyphenyl)-2-[4-[(trifluoromethoxy)benzyl]-2,5-dihydro-3H-pyrazolo[4,3-c]pyridazin-3-one;

6-(2,4-dichlorophenyl)-5-(4-methoxyphenyl)-2-[4-[(trifluoromethyl)thio]benzyl]-2,5-dihydro-3H-pyrazolo[4,3-c]pyridazin-3-one;

6-(2-chlorophenyl)-5-(4-fluorophenyl)-2-[4-[(trifluoromethyl)thio]benzyl]-2,5-dihydro-3H-pyrazolo[4,3-c]pyridazin-3-one;

4-[6-(2,4-dichlorophenyl)-3-oxo-2-[4-[(trifluoromethyl)thio]benzyl]-2,3-dihydro-5H-pyrazolo[4,3-c]pyridazin-5-yl]phenyl-3,3,3-trifluoropropane-1-sulfonate;

4-[6-(2,4-dichlorophenyl)-3-oxo-2-[4-[(trifluoromethyl)thio]benzyl]-2,3-dihydro-5H-pyrazolo[4,3-c]pyridazin-5-yl]phenylpropane-1-sulfonate;

6-(4-bromo-2-chlorophenyl)-5-[4-(methylthio)phenyl]-2-[4-(trifluoromethyl)benzyl]-2,5-dihydro-3H-pyrazolo[4,3-c]pyridazin-3-one;

6-{2-chloro-4-[(3-hydroxypropyl)thio]phenyl}-5-[4-(methylthio)phenyl]-2-[4-(trifluoromethyl)benzyl]-2,5-dihydro-3H-pyrazolo[4,3-c]pyridazin-3-one;

6-(4-bromo-2-chlorophenyl)-5-[4-(methylthio)phenyl]-2-{4-[(trifluoromethyl)thio]benzyl}-2,5-dihydro-3H-pyrazolo[4,3-c]pyridazin-3-one;

N-(2-{[3-chloro-4-(5-[4-(methylthio)phenyl]-3-oxo-2-{4-[(trifluoromethyl)thio]benzyl}-3,5-dihydro-2H-pyrazolo[4,3-c]pyridazin-6-yl)phenyl]thio}ethyl)acetamide;

6-{2-chloro-4-[(3-hydroxypropyl)thio]phenyl}-5-[4-(methylthio)phenyl]-2-{4-[(trifluoromethyl)thio]benzyl}-2,5-dihydro-3H-pyrazolo[4,3-c]pyridazin-3-one;

6-(2-chloro-4-methoxyphenyl)-5-[4-(methylthio)phenyl]-2-[4-(trifluoromethyl)benzyl]-2,5-dihydro-3H-pyrazolo[4,3-c]pyridazin-3-one;

6-(2-chloro-4-methoxyphenyl)-5-[4-(methylthio)phenyl]-2-[4-(trifluoromethoxy)benzyl]-2,5-dihydro-3H-pyrazolo[4,3-c]pyridazin-3-one;

6-(2-chloro-4-methoxyphenyl)-5-[4-(methylthio)phenyl]-2-{4-[(trifluoromethyl)thio]benzyl}-2,5-dihydro-3H-pyrazolo[4,3-c]pyridazin-3-one;

6-{2-chloro-4-[2-(dimethylamino)ethoxy]phenyl}-5-[4-(methylthio)phenyl]-2-[4-(trifluoromethyl)benzyl]-2,5-dihydro-3H-pyrazolo[4,3-c]pyridazin-3-one;

6-{2-chloro-4-[2-(methylthio)ethoxy]phenyl}-5-[4-(methylthio)phenyl]-2-[4-(trifluoromethyl)benzyl]-2,5-dihydro-3H-pyrazolo[4,3-c]pyridazin-3-one;

6-[2-chloro-4-(methylthio)phenyl]-5-[4-(methylthio)phenyl]-2-[4-(trifluoromethyl)benzyl]-2,5-dihydro-3H-pyrazolo[4,3-c]pyridazin-3-one;

6-[2-chloro-4-(methylthio)phenyl]-5-[4-(methylthio)phenyl]-2-{4-[(trifluoromethyl)thio]benzyl}-2,5-dihydro-3H-pyrazolo[4,3-c]pyridazin-3-one;

N-[3-({4-[6-(2,4-dichlorophenyl)-3-oxo-2-{4-[(trifluoromethyl)thio]benzyl}-2,3-dihydro-5H-pyrazolo[4,3-c]pyridazin-5-yl]phenyl}thio)propyl]methane-sulfonamide;

N-{3-[(4-{6-(2,4-dichlorophenyl)-3-oxo-2-[4-(trifluoromethyl)benzyl]-2,3-dihydro-5H-pyrazolo[4,3-c]pyridazin-5-yl}phenyl)thio]propyl}methanesulfonamide;

6-{4-[(2-aminoethyl)thio]-2-chlorophenyl}-5-[4-(methylthio)phenyl]-2-[4-(trifluoromethyl)benzyl]-2,5-dihydro-3H-pyrazolo[4,3-c]pyridazin-3-one;

SAR 137529: 6-(2-chloro-4-{[2-(dimethylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one;

6-(2-chloro-4-{[2-(diethylamino)ethyl]thio}phenyl-5-[4-(methylthio)phenyl]-2-[4-(trifluoromethyl)benzyl]-2,5-dihydro-3H-pyrazolo[4,3-c]pyridazin-3-one;

6-(2-chloro-4-{[2-(isopropylamino)ethyl]thio}phenyl)-5-[4-(methylthio)phenyl]-2-[4-(trifluoromethyl)benzyl]-2,5-dihydro-3H-pyrazolo[4,3-c]pyridazin-3-one;

N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}methanesulfonamide;

N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}formamide;

N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}-2,2,2-trifluoroacetamide; and N-{2-[(3-chloro-4-{5-[4-(methylthio)phenyl]-3-oxo-2-[4-(trifluoromethyl)benzyl]-3,5-dihydro-2H-pyrazolo[4,3-c]pyridazin-6-yl}phenyl)thio]ethyl}cyclopropanecarboxamide;

or a salt thereof.

11. A pharmaceutical composition comprising a compound of formula (I) according to claim 1 or a pharmaceutically acceptable salt thereof in combination with at least one pharmaceutically acceptable excipient.

12. A pharmaceutical composition comprising a compound of formula (I) according to claim 2 or a pharmaceutically acceptable salt thereof in combination with at least one pharmaceutically acceptable excipient.

13. A pharmaceutical composition comprising a compound of formula (I) according to claim 3 or a pharmaceutically acceptable salt thereof in combination with at least one pharmaceutically acceptable excipient.

14. A pharmaceutical composition comprising a compound of formula (I) according to claim 4 or a pharmaceutically acceptable salt thereof in combination with at least one pharmaceutically acceptable excipient.

15. A pharmaceutical composition comprising a compound of formula (I) according to claim 5 or a pharmaceutically acceptable salt thereof in combination with at least one pharmaceutically acceptable excipient.

16. A pharmaceutical composition comprising a compound of formula (I) according to claim 6 or a pharmaceutically acceptable salt thereof in combination with at least one pharmaceutically acceptable excipient.

17. A pharmaceutical composition comprising a compound of formula (I) according to claim 7 or a pharmaceutically acceptable salt thereof in combination with at least one pharmaceutically acceptable excipient.

18. A pharmaceutical composition comprising a compound of formula (I) according to claim 8 or a pharmaceutically acceptable salt thereof in combination with at least one pharmaceutically acceptable excipient.

19. A pharmaceutical composition comprising a compound of formula (I) according to claim 9 or a pharmaceutically acceptable salt thereof in combination with at least one pharmaceutically acceptable excipient.

20. A pharmaceutical composition comprising a compound of formula (I) according to claim 10 or a pharmaceutically acceptable salt thereof in combination with at least one pharmaceutically acceptable excipient.

* * * * *